(12) United States Patent
Park et al.

(10) Patent No.: US 10,422,576 B2
(45) Date of Patent: Sep. 24, 2019

(54) GAS SENSOR, REFRIGERATOR INCLUDING SAME AND CONTROL METHOD THEREFOR

(71) Applicant: SAMSUNG ELECTRONICS CO., LTD., Suwon-si, Gyeonggi-do (KR)

(72) Inventors: Jang Pyo Park, Hwaseong-si (KR); Youn Joo Song, Suwon-si (KR); Yong Won Jeong, Seoul (KR); Hyun Joo Jung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 279 days.

(21) Appl. No.: 15/327,552

(22) PCT Filed: Apr. 2, 2015

(86) PCT No.: PCT/KR2015/003337
§ 371 (c)(1),
(2) Date: Jan. 19, 2017

(87) PCT Pub. No.: WO2016/013753
PCT Pub. Date: Jan. 28, 2016

(65) Prior Publication Data
US 2017/0160005 A1 Jun. 8, 2017

(30) Foreign Application Priority Data
Jul. 21, 2014 (KR) ........................ 10-2014-0092022

(51) Int. Cl.
*F25D 29/00* (2006.01)
*G01N 21/80* (2006.01)
(Continued)

(52) U.S. Cl.
CPC ........... *F25D 29/00* (2013.01); *F25D 25/005* (2013.01); *F25D 29/005* (2013.01);
(Continued)

(58) Field of Classification Search
CPC ...... F25D 29/00; F25D 25/005; F25D 29/005; F25D 2700/06; F25D 17/042;
(Continued)

(56) References Cited

U.S. PATENT DOCUMENTS 3,754,867 A 8/1973 Guenther
8,277,732 B1 10/2012 Osborne et al.
(Continued)

FOREIGN PATENT DOCUMENTS

CN 101036050 A 9/2007
CN 101936912 A 1/2011
(Continued)

OTHER PUBLICATIONS

Extended European Search Report dated Apr. 19, 2018 in European Patent Application No. 15825283.3.
(Continued)

*Primary Examiner* — Dennis White
(74) *Attorney, Agent, or Firm* — Staas & Halsey LLP

(57) ABSTRACT

A gas sensor includes a plurality of detectors discolored by reacting with different predetermined target gases, such that the gas sensor independently measures the amount of each target gas. A refrigerator for deciding a type and state of target food contained in a container by sensing a color change of a gas sensor mounted to the container including the target food, and a method for controlling the gas sensor are disclosed. The gas sensor for detecting a plurality of target gases includes a base and a plurality of detectors provided at the base. The detectors respectively detect different target gases, and each detector is discolored by reacting with each predetermined target gas.

17 Claims, 41 Drawing Sheets

(51) Int. Cl.

| | | |
|---|---|---|
| *F25D 25/00* | (2006.01) | |
| *G01N 21/78* | (2006.01) | |
| *G01N 31/22* | (2006.01) | |
| *G01N 33/00* | (2006.01) | |
| *G01N 33/02* | (2006.01) | |
| *F25D 17/04* | (2006.01) | |
| *G01N 21/77* | (2006.01) | |

(52) U.S. Cl.
CPC ........... *G01N 21/783* (2013.01); *G01N 21/80* (2013.01); *G01N 31/223* (2013.01); *G01N 33/00* (2013.01); *G01N 33/02* (2013.01); *F25D 17/042* (2013.01); *F25D 2400/36* (2013.01); *F25D 2600/04* (2013.01); *F25D 2700/06* (2013.01); *G01N 2021/775* (2013.01)

(58) Field of Classification Search
CPC . F25D 2400/36; F25D 2600/04; G01N 33/00; G01N 31/223; G01N 21/783; G01N 33/02; G01N 21/80; G01N 2021/775
See application file for complete search history.

(56) References Cited

U.S. PATENT DOCUMENTS

| | | | |
|---|---|---|---|
| 2006/0090542 A1* | 5/2006 | Nakano | G01N 31/223 73/23.35 |
| 2009/0301381 A1 | 12/2009 | Robins | |
| 2013/0015753 A1* | 1/2013 | Son | F25D 29/00 312/405 |
| 2013/0057078 A1 | 3/2013 | Lee et al. | |
| 2013/0096030 A1* | 4/2013 | Jeppesen | C07D 495/04 506/12 |
| 2013/0110064 A1 | 5/2013 | Richardson et al. | |

FOREIGN PATENT DOCUMENTS

| | | |
|---|---|---|
| CN | 201819507 U | 5/2011 |
| JP | 2002-361015 | 12/2002 |
| KR | 2001-0113246 | 12/2001 |
| KR | 10-2005-008049 | 1/2005 |
| KR | 10-2006-0106080 | 10/2006 |
| WO | 98/20337 | 5/1998 |

OTHER PUBLICATIONS

Extended European Search Report dated Jan. 9, 2018 in European Patent Application No. 15825283.3.
International Search Report dated Aug. 26, 2015 in corresponding International Application No. PCT/KR2015/003337.
European Office Action dated Mar. 7, 2019 in European Patent Application No. 15825283.3.
Chinese Office Action dated Apr. 2, 2019 in Chinese Patent Application No. 201580049368.

* cited by examiner

[Fig. 1]
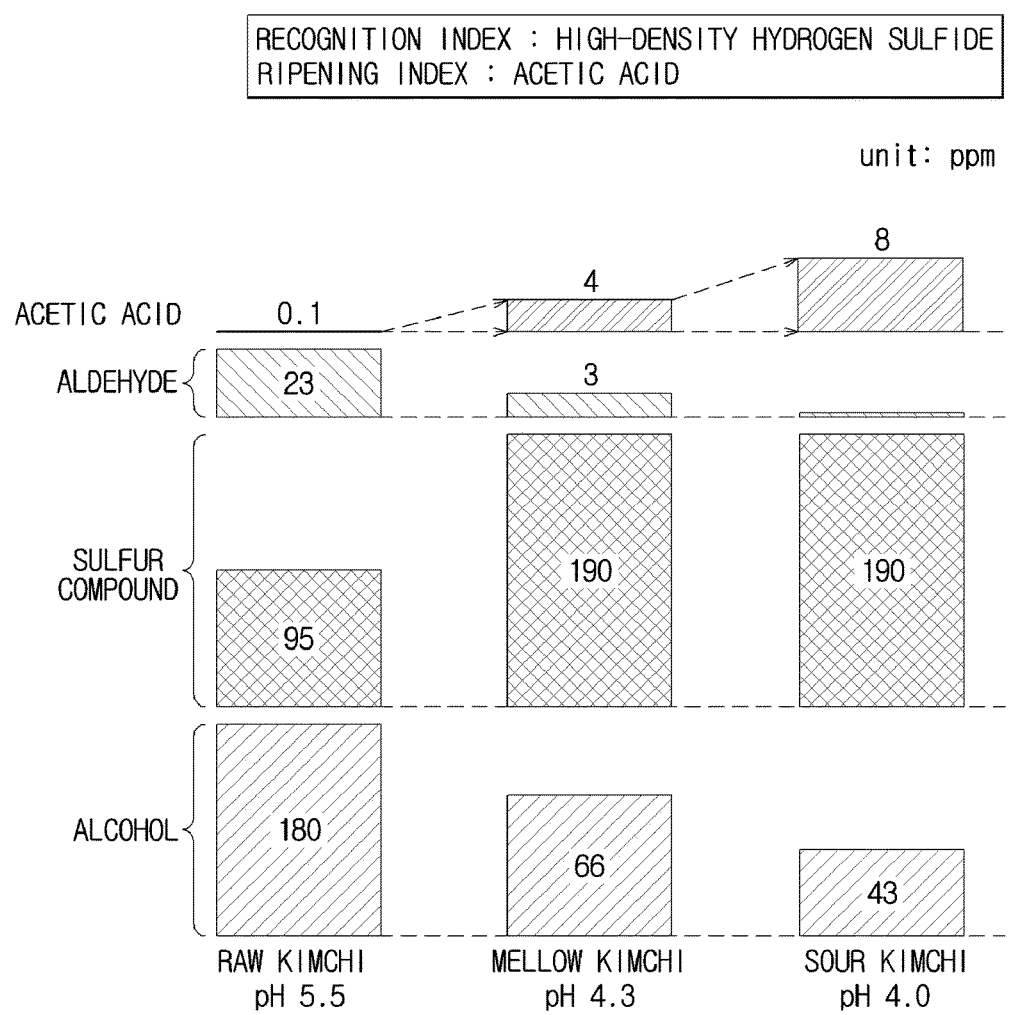

[Fig. 2]
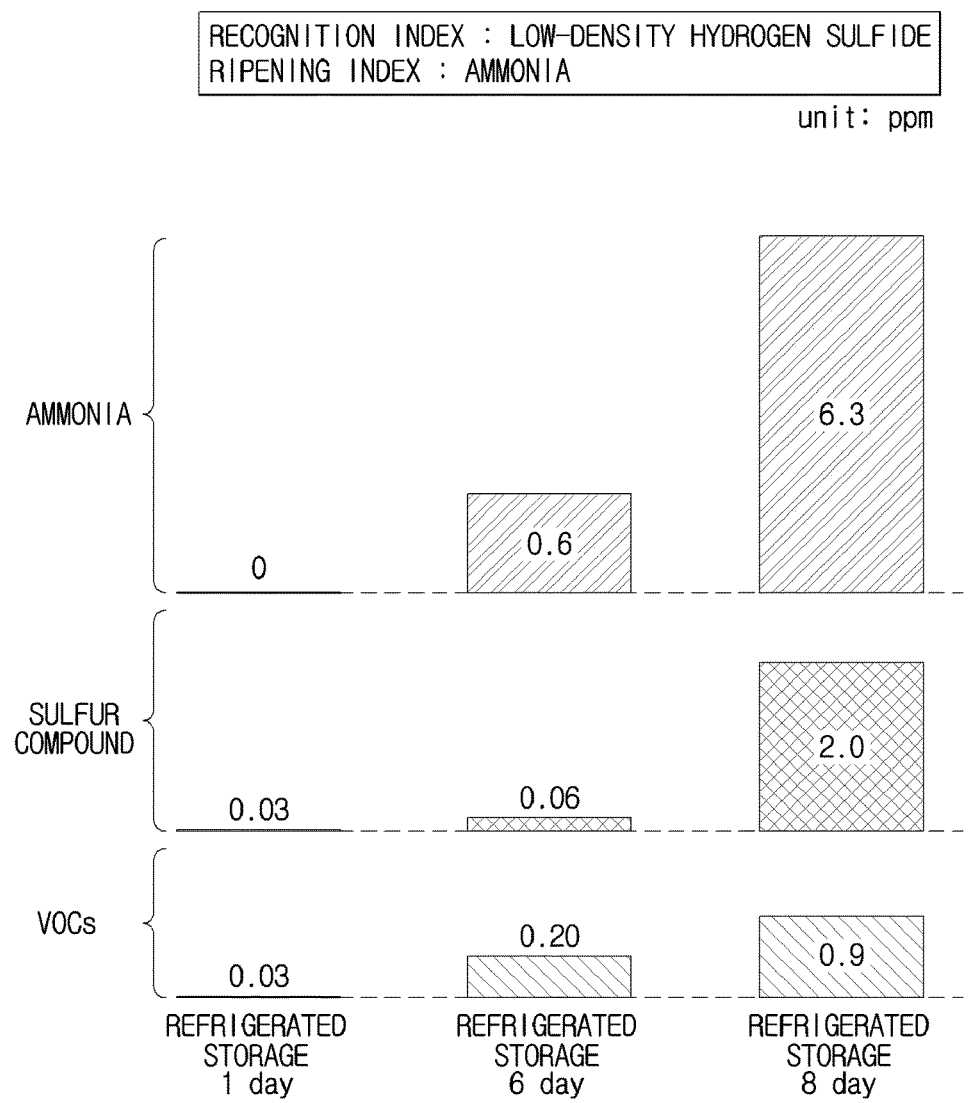

[Fig. 3]
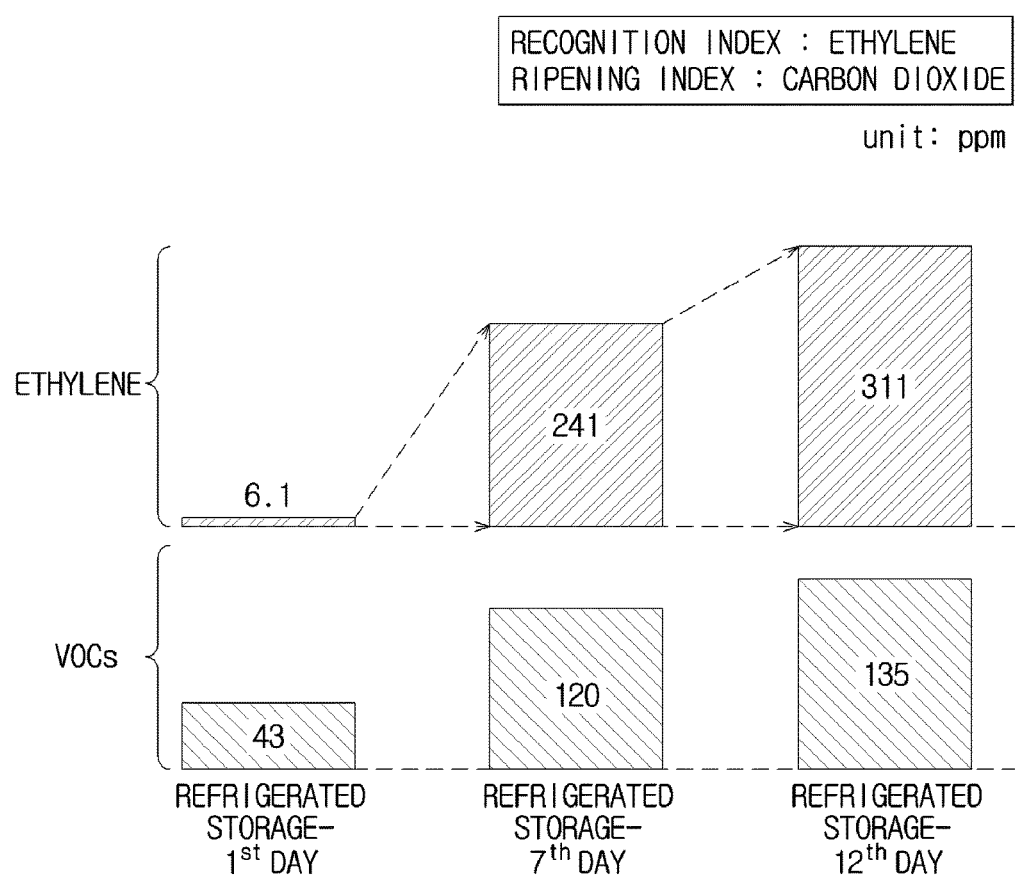

[Fig. 4]
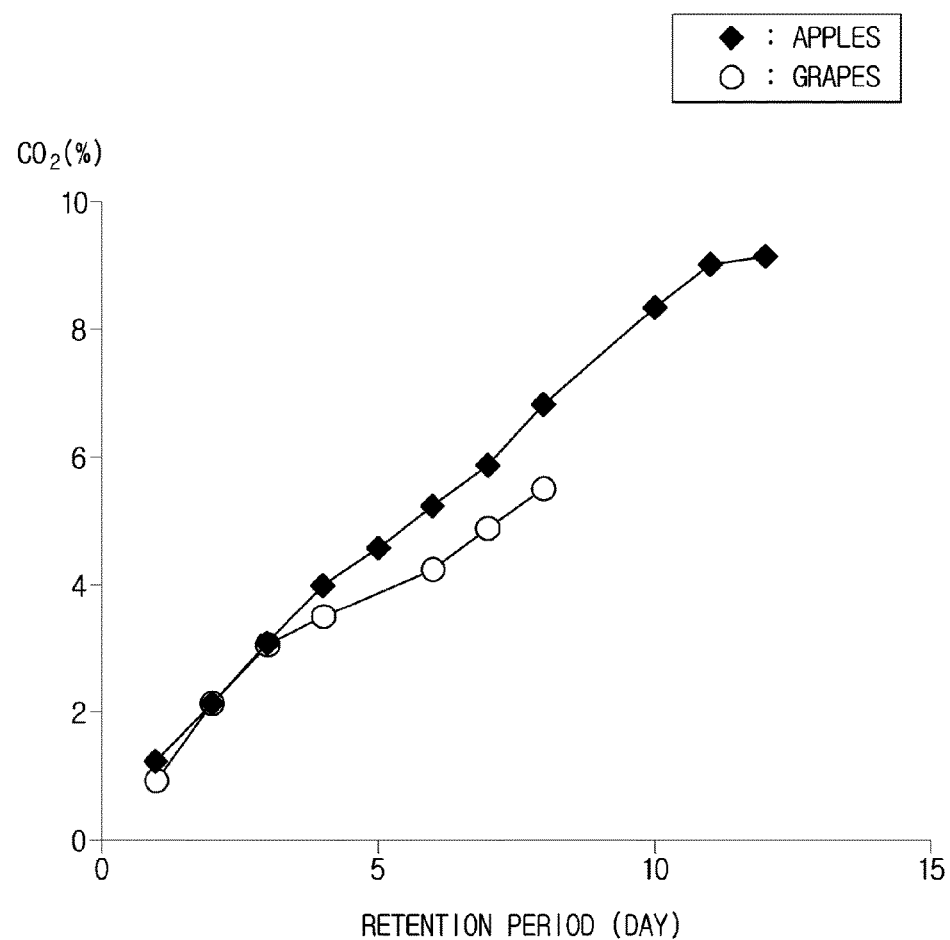

[Fig. 5]
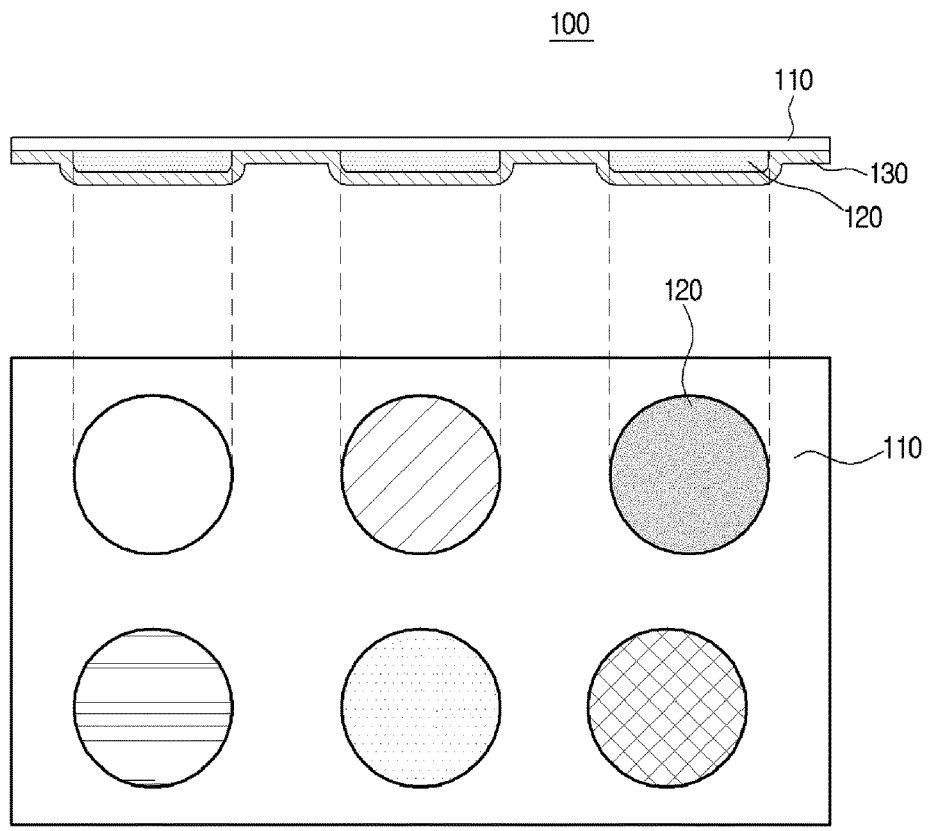
[Fig. 6]
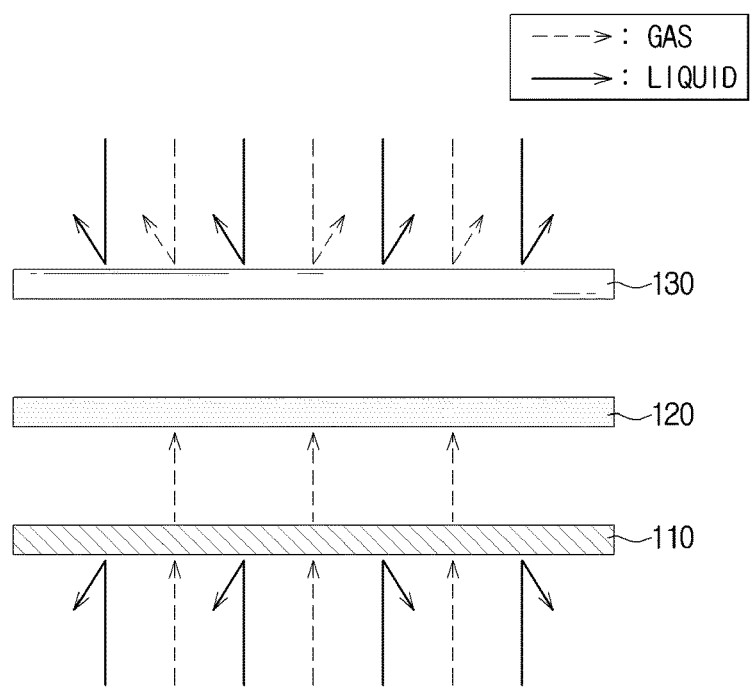

[Fig. 7]
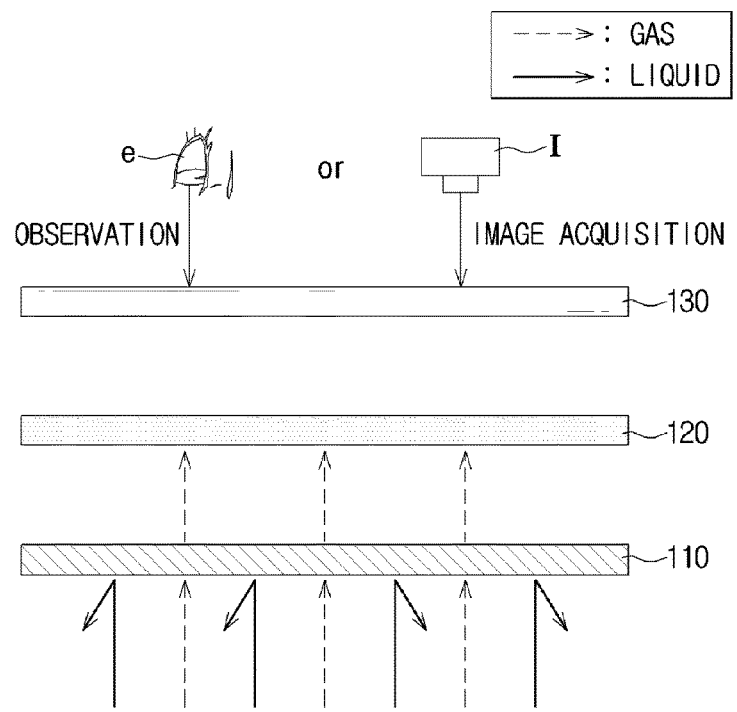
[Fig. 8]
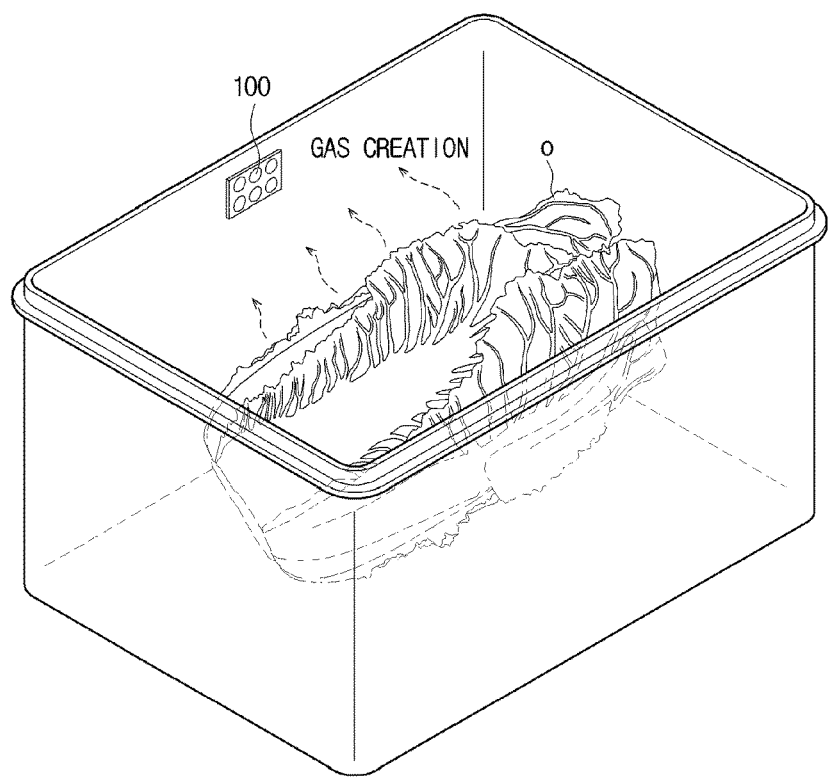

[Fig. 9]
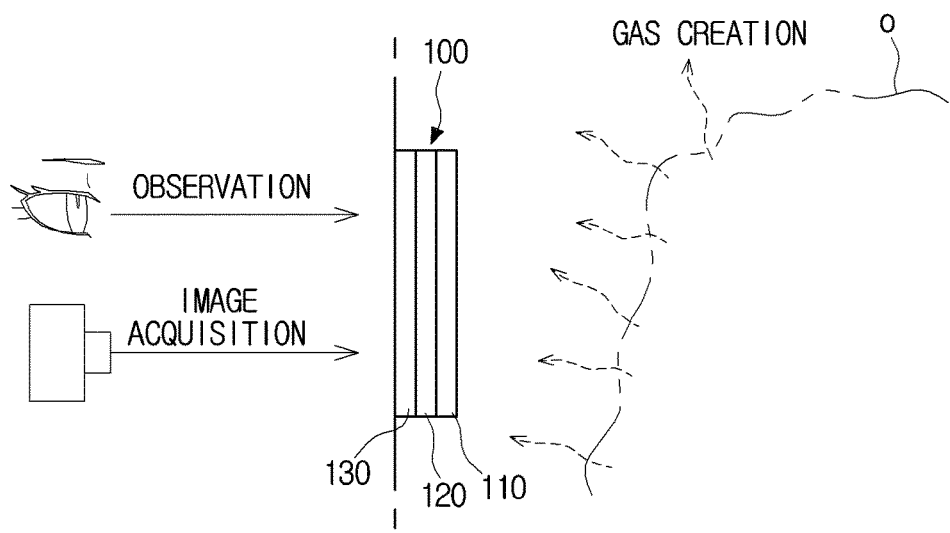
[Fig. 10]
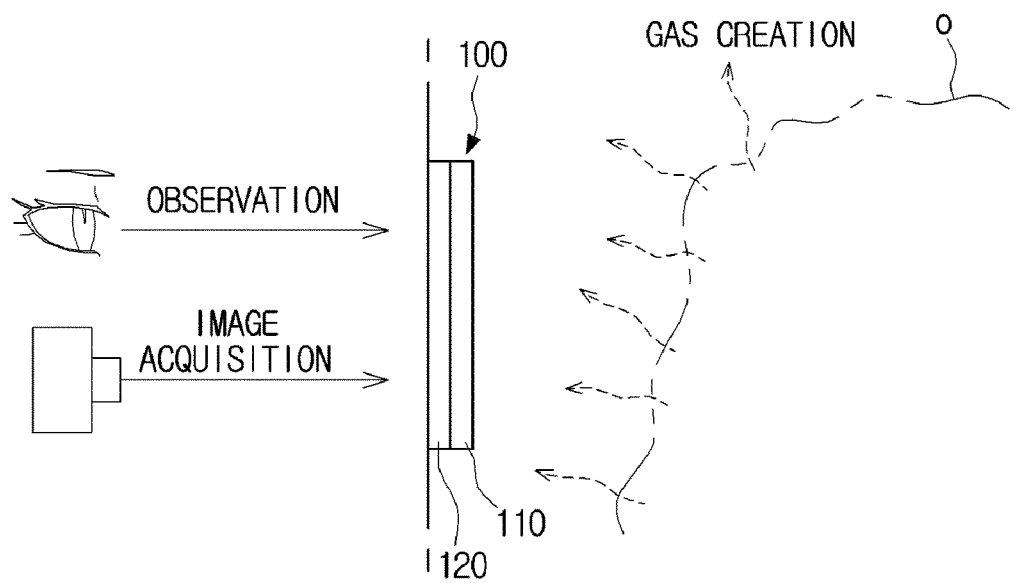

[Fig. 11]
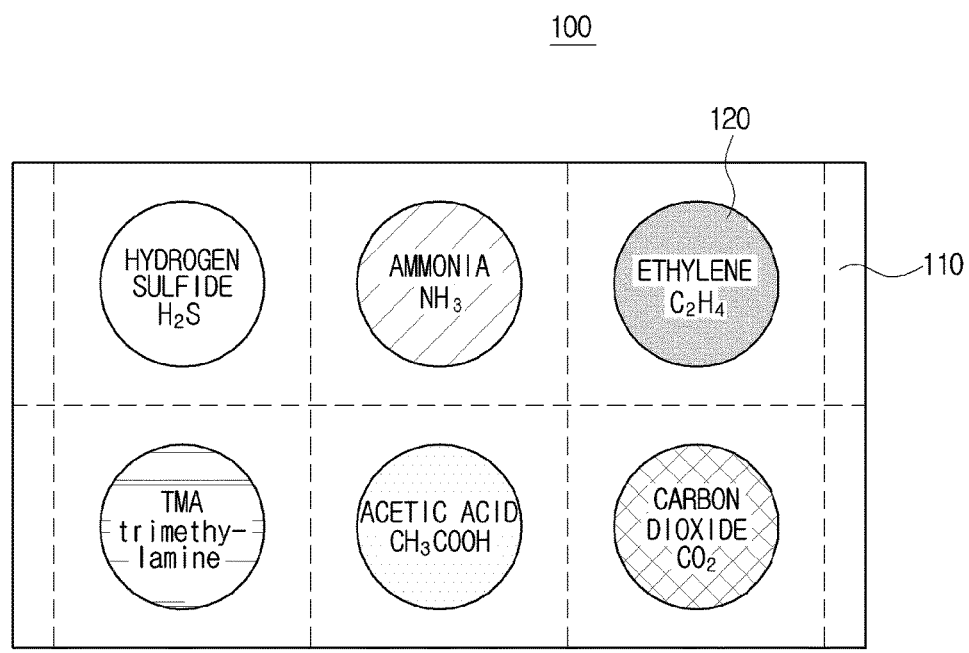

[Fig. 12]
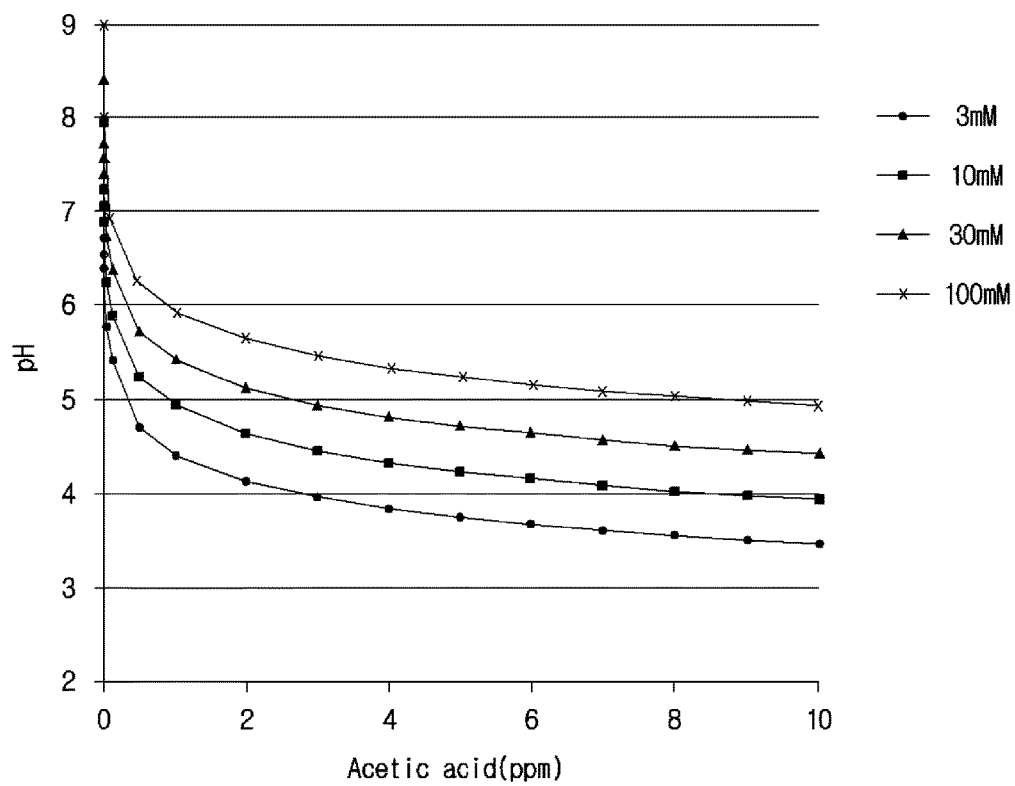

[Fig. 13]
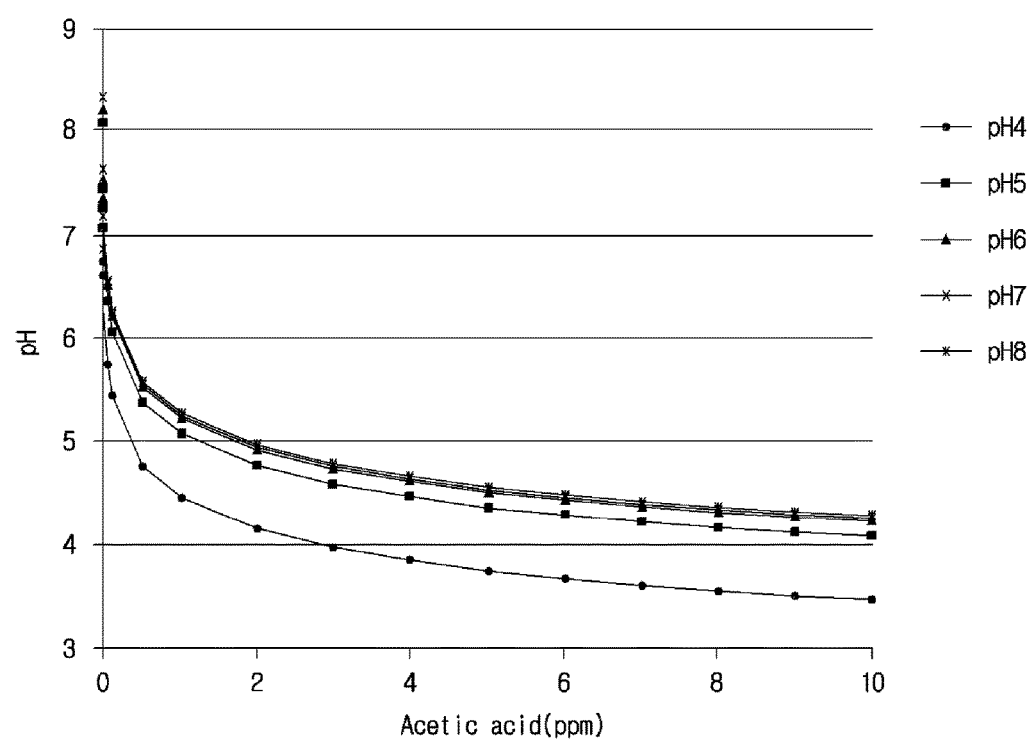

[Fig. 14]
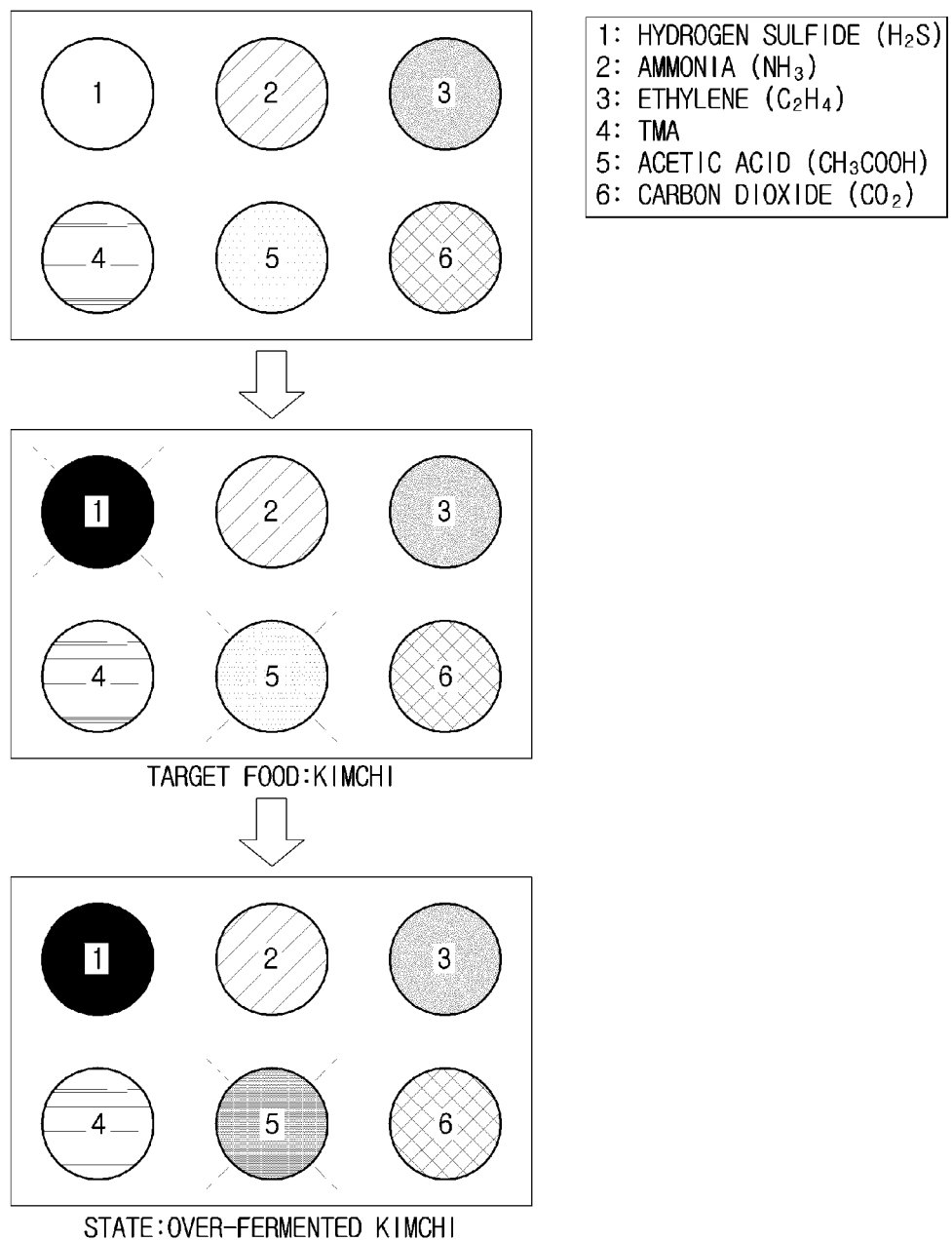

[Fig. 15]
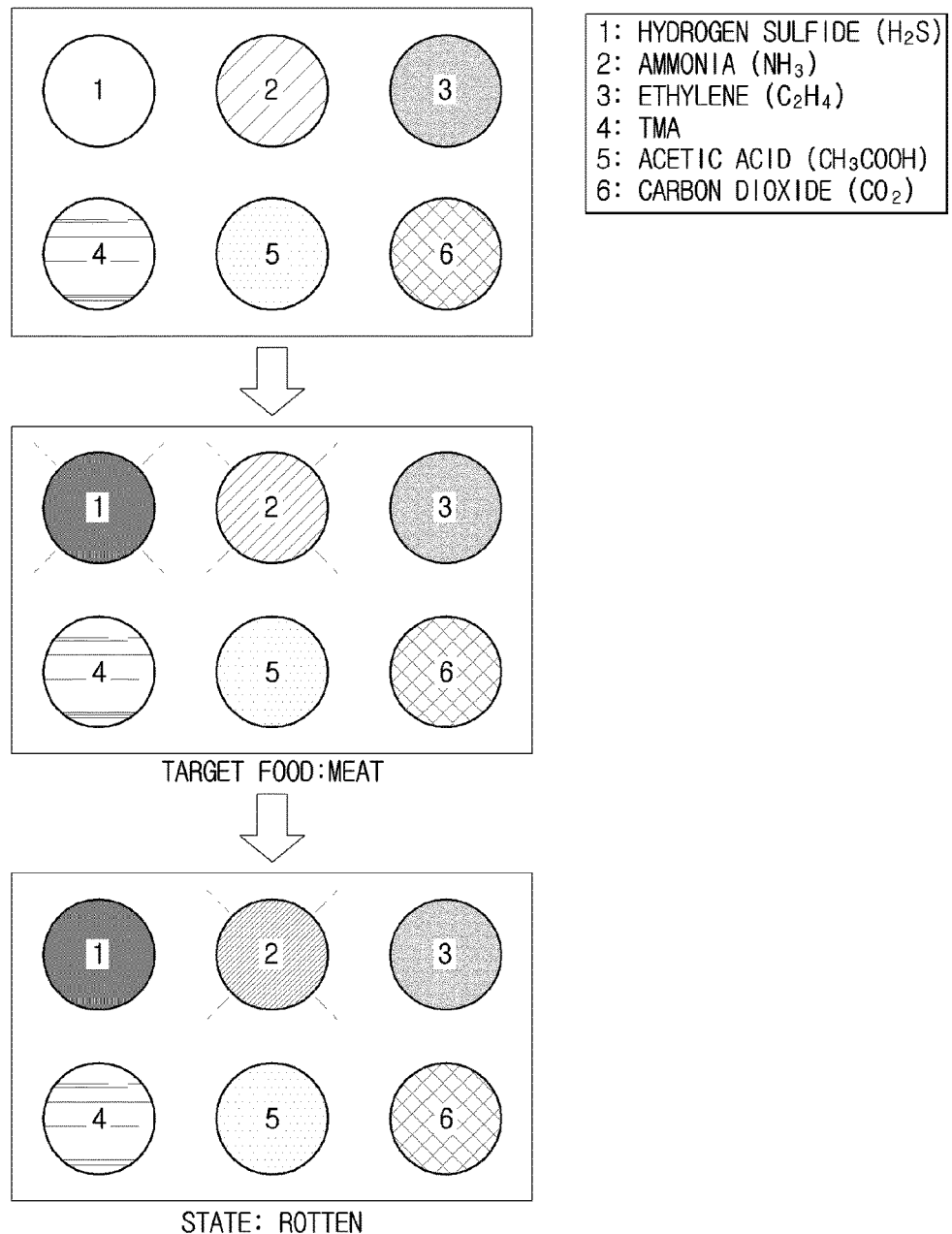

[Fig. 16]
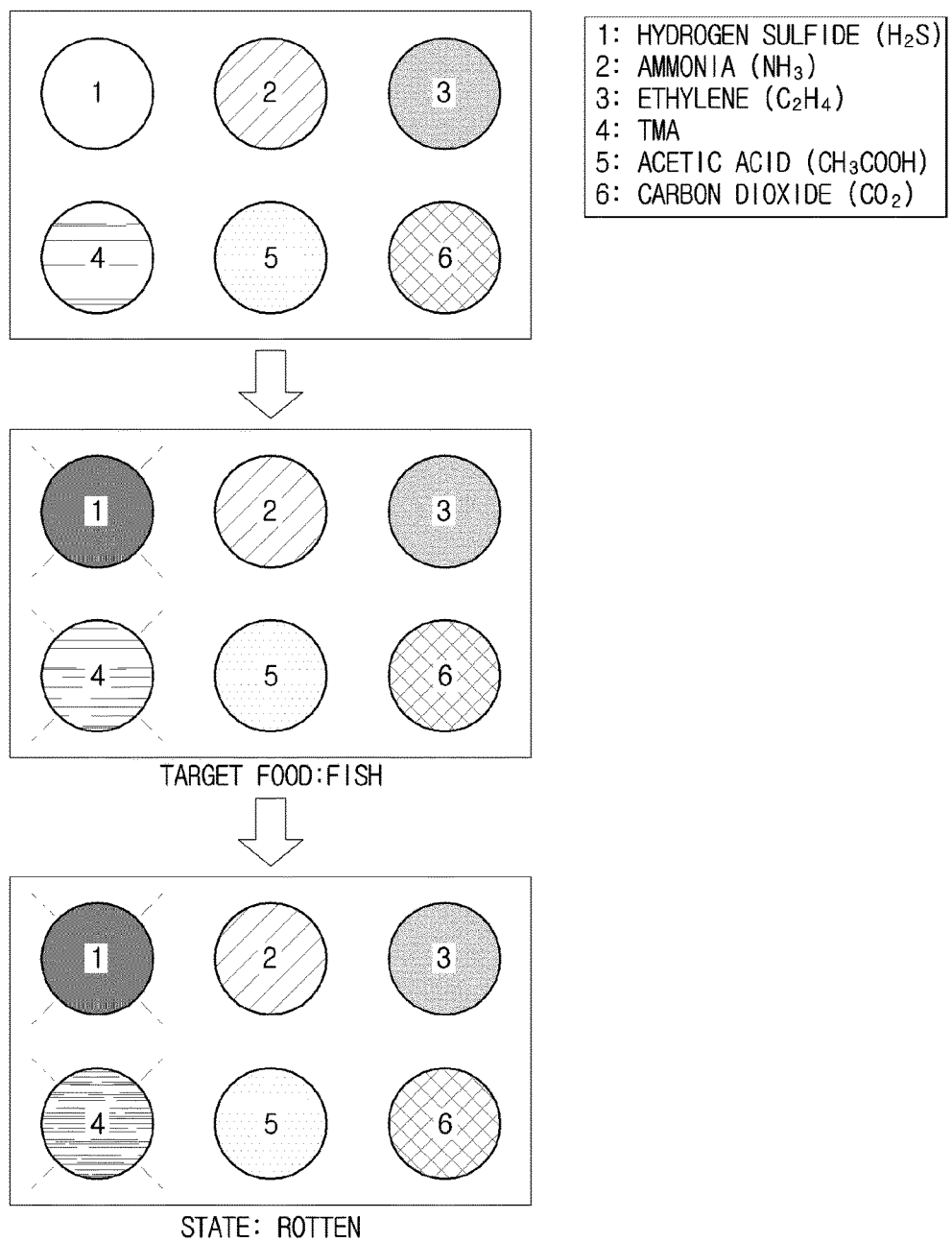

[Fig. 17]
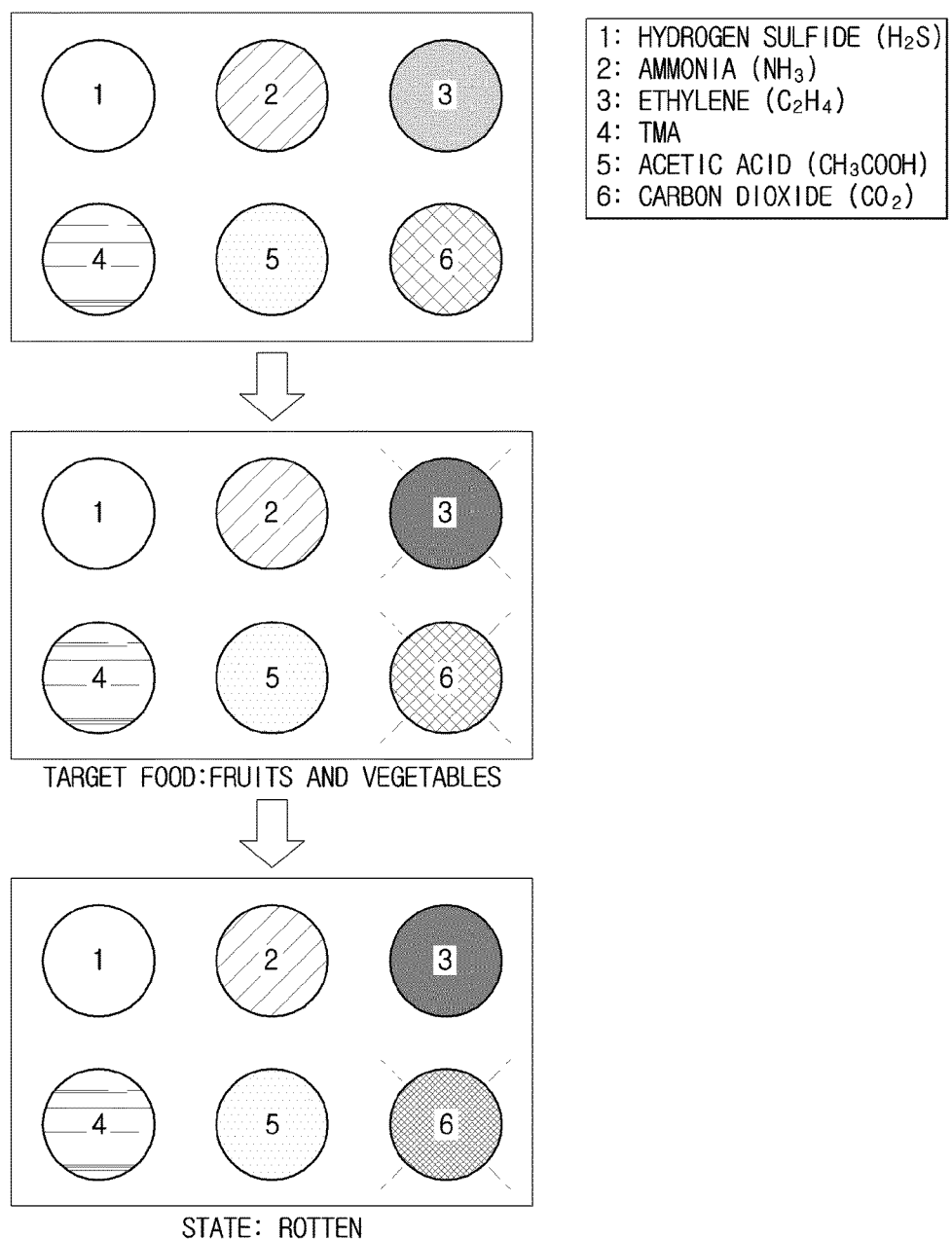

[Fig. 18]
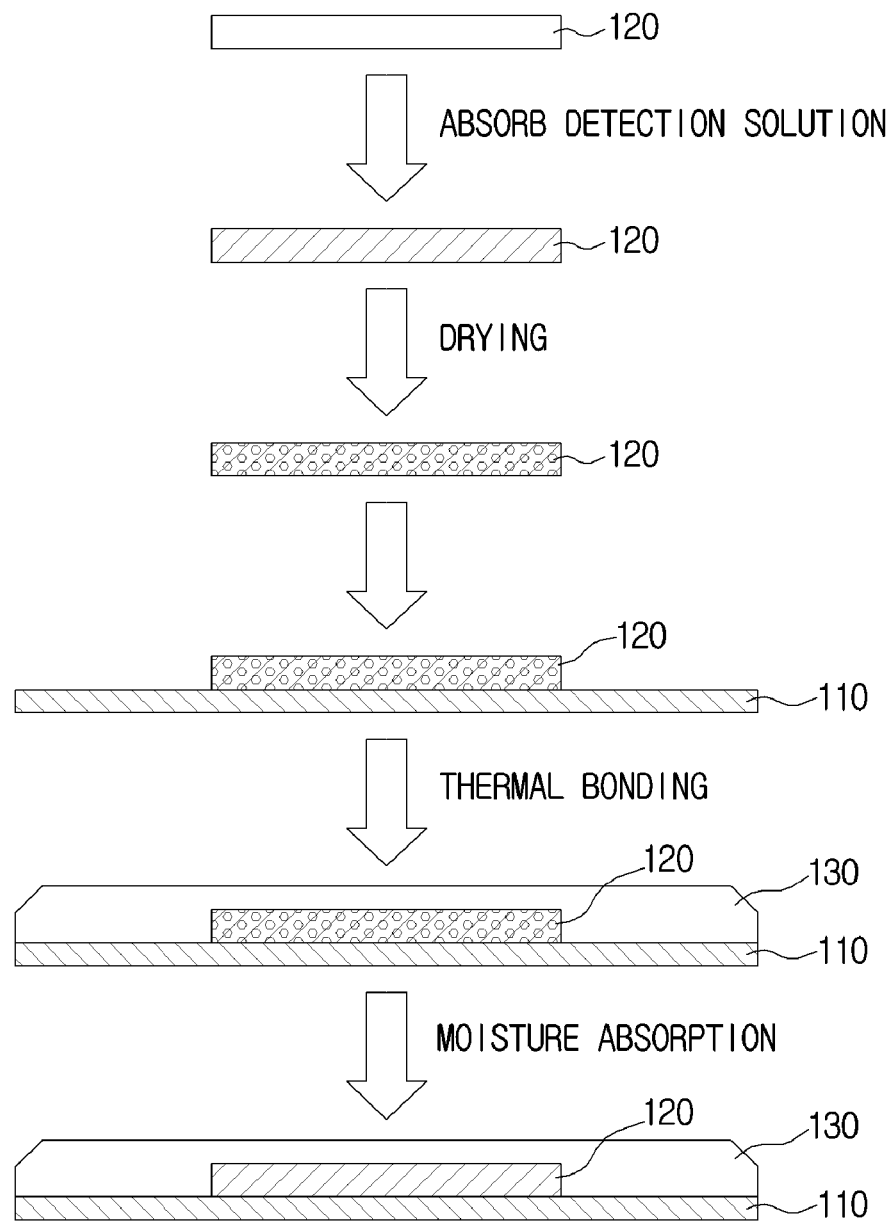

[Fig. 19]
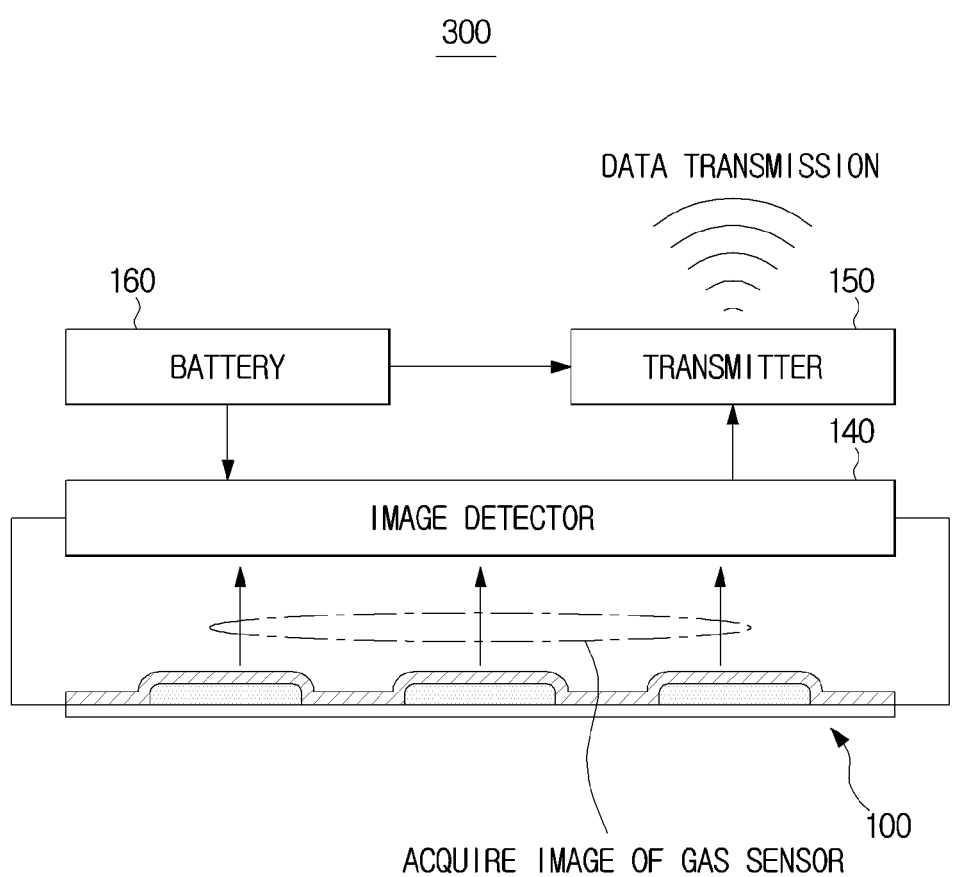

[Fig. 20]
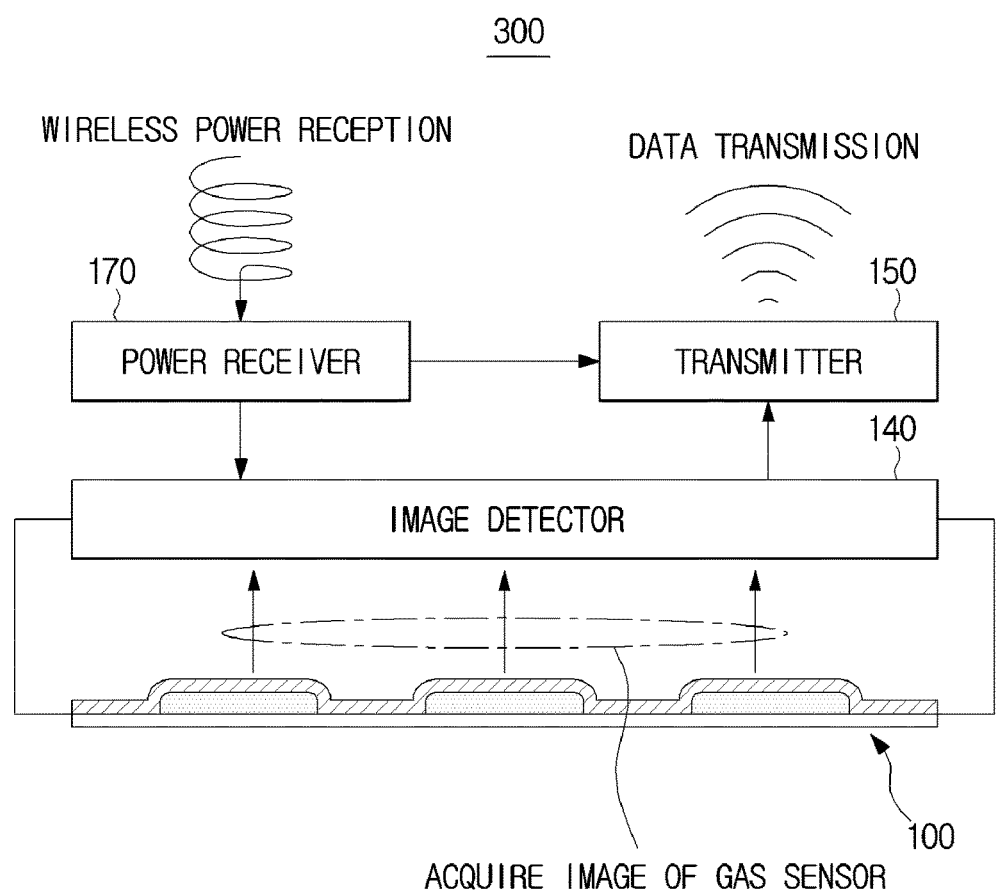

[Fig. 21]
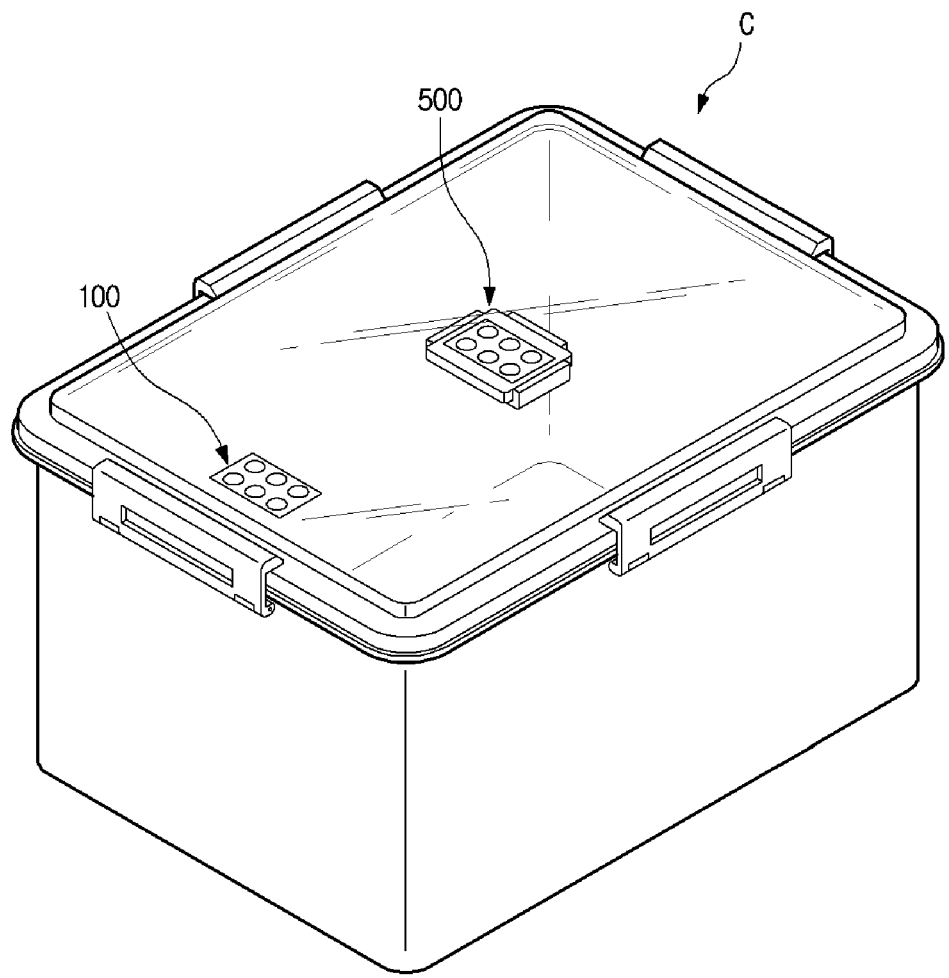

[Fig. 22]
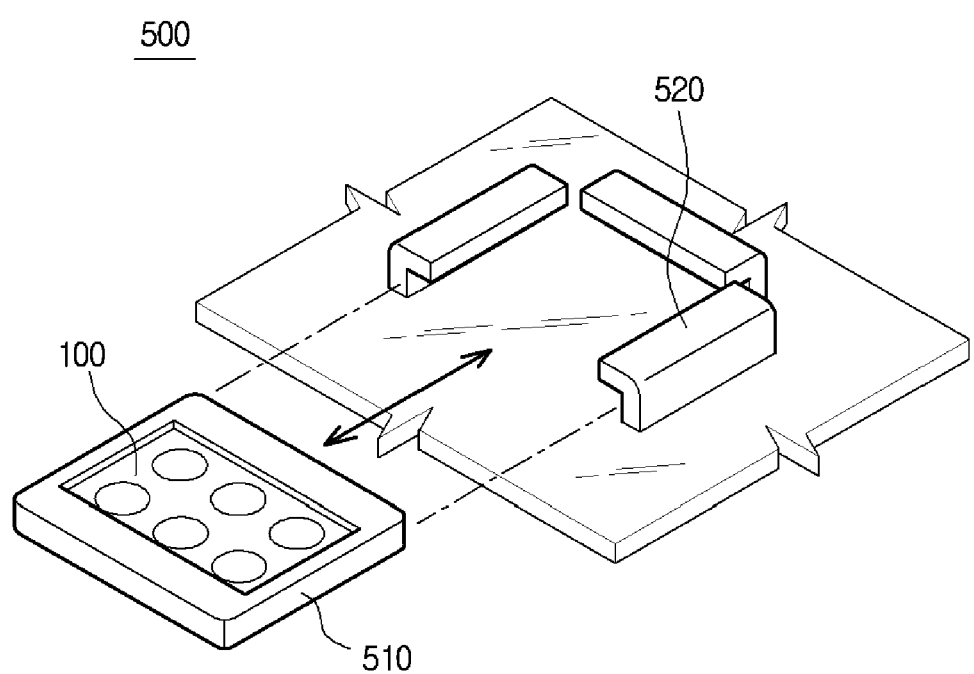

[Fig. 23]
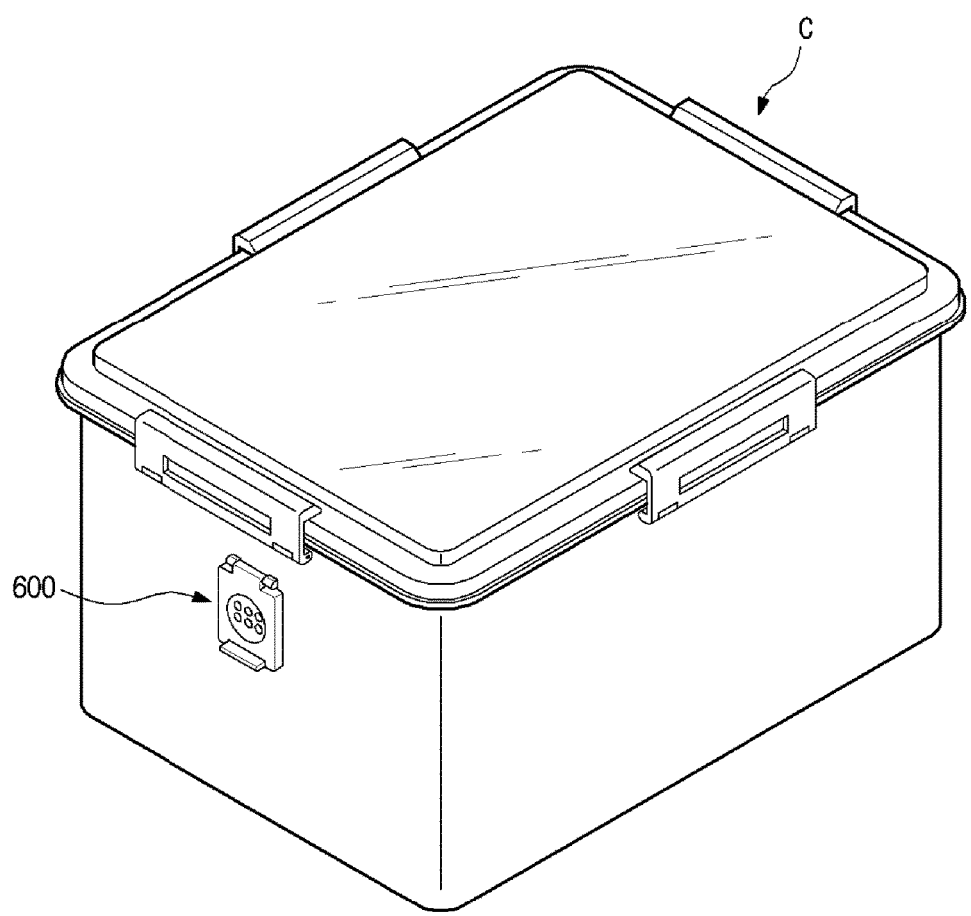

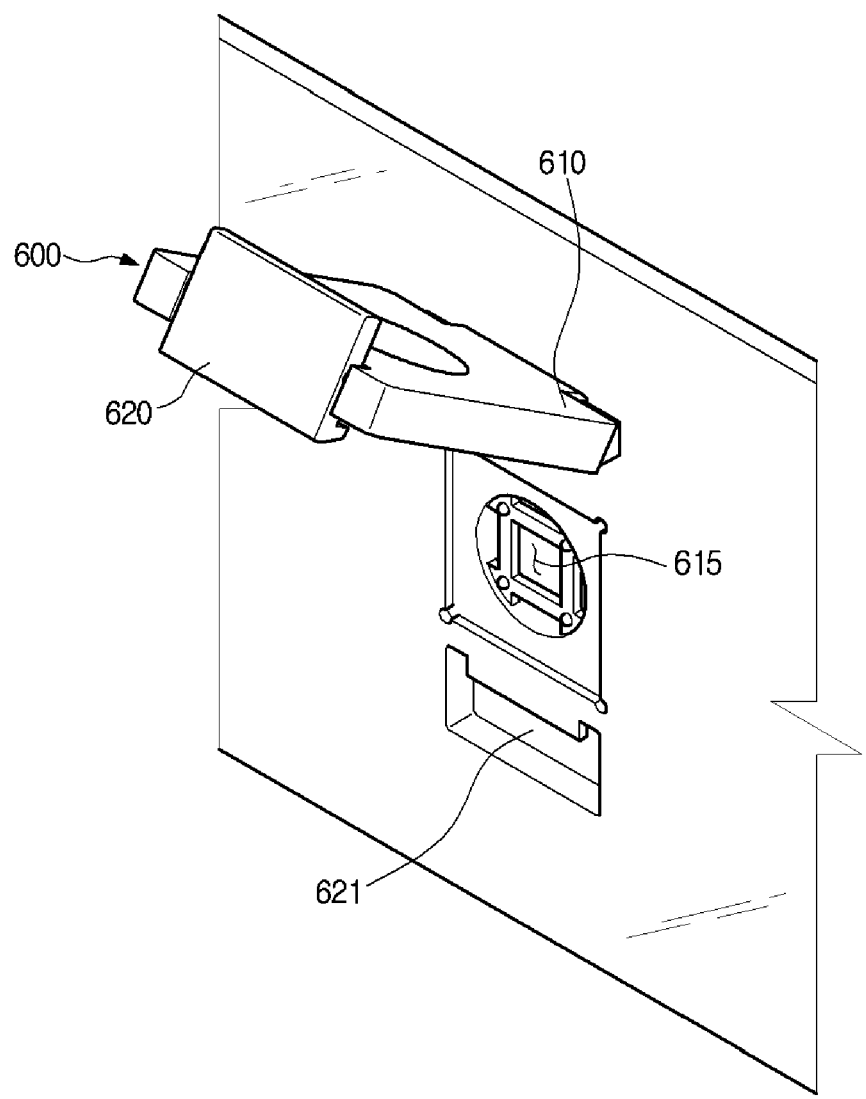
[Fig. 24]

[Fig. 25]
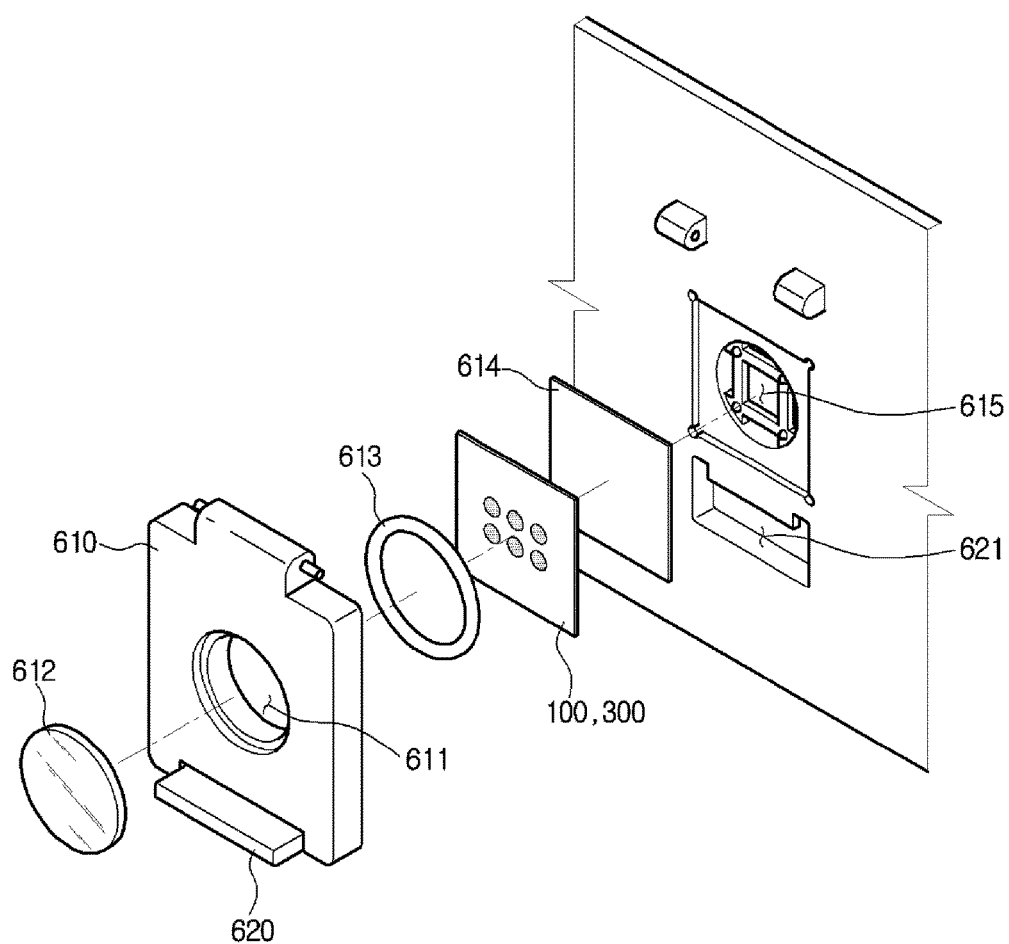

[Fig. 26]
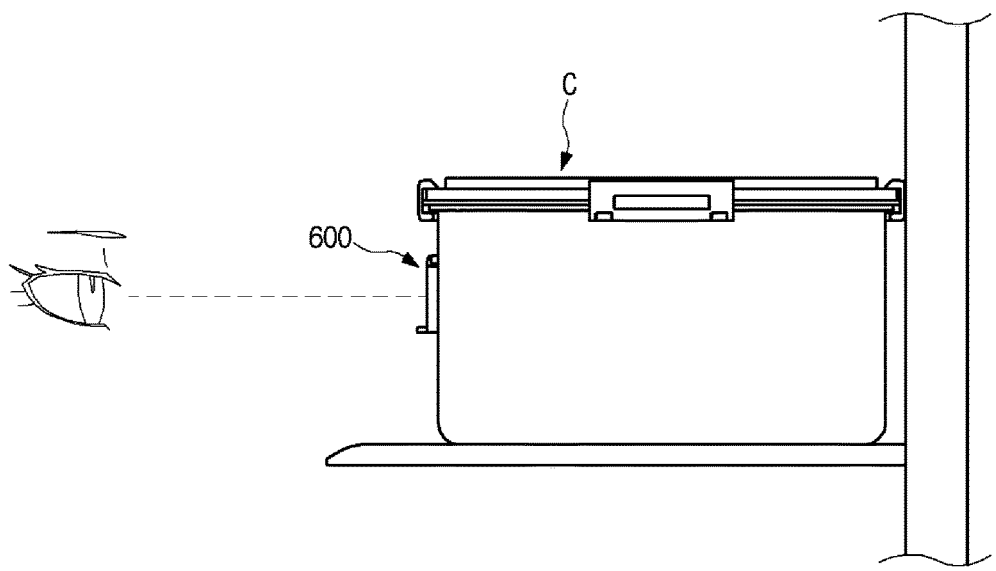
[Fig. 27]
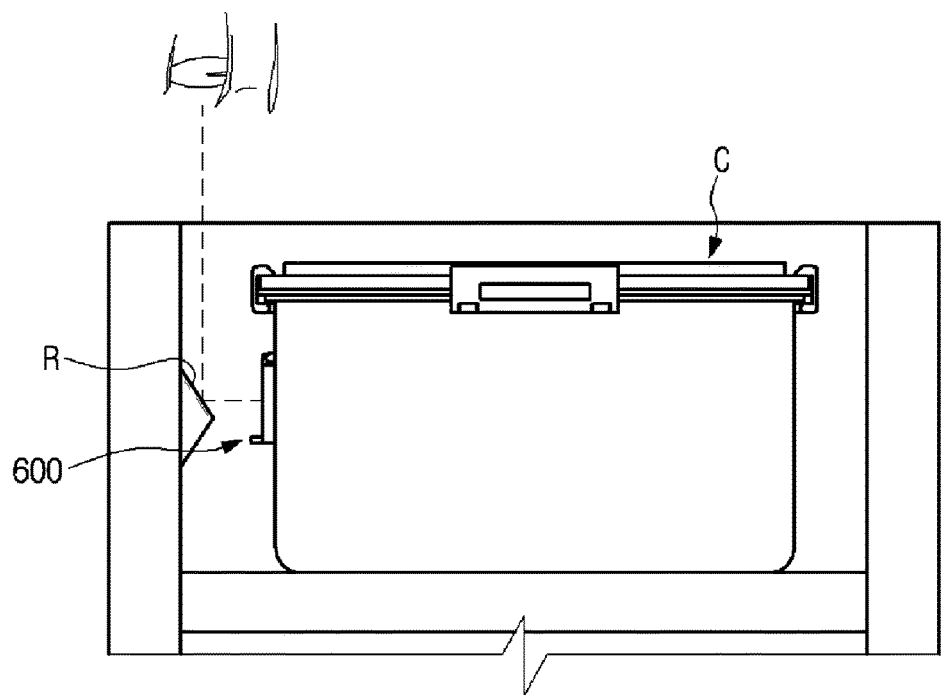

[Fig. 28]
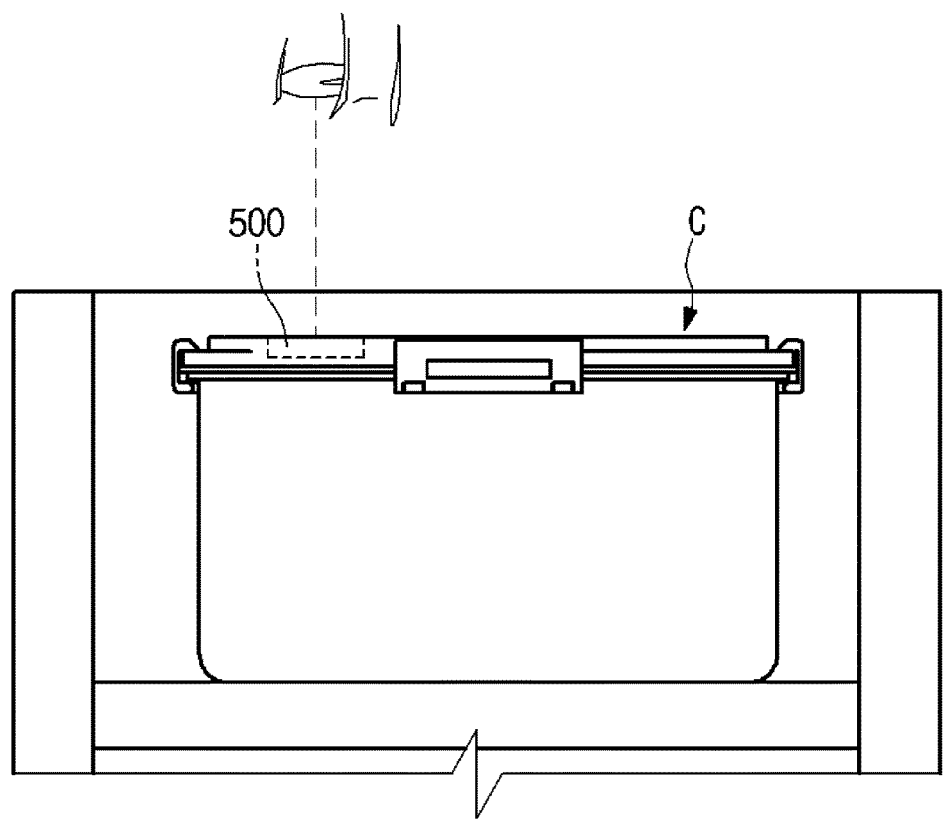

[Fig. 29]
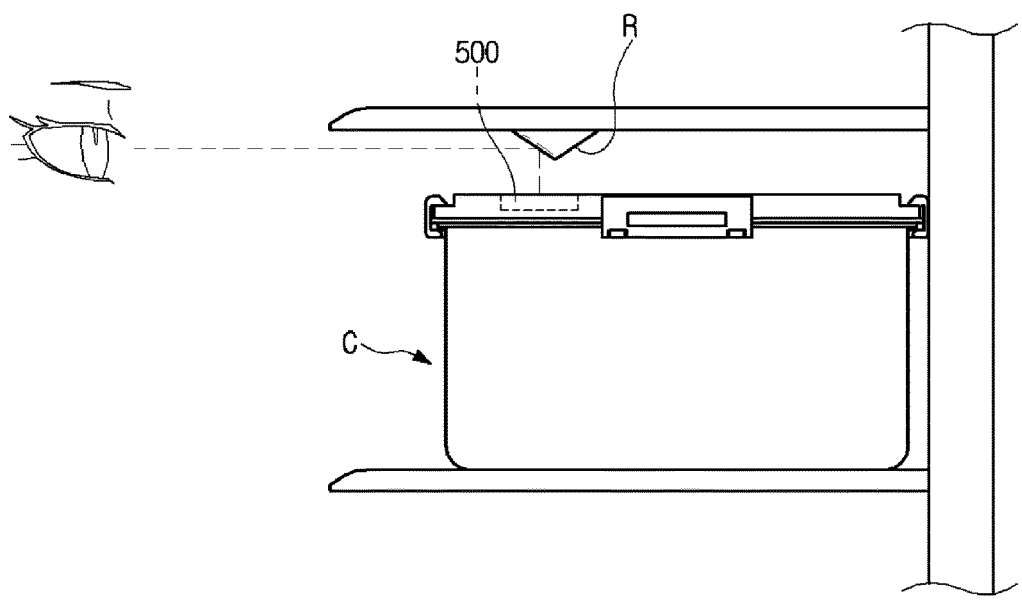
[Fig. 30]
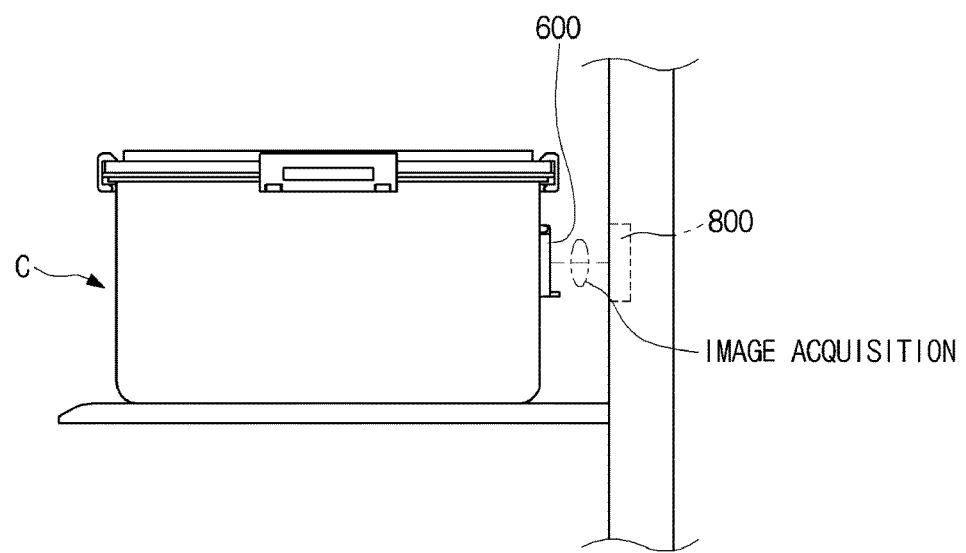

[Fig. 31]
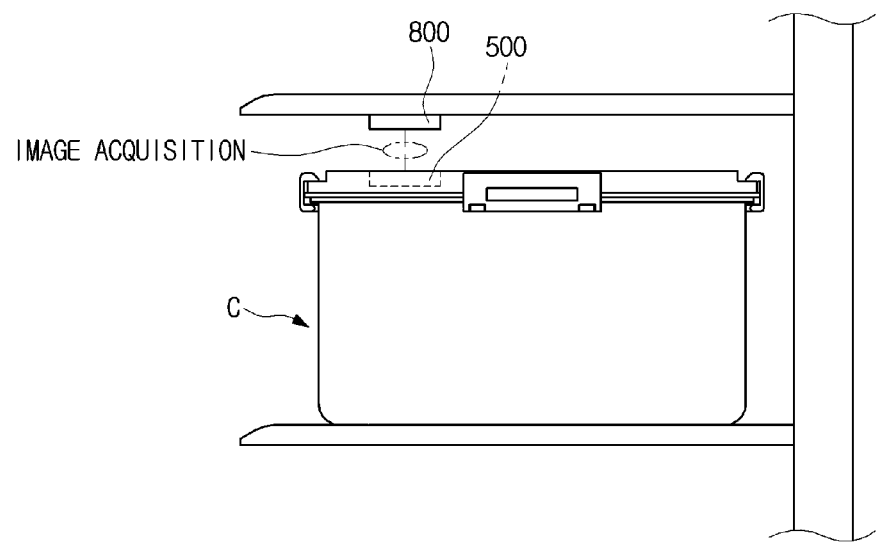

[Fig. 32]
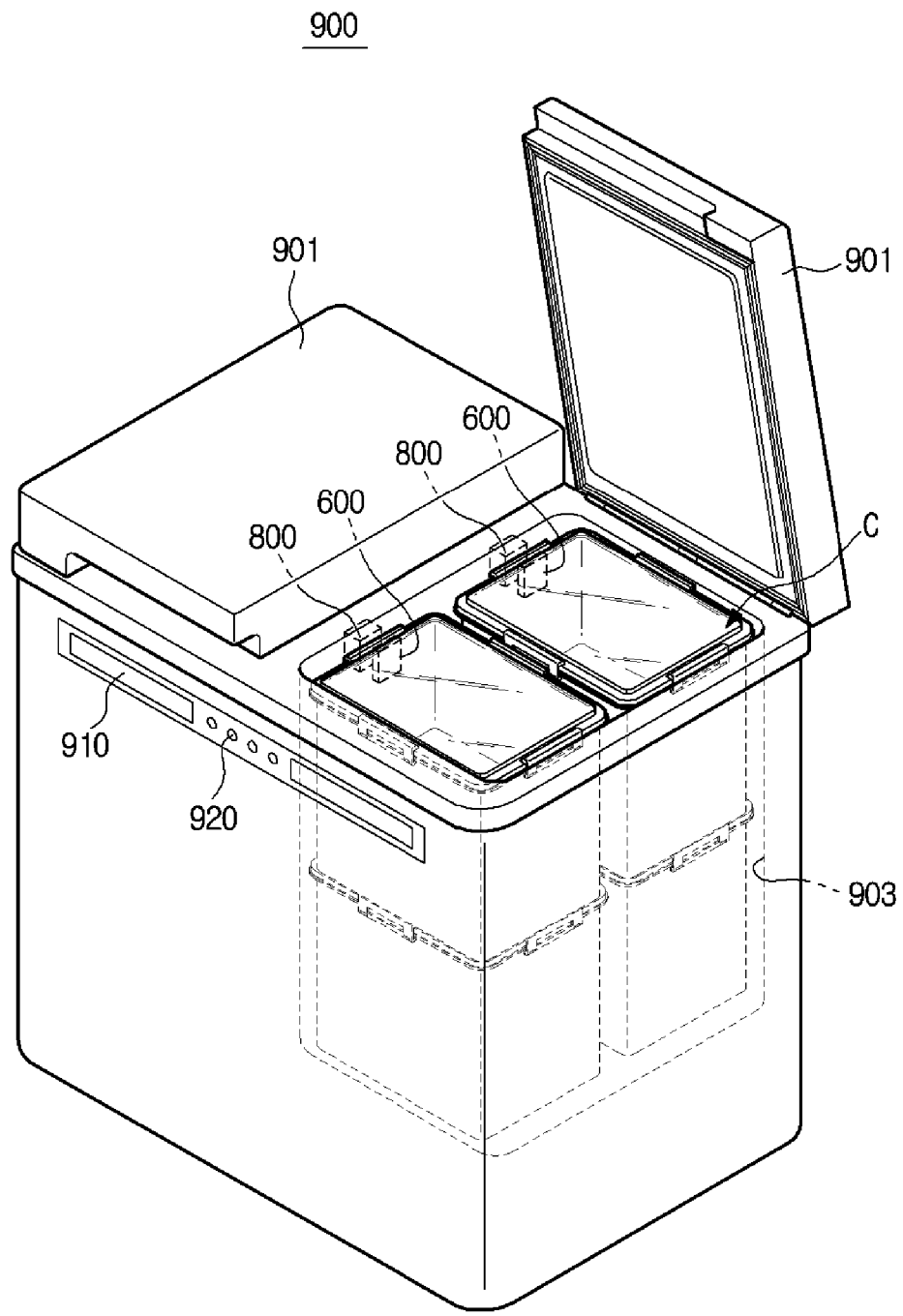

[Fig. 33]
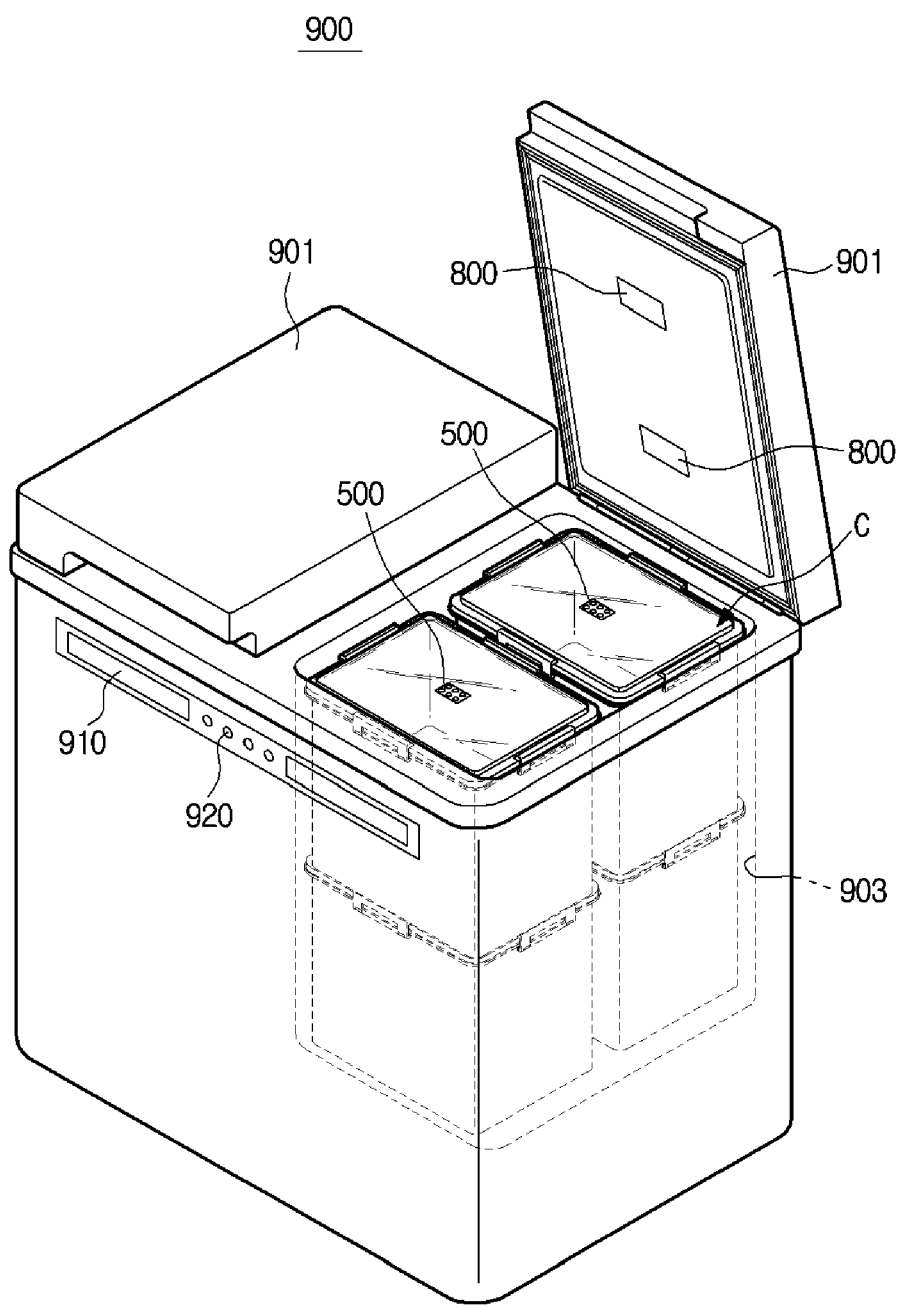

[Fig. 34]
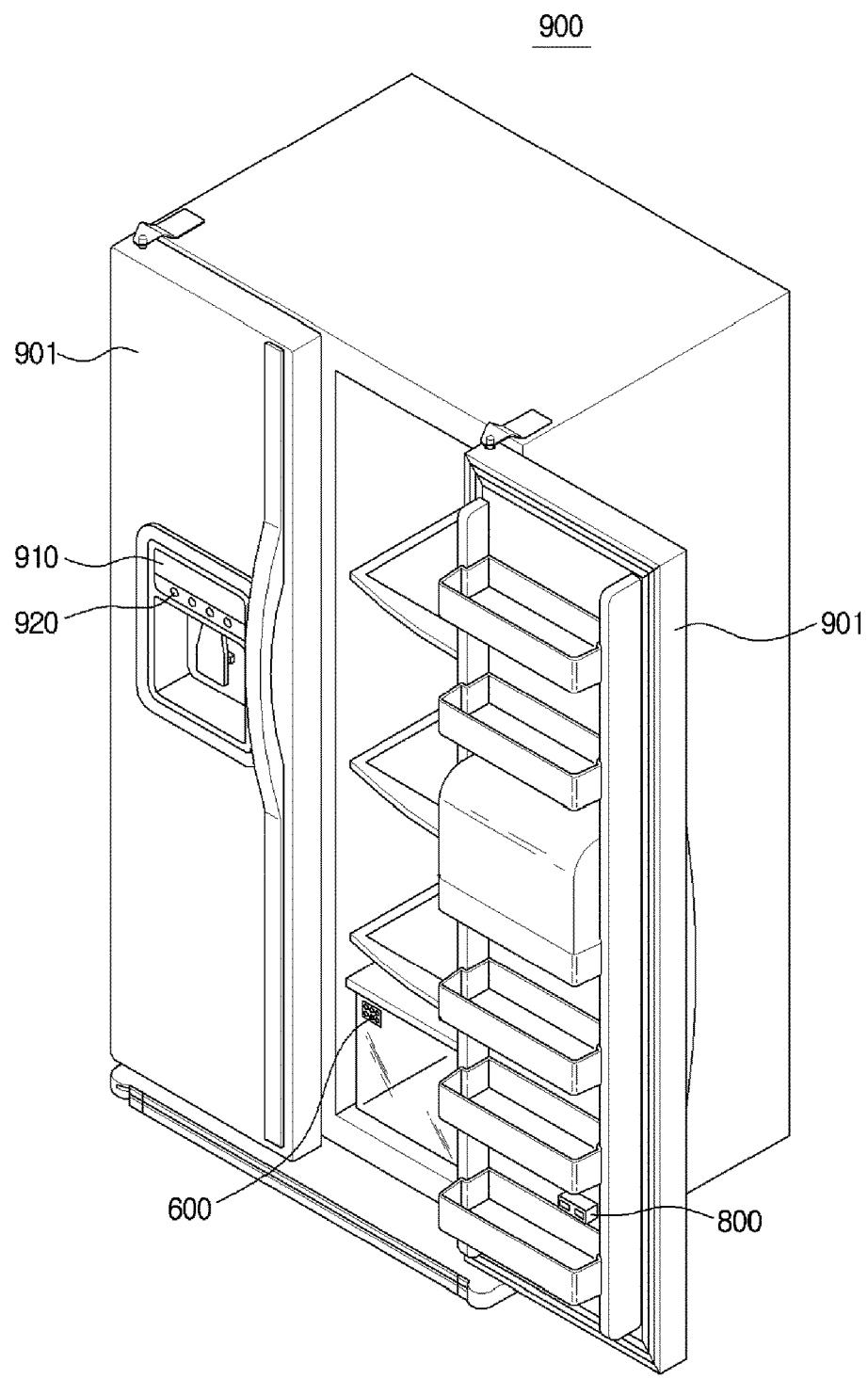

[Fig. 35]
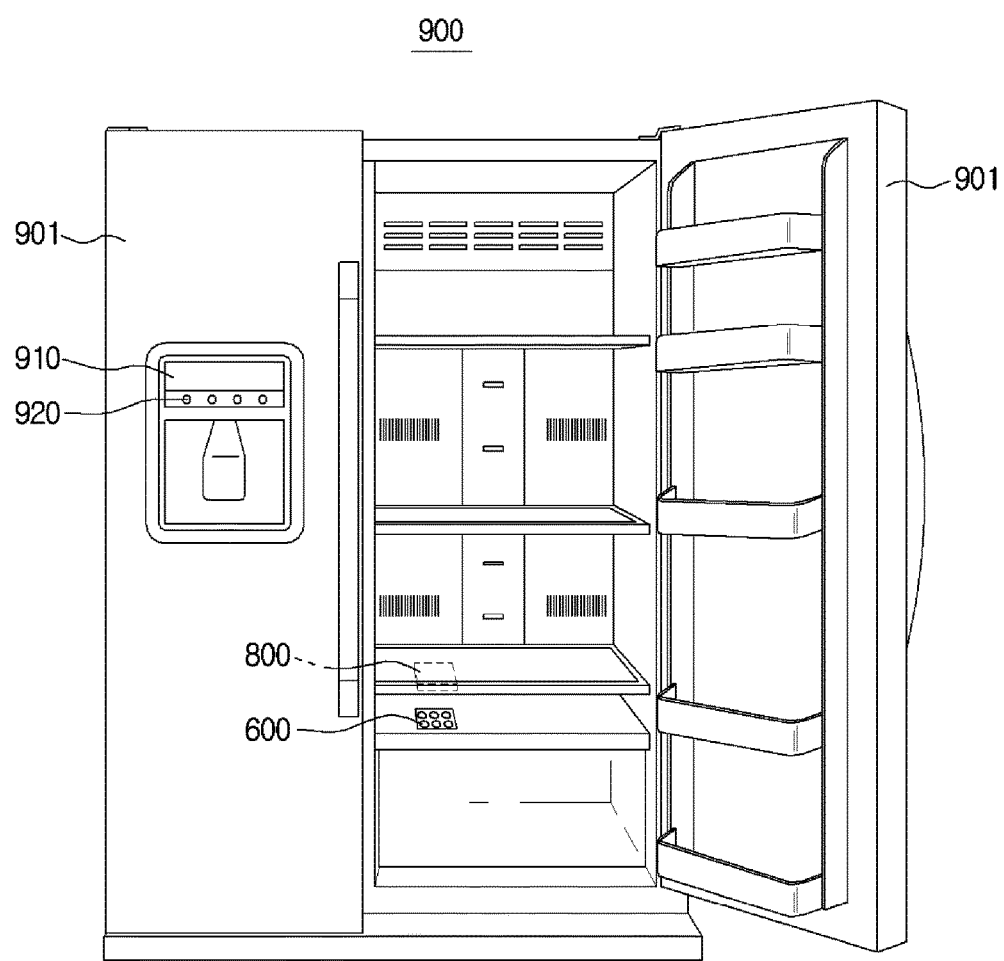

[Fig. 36a]
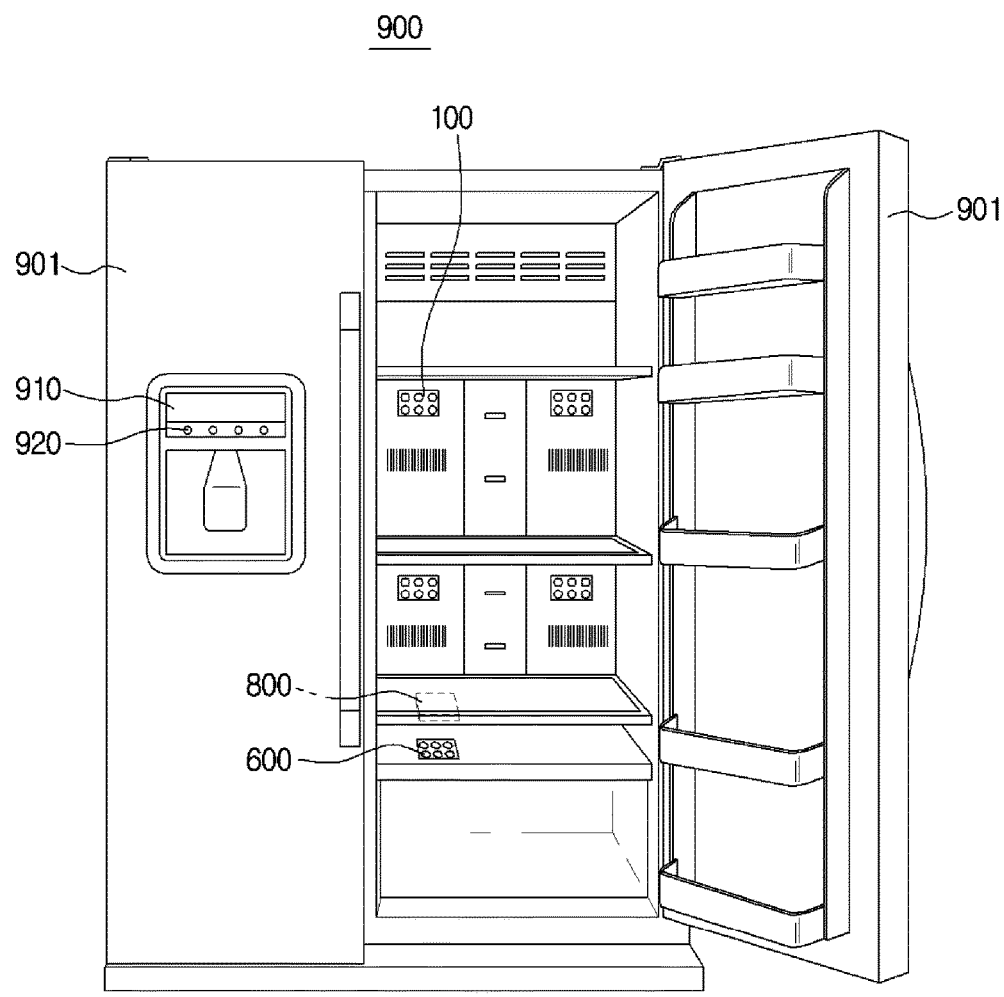

[Fig. 36b]
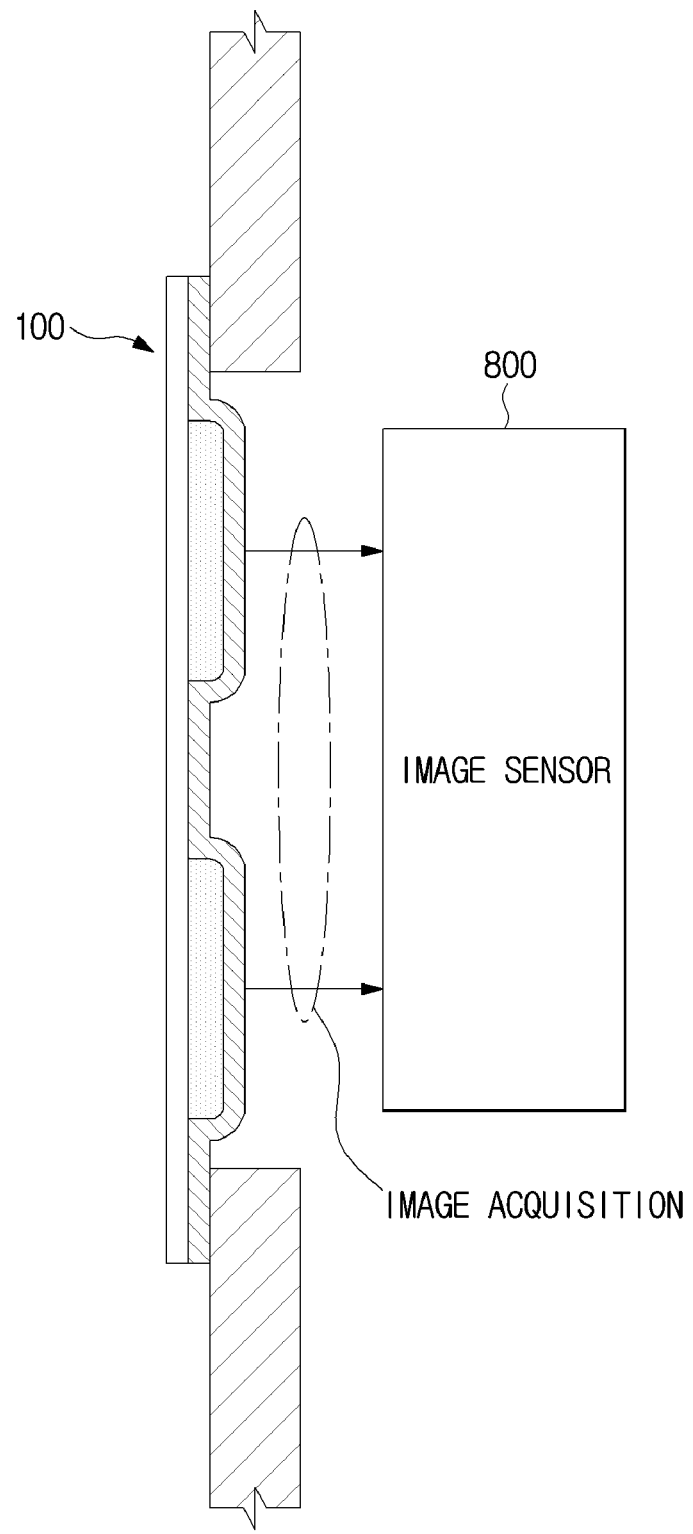

[Fig. 37]
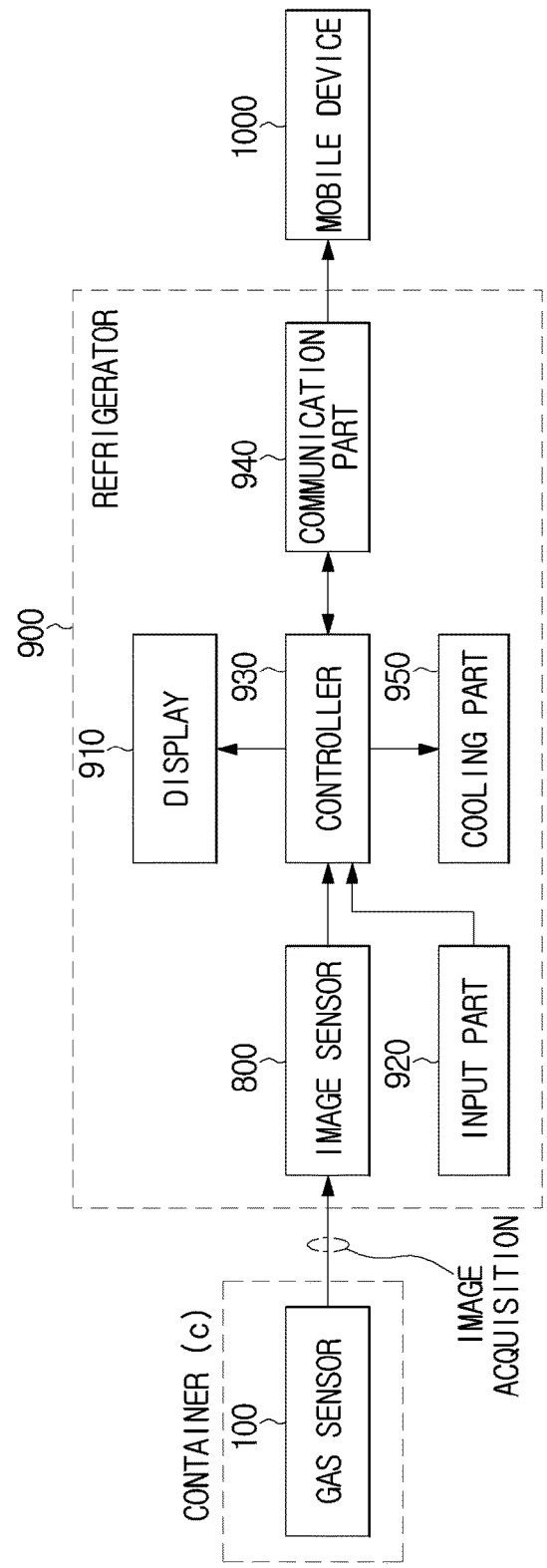

[Fig. 38]
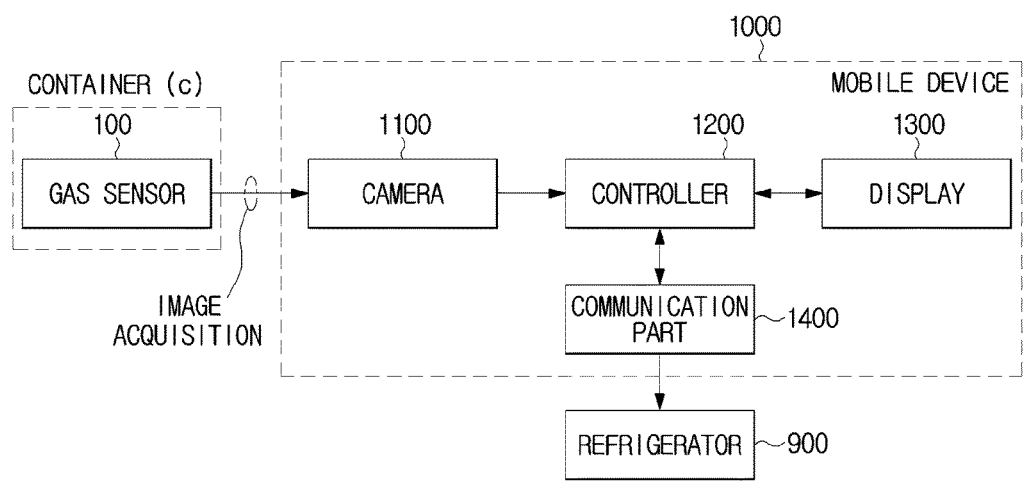

[Fig. 39]
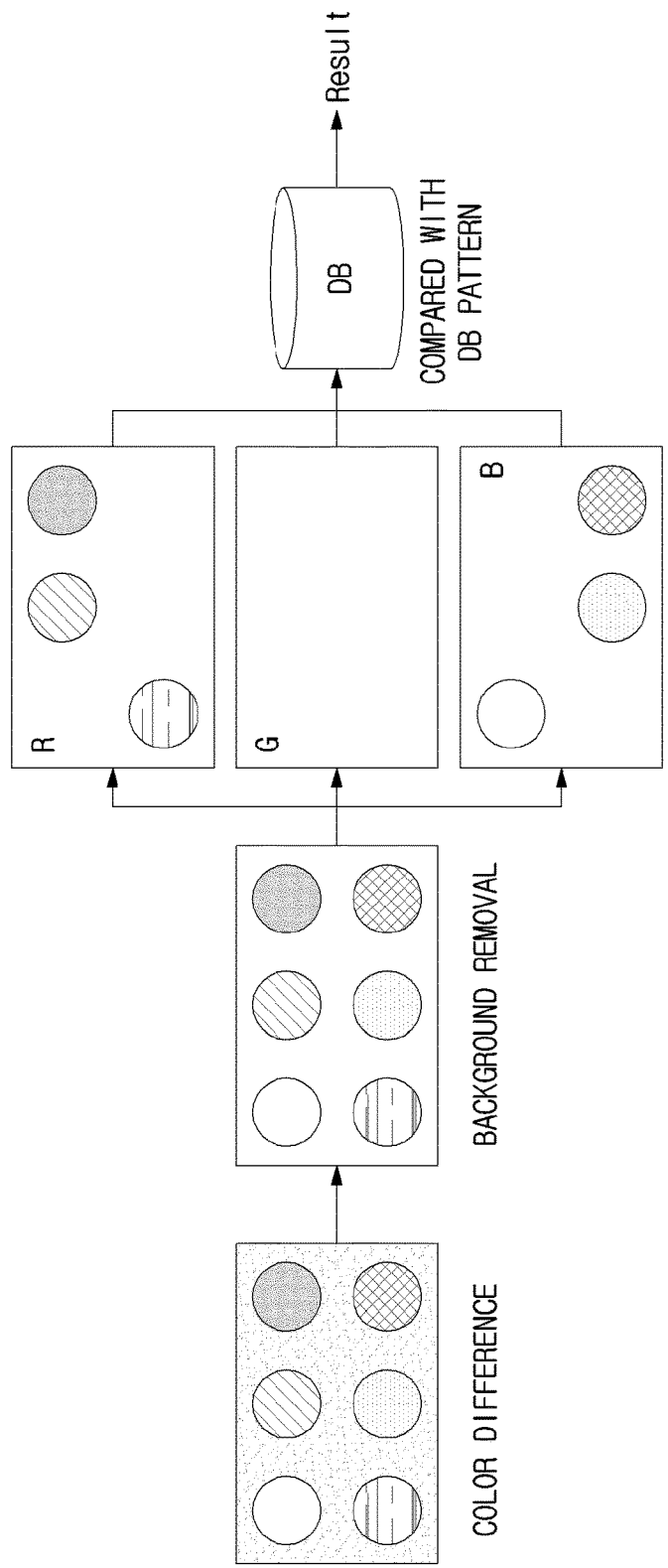

[Fig. 40]
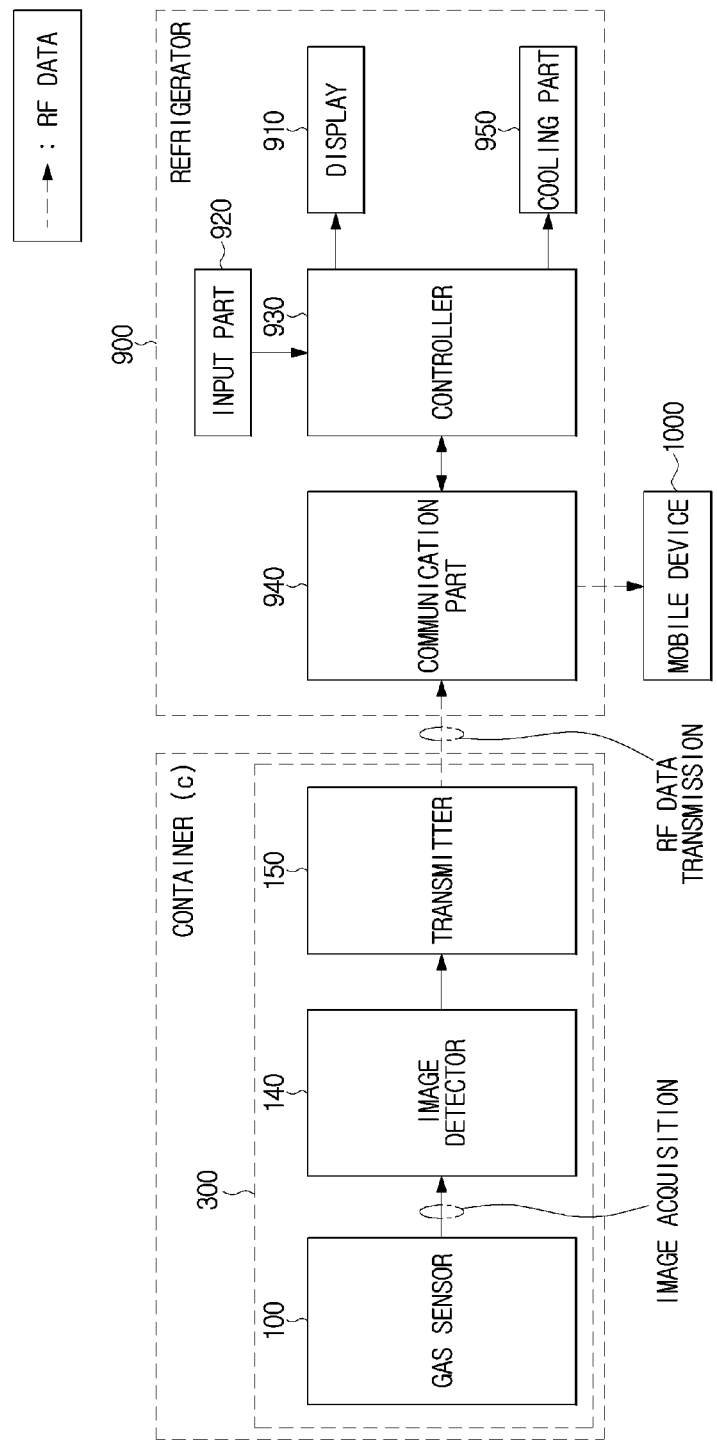

[Fig. 41]
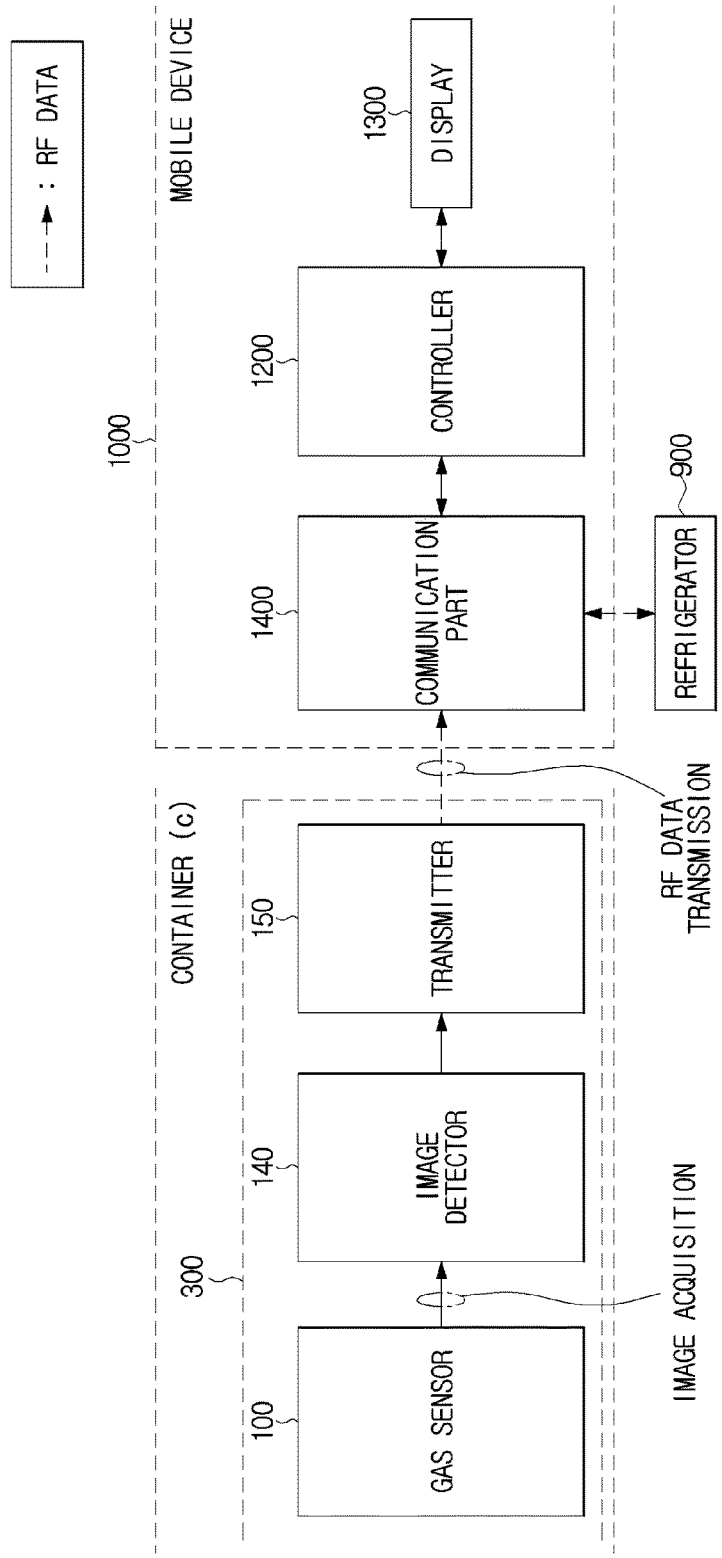

[Fig. 42]
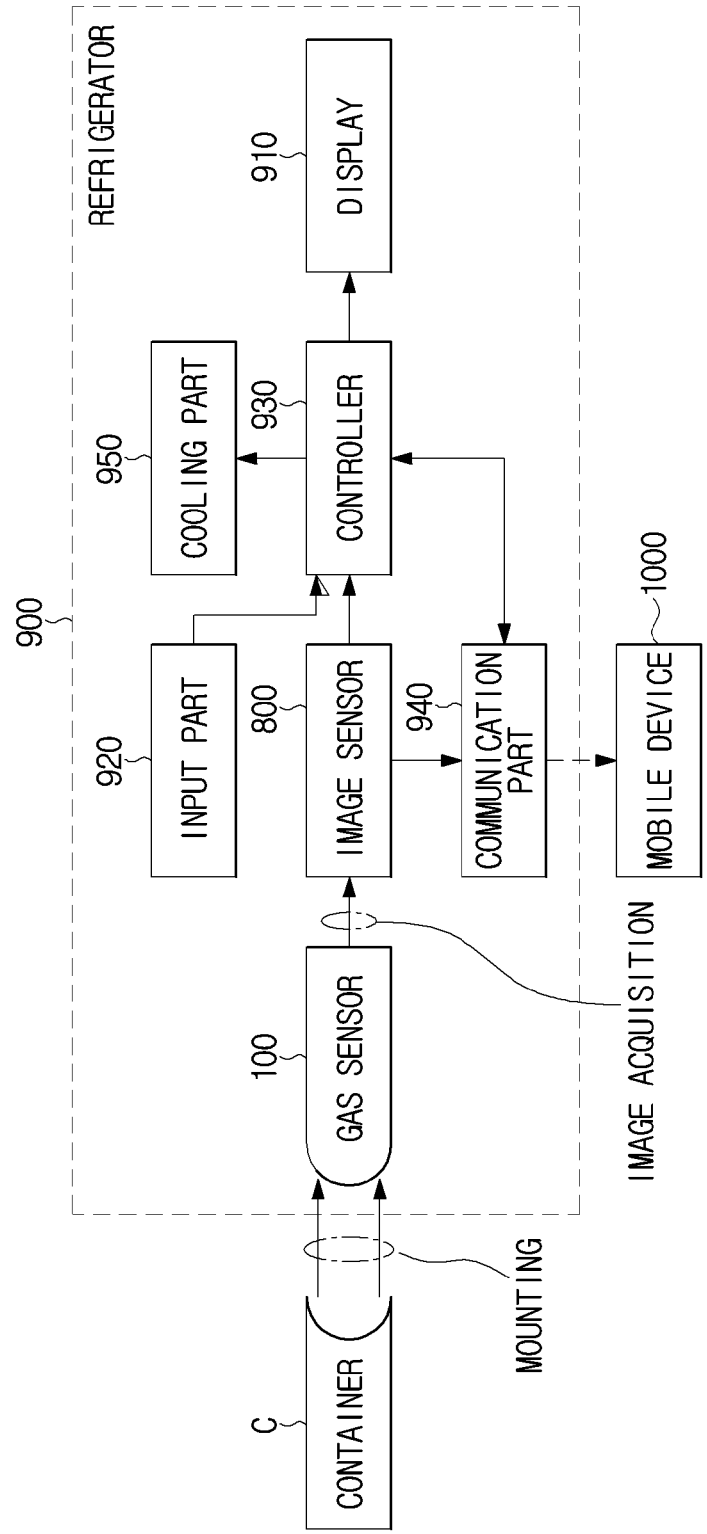

[Fig. 43]
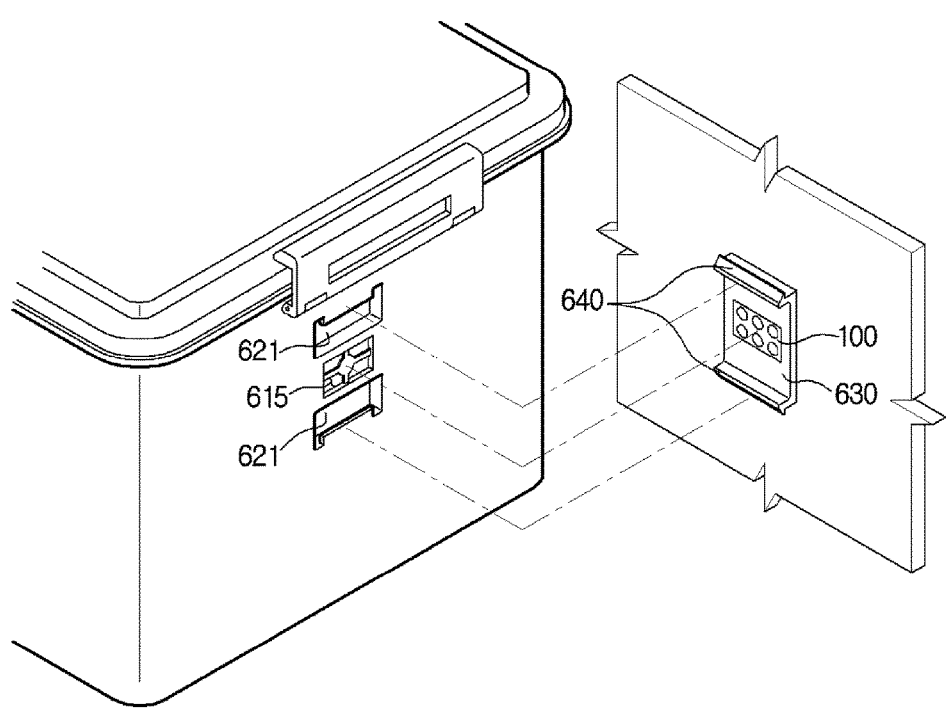

[Fig. 44]
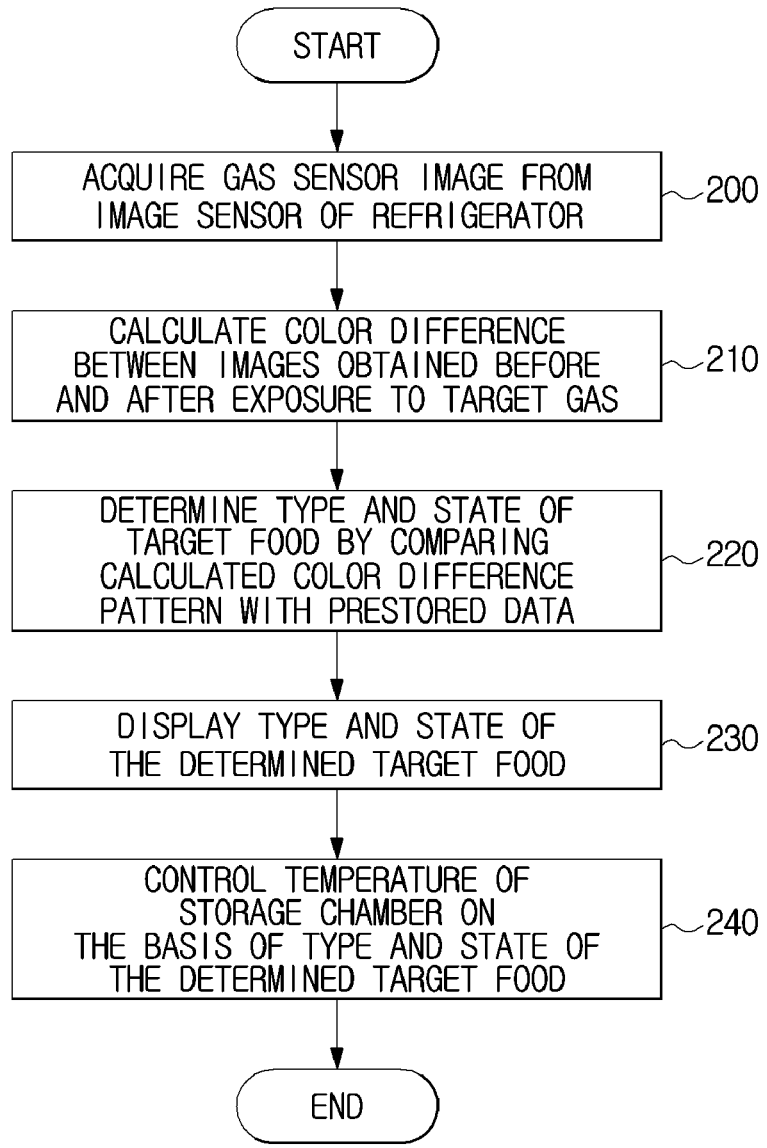

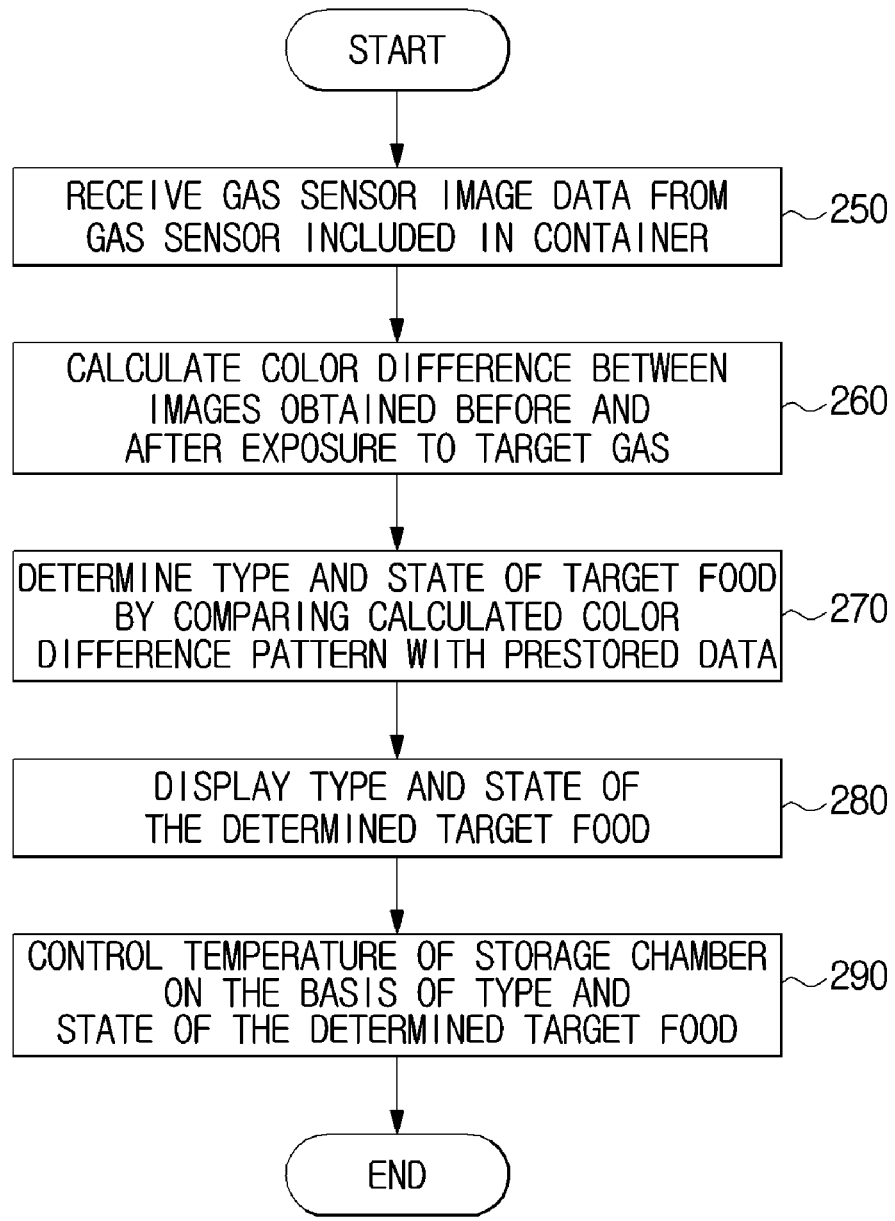
[Fig. 45]

GAS SENSOR, REFRIGERATOR INCLUDING SAME AND CONTROL METHOD THEREFOR

CROSS-REFERENCE TO RELATED APPLICATION

This application is a U.S. national stage application, which claims the benefit under 35 USC § 371 of PCT International Patent Application No. PCT/KR2015/003337, filed Apr. 2, 2015 which claims foreign priority benefit under 35 USC § 119 of Korean Patent Application No. 10-2014-0092022, filed on Jul. 21, 2014, the entire contents of which are incorporated herein by reference.

TECHNICAL FIELD

Embodiments of the present disclosure relate to a gas sensor for measuring the amount of target gas, an electronic product having the gas sensor, and a method for controlling the electronic product.

BACKGROUND ART

A gas sensor measures the density of specific gas, and is classified into a semiconductor gas sensor, a contact combustion gas sensor, and an electrochemical gas sensor, etc. From among the above-mentioned gas sensors, the semiconductor gas sensor measures the influence of resistance changed when a target material to be measured is oxidized or reduced, and the electrochemical gas sensor measures the amount of ions generated by oxidizing/reducing gas dissolved in electrolyte so that it can measure the density of gas.

Since most gas other than inert gas has a tendency of oxidation-reduction, the semiconductor gas sensor and the electrochemical gas sensor unavoidably generate crosstalk in which target gas to be measured and other gases are simultaneously measured. Therefore, there is a limitation in measurement selectivity through which specific gas can be selectively measured.

In addition, whereas the olfactory organ of a human being can sense a ppb-level gas emitting a smell, the measurement sensitivity of a conventional gas sensor is less than that of the human olfactory organ, so that the conventional gas sensor has difficulty in measuring gas of a ppm level or lower.

DISCLOSURE

Technical Problem

An object of the present disclosure is to provide a gas sensor including a plurality of detectors discolored by reacting with different predetermined target gases, such that the gas sensor can independently measure the amount of each target gas.

Another object of the present disclosure is to provide a refrigerator for deciding a category and a state of target food contained in a container by sensing a color change of a gas sensor mounted to the container including the target food, and a method for controlling the gas sensor.

Technical Solution

The objects of the present disclosure can be achieved by providing a gas sensor for detecting a plurality of target gases including: a base; and a plurality of detectors provided at the base, and configured to respectively detect different target gases, wherein each of the plurality of detectors is discolored by reacting with each predetermined target gas.

The detector may include at least one pH indicator which is discolored in response to pH variation generated by reacting with a predetermined target gas.

The detector may include a hydrophilic membrane having a detection solution.

The detection solution may include at least one pH indicator which is discolored in response to pH variation generated by reacting with a predetermined target gas.

The detection solution may include at least one selected from among a group which includes glycerin, ethylene glycol, polyethylene glycol, calcium chloride, and sodium chloride.

The hydrophilic membrane may include at least one selected from among a group which includes cellulose ester, glass fiber, cellulose acetate, cellulose fiber, litmus paper, Korean traditional paper, and filter paper.

The base may include a hydrophobic membrane needed for gas permeation.

The base may include at least one selected from among a group which includes polytetrafluoroethylene, thermoplastic polyurethane, polyethylene, low density polyethylene, linear low density polyethylene, high density polyethylene, and Tyvek.

The gas sensor may further include: a transparent membrane attached to the plurality of detectors, configured to prevent gas permeation.

The target gas may include gas generated from a ripening process of food.

The target gas may include hydrogen sulfide, ammonia, ethylene, trimethylamine (TMA), acetic acid, and carbon dioxide ($CO_2$).

The plurality of detectors may be arranged in a two-dimensional (2D) array shape over the base.

The gas sensor may further include: an image detector configured to detect colors of the plurality of detectors; and a transmitter configured to output data regarding each color detected by the image detector to an external part.

The gas sensor may further include: a battery configured to provide a power source to the image detector and the transmitter.

The gas sensor may further include: a wireless power receiver configured to provide a power source to the image detector and the transmitter.

In another aspect of the present disclosure, an electronic product includes: the gas sensor of claim 1.

The electronic product may further include: an image sensor configured to acquire an image of the gas sensor.

The electronic product may further include: a controller configured to identify a target object on the basis of the gas sensor image obtained from the image sensor, and determine a state of the target object.

The controller may be configured to prestore data regarding discoloration of the plurality of detectors of the gas sensor and data regarding a type and state of the target object according to degree of the discoloration.

The controller may determine a difference between a gas sensor color obtained before exposure to target gas and a gas sensor color obtained after exposure to the target gas using the image obtained from the image sensor, and may determine a type and state of the target object on the basis of the determined color difference using the prestored data.

The electronic product may further include: a display configured to display information regarding a type or state of a target object determined on the basis of the gas sensor image acquired from the image sensor.

The electronic product may further include a refrigerator, wherein the controller controls a temperature of the refrigerator according to the determined target object state.

The gas sensor and the image sensor may be provided in each storage chamber of the refrigerator. The controller may determine a type and state of the target object located in each storage chamber on the basis of the gas sensor image acquired from the image sensor provided in each storage chamber, and may control a temperature of each storage chamber according to the determined target object state.

In still another aspect of the present disclosure, a refrigerator includes: a storage chamber; and an image sensor configured to detect a color of a gas sensor of a container included in the storage chamber.

The refrigerator may further include: a controller configured to identify a target object included in the container on the basis of a gas sensor image acquired from the image sensor, and determine a state of the target object.

The controller may prestore data regarding discoloration of a plurality of detectors of the gas sensor and data regarding a type and state of the target object based on the discoloration.

The controller may determine a difference between a gas sensor color obtained before exposure to target gas and a gas sensor color obtained after exposure to the target gas using the image obtained from the image sensor, and may determine a type and state of the target object on the basis of the determined color difference using the prestored data.

The controller may control a temperature of the storage chamber according to the determined target object state.

The refrigerator may further include: a display configured to display information regarding a type or state of a target object determined on the basis of the gas sensor image acquired from the image sensor.

In still another aspect of the present disclosure, a refrigerator includes: a storage chamber; and a controller configured to identify a target object included in a container on the basis of a gas sensor image outputted from a gas sensor of the container included in the storage chamber, and determine a state of the target object.

The controller may be configured to prestore data regarding discoloration of a plurality of detectors of the gas sensor and data regarding a type and state of the target object based on the discoloration.

The controller may determine a difference between a gas sensor color obtained before exposure to target gas and a gas sensor color obtained after exposure to the target gas using the gas sensor image outputted from the gas sensor, and may determine a type and state of the target object on the basis of the determined color difference using the prestored data.

The controller may control a temperature of the storage chamber according to the determined target object state.

The refrigerator may further include: a display configured to display information regarding the type or state of the target object determined on the basis of the gas sensor image.

The refrigerator may further include: a receiver configured to receive data wirelessly transmitted from the gas sensor.

In still another aspect of the present disclosure, a method for controlling a refrigerator includes: determining discoloration of a gas sensor provided in a container included in a storage chamber; and displaying a state of a target object corresponding to the discoloration of the gas sensor.

The determining the discoloration of the gas sensor may include: acquiring an image of the gas sensor including a plurality of detectors; and determining a difference between a color of each detector, obtained before exposure to target gas and a color of each detector, obtained after exposure to the target gas, using the acquired image of the gas sensor.

The method may further include: determining a type and state of the target object on the basis of discoloration of the target object.

The determining the type and state of the target object may include: determining the type and state of the target object on the basis of the discoloration of the gas sensor, not only using data regarding discoloration of a plurality of detectors of a prestored gas sensor but also using data regarding the type and state of the target object based on the discoloration.

The displaying the state of the target object may include: displaying a type and state of the target object determined on the basis of the discoloration of the gas sensor.

The method may further include: controlling a temperature of the storage chamber on the basis of the state of the target object determined based on the discoloration of the gas sensor.

In still another aspect of the present disclosure, a method for controlling a refrigerator includes: receiving data regarding discoloration of a gas sensor from the gas sensor of a container included in a storage chamber; and displaying a state of a target object corresponding to the discoloration of the gas sensor according to the received data.

The method may further include: determining a difference between a color of each detector, obtained before exposure to target gas and a color of each detector, obtained after exposure to the target gas, on the basis of the received data.

The method may further include: determining a type and state of a target object on the basis of the discoloration of the target object according to the received data.

The determining the type and state of the target object may include: determining the type and state of the target object on the basis of the discoloration of the gas sensor based on the received data, not only using data regarding discoloration of a plurality of detectors of a prestored gas sensor but also using data regarding the type and state of the target object based on the discoloration.

The displaying the state of the target object may include: displaying a type and state of the target object determined on the basis of the discoloration of the gas sensor.

The method may further include: controlling a temperature of the storage chamber on the basis of the state of the target object determined based on the discoloration of the gas sensor.

In still another aspect of the present disclosure, a gas detection container includes: a container, at least one surface of which includes a hole; and an instrument part which includes a gas sensor for detecting a target gas discharged through the hole, and is installed in the hole.

The instrument part may include the gas sensor at a hole through which the gas sensor is observed from an external viewpoint.

The instrument part may be configured to cover the hole in which the gas sensor is installed.

Advantageous Effects

As is apparent from the above description, the gas sensor according to the embodiments of the present disclosure can independently detect different target gases under the condition that various high-density gases are present.

The gas sensor according to the embodiments can independently detect not only a distinctive gas capable of identifying various target foods but also various gases emitted from a ripening process of each target food, and can allow a user to visually recognize a discolored gas sensor, so that the user can intuitively recognize a category and state of each target food.

The refrigerator according to the embodiments can decide a category and state of a target food present in a container by measuring a color change of the gas sensor provided in the container, thereby controlling a temperature of a storage chamber including the container.

DESCRIPTION OF DRAWINGS

The accompanying drawings, which are included to provide a further understanding of the invention, illustrate embodiments of the invention and together with the description serve to explain the principle of the invention.

FIG. 1 is a diagram illustrating categories and density of gas generated in response to a ripening degree of kimchi.

FIG. 2 is a diagram illustrating categories and density of gas generated in response to a ripening degree of meat.

FIG. 3 is a diagram illustrating categories and density of gas generated in response to a ripening degree of fruits and vegetables.

FIG. 4 is a graph illustrating density of carbon dioxide ($CO_2$) according to a ripening period of fruits and vegetables.

FIGS. 5 to 7 are diagrams illustrating a gas sensor according to a first embodiment of the present disclosure.

FIGS. 8 to 10 are conceptual diagrams illustrating the appearance of the gas sensor mounted to a container according to a first embodiment of the present disclosure.

FIG. 11 illustrates a plurality of detectors configured to detecting different target gases of the gas sensor according to a first embodiment of the present disclosure.

FIG. 12 is a graph illustrating that pH variation of a detection solution in response to density of acetic acid of an external environment is generated in response to the amount of acetate ions dissolved in a buffer.

FIG. 13 is a graph illustrating that pH variation of a detection solution in response to density of acetic acid of an external environment is generated in an initial pH of the buffer.

FIGS. 14 to 17 are diagrams illustrating categories and states of foods in response to a color change of the gas sensor according to a first embodiment of the present disclosure.

FIG. 18 is a conceptual diagram illustrating a method for manufacturing the gas sensor according to a first embodiment of the present disclosure.

FIG. 19 is a conceptual diagram illustrating a gas sensor according to a second embodiment of the present disclosure.

FIG. 20 is a conceptual diagram illustrating a modification example of the gas sensor according to a second embodiment of the present disclosure.

FIG. 21 is a diagram illustrating a gas sensor mounted to a transparent part of a container according to an embodiment of the present disclosure.

FIG. 22 is a diagram illustrating a support part for mounting a gas sensor to a transparent part of a container according to an embodiment of the present disclosure.

FIG. 23 is a diagram illustrating a gas sensor mounted to an opaque part of a container according to an embodiment of the present disclosure.

FIG. 24 is a diagram illustrating that an instrument part having a gas sensor is hinge-coupled to an opaque part of a container according to an embodiment of the present disclosure.

FIG. 25 is an exploded perspective view illustrating an instrument part having a gas sensor according to an embodiment of the present disclosure.

FIGS. 26 to 29 are diagrams illustrating the observation appearance of a gas sensor mounted to a container according to an embodiment of the present disclosure.

FIGS. 30 and 31 are diagrams illustrating an image sensor for use in a refrigerator to obtain an image of a gas sensor according to an embodiment of the present disclosure.

FIGS. 32 and 33 are diagrams illustrating an image sensor for use in a covered refrigerator to obtain an image of a gas sensor according to an embodiment of the present disclosure.

FIGS. 34, 35, 36A and 36B are diagrams illustrating an image sensor for use in an upright refrigerator to obtain an image of a gas sensor according to an embodiment of the present disclosure.

FIG. 37 is a block diagram illustrating a refrigerator according to a first embodiment of the present disclosure.

FIG. 38 is a block diagram illustrating a mobile device according to a first embodiment of the present disclosure.

FIG. 39 is a conceptual diagram illustrating a method for acquiring information regarding a target food by fabricating an image acquired from an image sensor of the refrigerator according to a first embodiment of the present disclosure.

FIG. 40 is a block diagram illustrating a refrigerator according to a second embodiment of the present disclosure.

FIG. 41 is a block diagram illustrating a mobile device according to a second embodiment of the present disclosure.

FIG. 42 is a block diagram illustrating a refrigerator according to a third embodiment of the present disclosure.

FIG. 43 is a diagram illustrating a coupling structure between a gas sensor of a refrigerator and a container according to a third embodiment of the present disclosure.

FIG. 44 is a flowchart illustrating a method for controlling a refrigerator according to a first embodiment of the present disclosure.

FIG. 45 is a flowchart illustrating a method for controlling a refrigerator according to a third embodiment of the present disclosure.

BEST MODE

Reference will now be made in detail to the embodiments of the present disclosure, examples of which are illustrated in the accompanying drawings, wherein like reference numerals refer to like elements throughout. A gas sensor, a refrigerator having the gas sensor, and a method for manufacturing the refrigerator according to embodiments of the present disclosure will hereinafter be described with reference to the attached drawings.

A gas sensor according to embodiments of the present disclosure can be used in various technical fields that measure specific gases. For example, the various technical fields may include environment management fields, safety management fields, medical diagnosis fields, food management fields, etc. For detailed description of structures and operations of the devices according to the present disclosure, the following embodiment will disclose the exemplary case in which the gas sensor is used in food management monitoring a state of food.

FIG. 1 is a diagram illustrating categories and density of gas generated in response to a ripening degree of kimchi.

FIG. 2 is a diagram illustrating categories and density of gas generated in response to a ripening degree of meat. FIG. 3 is a diagram illustrating categories and density of gas generated in response to a ripening degree of fruits and vegetables. FIG. 4 is a graph illustrating density of carbon dioxide ($CO_2$) according to a ripening period of fruits and vegetables.

Various kinds of gas may be generated in the ripening or rotting time of food. The category and amount of generated gas are affected by the ripening degree of food, added spices or added materials, etc.

Gas components closely related to the ripening degree of food from among the generated gas may include volatile organic acid, ammonia, etc. The gas components are not detected in a fresh state of food, and the density of gas components increases in proportion to the ripening degree of food.

Referring to FIG. 1, if a fermented food (i.e., kimchi) ripens, various gases, for example, acetic acid, aldehydes, sulfur compounds, alcohols, etc., may be generated. In this case, the principal gas generated in the ripening process of kimchi may be aldehydes, sulfur compounds, alcohol, etc.

In order to determine whether a target food is kimchi by detecting gas generated in the target food, there is a need to recognize whether all of the above-mentioned principal gases is detected or whether only a specific gas from among the principal gases is detected. Whereas the density of aldehyde or alcohol from among aldehyde, sulfur compound, and alcohol is reduced in the ripening process of kimchi, the density of sulfur compound may increase. An initial density of the sulfur compound is rather high. Therefore, when a high-density sulfur compound having at least a predetermined density is detected from gas generated in target food, the target food may be determined to be kimchi. That is, the high-density sulfur compound may be used as an index for deciding whether the target food is kimchi.

Although the above-mentioned aldehydes, sulfur compounds, and alcohol, especially, the sulfur compounds, may be used as an index for deciding whether the target food is kimchi, the above-mentioned gas is gas based on foodstuffs such as salted seafood, spices, etc. so that the principal gas may not be absolutely associated with fermentation of kimchi or the ripening degree of kimchi.

Gas directly affecting fermentation is volatile organic acid generated by by-product microbes. As can be seen from the example of FIG. 1, the volatile organic acid indicates acetic acid, such that the acetic acid may be used as an index for deciding the ripening degree of kimchi. As can be seen from FIG. 1, little acetic acid is generated in an initial fermentation process, and is then gradually increased in response to the progress of fermentation. However, the density of acetic acid is greatly lower than that of other gas, for example, acetic acid may have a density of about a few ppm.

Therefore, in order to recognize the ripening degree of fermented food such as kimchi, it is necessary to detect volatile organic acid having density of 1 ppm or less, from among other gases having density corresponding to a maximum of several hundred ppm.

The olfactory organ of most people can discriminate volatile organic acid from other gases even at a selectivity of one-to-several hundreds although there is a little difference in selectivity among people. However, most commercially available gas sensors may have difficulty in selectively measuring only the volatile organic acid having density of about several ppm from among other gas components having density of several hundred ppm.

In the case of general food but not the fermented food, the ripening or rotten degree of the general food can be derived from gas components generated in the general food. If meat is stored at a low temperature for a long time, protein is decomposed by microbes, so that amino acid is increased. The ripening process of such meat may be basically considered a gradual rotting process. Referring to FIG. 2, during the ripening process of meat, various gases, for example, ammonia, sulfur compounds, aldehydes, Volatile Organic Compounds (VOCs), etc, may occur in an amino-acid metabolic process caused by germs propagated in protein. Hydrogen sulfide may be suitably used as a single gas capable of being used as an index for deciding whether target food is meat. In the same manner as in kimchi, the density of hydrogen sulfide may increase in the ripening process of meat. However, the hydrogen sulfide has a low density in a different way from kimchi. Therefore, when low-density hydrogen sulfide of a predetermined density or less is detected, the target food may be considered a meat.

However, gases, such as sulfur compounds, aldehydes, VOCs, etc. may be modified according to categories or parts of meat within the same kind of gas. Therefore, ammonia may be used as gas that can be used as an index for indicating the ripening or rotten degree of meat. Referring to FIG. 2, although a foodstuff is stored in a refrigerating chamber for several days (for example, 6 days), a very small amount of ammonia gas or sulfur compound occurs so that a human being has difficulty in smelling the ammonia gas. A small amount of ammonia gas or hydrogen sulfide occurs in response to the ripening degree of meat, so that a resolution of 1 ppm or less is needed to correctly recognize whether the corresponding food is meat as well as to recognize the ripening degree of the meat. The resolution and sensitivity may be factors indicating a minimum density capable of being measured by sensors.

Although not shown in FIG. 2, fish may emit low-density hydrogen sulfide in the ripening process in the same manner as in the meat, and it is well known in the art that the amount of emitted trimethylamine (TMA) gradually increases in proportion to the increasing rotten degree of meat. Therefore, in the case of fish, low-density hydrogen sulfide may be used as the recognition index in the same manner as in meat, and trimethylamine (TMA) may be used as the ripening index of fish. In order to determine whether target food is meat or fish, the recognition index and the ripening index may be simultaneously used.

Referring to FIGS. 3 and 4, gas such as ethylene, VOC, or carbon dioxide ($CO_2$) may occur in the ripening process of fruits and vegetables. The graph of FIG. 4 illustrates the density of carbon dioxide ($CO_2$) generated in the ripening process of fruits and vegetables.

Ethylene may be used as a single gas capable of being used as an index for deciding whether target food is fruit or vegetable. Although ethylene has different densities, it is well known in the art that the ethylene is commonly generated from fruits and vegetables. Therefore, if ethylene is detected from target food, the target food may be determined to be fruits and vegetables.

FIG. 4 is a graph illustrating density variation of carbon dioxide ($CO_2$) according to a retention period of apples and grapes. Although apples and grapes emit ethylene, it is generally well known in the art that grapes emit a relatively lower-density ethylene than apples. Carbon dioxide ($CO_2$) is generated by respiration of fruits and vegetables and propagation of bacteria and germs. Although there is a difference in the amount of emitted ethylene between apple and grape, the apple and the grape are similar to each other in terms of the amount of emitted carbon dioxide ($CO_2$) and the incremental trend of the carbon dioxide ($CO_2$) as shown in FIG. 4. Therefore, ethylene may be used as the index of the ripening or rotten degree of fruits and vegetables.

The following Table 1 illustrates various kinds of gases capable of being used as types of target food, recognition indexes for identifying the types of target food, and indexes for deciding the ripening or rotten degree of target food.

TABLE 1

| Food Types | Recognition Indexes | Ripening Indexes |
| --- | --- | --- |
| Kimchi | High-density hydrogen sulfide | Acetic acid |
| Meat | Low-density hydrogen sulfide | Ammonia |
| Fish | Low-density hydrogen sulfide | Trimethylamine (TMA) |
| Fruits and vegetables | Ethylene | Carbon dioxide ($CO_2$) |

As described above, in order to recognize the ripening or rotten degree of target food by detecting gas generated in the target food, it is necessary for the gas sensor to independently detect the index for indicating types of different foods and the index for indicating the ripening or rotten degree of different foods. In other words, the gas sensor needs to detect different target gases independently of each other. In addition, high selectivity and high sensitivity (resolution of sub ppm) are needed so that specific gas of a ppm level from among plural gases having density of several hundreds of ppm can be selectively detected.

The gas sensor according to an embodiment of the present disclosure can be implemented to have high selectivity and high sensitivity (resolution of sub ppm) using principles similar to that of the olfactory system of a human being, and can detect different target gases independently of each other. The structure and operation principles of the gas sensor according to an embodiment of the present disclosure will hereinafter be described in detail.

FIGS. 5 to 7 are diagrams illustrating a gas sensor according to a first embodiment of the present disclosure.

Referring to FIG. 5, the gas sensor 100 according to the first embodiment may include a base 110; a plurality of detectors 120 provided to the base 110 to form a predetermined array; and a transparent membrane 130 attached to the detectors 120 so as to cover the detectors 120. Target gas reacts with the detectors 120 after passing through the base 110. The detectors 120 is discolored in response to pH variation generated upon reaction with the target gas. That is, the detectors 120 may determine whether or not the target gas is detected on the basis of a color change.

The base 110 may be implemented as a hydrophobic membrane needed for gas permeability. Most hydrophobic gas permeability materials including polytetrafluoroethylene, thermoplastic polyurethane, polyethylene, low density polyethylene, linear low density polyethylene, high density polyethylene, Tyvek, etc. may be used as the base 110.

The detectors 120 must detect gas generated in foodstuff by reacting with the gas, the base 110 formed of the above-mentioned materials may prevent permeation of liquid so as to prevent a liquid material from reacting with the detectors 120. That is, as can be seen from FIG. 6, whereas gas being shifted to the base 110 arrives at the detectors 120 after passing through the base 110, liquid shifted to the base 110 does not pass through the base 110 so that the liquid does not arrive at the detectors 120. A transparent membrane 130 may be formed of a gas non-permeable material in such a manner that gas having passed through the base 110 can arrive at the detectors 120. That is, as can be seen from FIG. 6, the transparent membrane 130 may prevent permeation of gas and liquid.

The transparent membrane 130 may be attached to the detectors 120 so as to cover the detectors 120 attached to the base 110. As can be seen from FIG. 7, color change of the detectors 120 can be observed through the transparent membrane 130. A user can immediately view color change of the detectors 120 through the transparent membrane 130. Alternatively, the image sensor I may obtain an image of color change of the detectors 120 through the transparent membrane 130. When the gas sensor 100 is mounted to a predetermined container storing foodstuffs therein, the base 110 and the foodstuff may face each other, and the transparent membrane 130 may be attached to the container.

FIGS. 8 to 10 are conceptual diagrams illustrating the appearance of the gas sensor mounted to a container according to a first embodiment of the present disclosure.

Referring to FIGS. 8 and 9, when the gas sensor 100 is mounted to a predetermined container, the base 110 is installed to face a target food O accommodated in the container. Gas generated from the target food O arrives at the detectors 120 after passing through the base 110. Since the base 110 is located to face the target food O present in the container, color change of the detectors 120 needs to be observed from a back surface of the base 110. Therefore, the transparent membrane 130 formed of transparent resin through which the user can observe color change of the detectors 120 is installed to cover the detectors 120. The user can directly observe color change of the gas sensor 100 through the transparent membrane 130, and the image sensor may detect the color change of the gas sensor 100 through the transparent membrane 130. A detailed description thereof will be given later.

If a specific part to which the gas sensor 100 is attached is formed of a transparent material, the user can immediately observe color change of the gas sensor 100. If the gas sensor 100 is mounted to a part formed of an opaque material, it is impossible for the user to observe color change of the gas sensor 100. A method for mounting the gas sensor 100 to the part formed of an opaque material that enables the user to observe color change of the gas sensor 100 will hereinafter be described in detail.

If the gas sensor 100 is attached to a predetermined container, the transparent membrane 130 may be omitted and the detectors 120 may be immediately attached to the container as can be seen from FIG. 10. That is, since the container can serve as the transparent membrane 130, the transparent membrane 130 may be omitted. In this case, it may be preferable that the gas sensor 100 be attached to a transparent part of the container.

The detectors 120 may be implemented as a hydrophilic membrane having a detection solution. The hydrophilic membrane may be implemented as hydrophilic materials including cellulose ester, glass fiber, cellulose acetate, cellulose fiber, litmus paper, traditional Korean paper, filter paper, etc. The detection solution discolored by reacting with target gas may be absorbed into the hydrophilic membrane, and so that the detection solution is then fixed.

The detection solutions of the respective detectors 120 may have different characteristics because target gases to be detected using the respective detects 120 are different from one another. FIG. 11 illustrates a plurality of detectors 120 configured to detecting different target gases of the gas sensor according to a first embodiment of the present disclosure.

As illustrated in FIG. 11, six detectors 120 may detect hydrogen sulfide, ammonia, ethylene, trimethylamine (TMA), acetic acid, and carbon dioxide ($CO_2$), respectively. The categories and numbers of the above-mentioned gases are merely exemplary, the categories and numbers of detection gases according to the present disclosure are not limited thereto, and the number of detectors 120 may be set to 6 or higher.

Polar substance such as acetic acid, ammonia, hydrogen sulfide, or trimethylamine (TMA), may be dissolved in polar solvent such as water or ethanol. Therefore, the detection solution for detecting the above-mentioned polar substance may include a polar solvent.

Nonpolar substance such as ethylene or carbon dioxide ($CO_2$) may not be dissolved in polar solvent such as water or ethanol. Therefore, the detection solution for detecting the above-mentioned nonpolar substance may include nonpolar solvent such as benzene, carbon bisulfide, carbon tetrachloride, or nucleic acid.

If target gas is dissolved in the detection solution, the pH value of the detection solution is changed. Thus, the pH indicator having a color being changed in response to the pH variation may be used, so that it can be recognized whether the target gas is detected through the pH variation generated when the target gas is dissolved. The pH indicator is characterized in that its own color is changed in response to the degree of reaction with $H_2$ ions contained in the solution.

That is, the pH value of the detection solution is changed because the target gas is dissolved in the detection solution, and the color of the pH indicator is also changed in response to the changed pH. As a result, if the color of the detection solution is changed, it can be recognized that the corresponding target gas has been detected and the corresponding target gas has been generated in the target food O.

The pH indicator may be set to a pH indicator, the color of which is changed within the pH range when each target gas is dissolved in solvent. If necessary, one or more pH indicators may be used.

For example, the detection solution of the detectors 120 for detecting the acetic acid may include a bromothymol blue pH indicator and a methyl red pH indicator. Bromothymol blue pH indicator is discolored from blue to yellow when a pH value is reduced from 7.6 to 6.0. Methy red pH indicator is discolored from yellow to red when a pH value is reduced from 6.0 to 4.8. If the detector 120 for detecting the acetic acid reacts with the acetic acid, the bromothymol blue is blue in color when a pH is set to 7.6. Thereafter, if the pH value reaches 6.0, the bromothymol blue is changed to yellow in color, so that the yellow color appears. If the pH value is set to 6.0, the methy red is yellow in color, so that the yellow color appears. Thereafter, if the pH value is set to 4.8, the methy red is changed to red in color, so that the red color appears. In other words, if the color of the detector 120 for detecting the acetic acid is sequentially changed in the order of blue→yellow→red, it can be recognized that the density of acetic acid emitted from the target food O increases.

In addition, the detection solution of the detectors 120 for detecting ammonia may include thymol blue and phenolphthalein used as the pH indicator. If low-density ammonia is detected, cresol red and bromothymol blue having the same density level may be independently or collectively used. In more detail, when the target gas is ammonia having a dissociation constant (pKa) of 9.3, the pH indicator including a pH 9.3 band is used, such that thymol blue discolored in the range from pH 8.0 to pH 9.6 may be used. In order to measure the density of rarefied ammonia of a certain ppm or less, discoloration must appear even in low pH variation. In this case, cresol red discolored in the range from pH 7.0 to pH 8.8 or bromothymol blue discolored in the range from pH 6.0 to pH 7.6 may be used.

As described above, the detection solution may include a solvent in which the target gas can be dissolved and a pH indicator for colorfully indicating pH variation based on dissolution of the target gas. In addition, the detection solution may further include a moisture absorbent to suppress moisture evaporation of the detection solution as well as to reduce the moisture sorbent. For example, the moisture absorbent may include any one of glycerin, ethylene glycol, polyethylene glycol, calcium chloride, sodium chloride, etc.

The detection solution may include a buffer solution having various densities and various pH values so as to adjust reaction sensitivity to the target gas and a measurement range of the target gas. As a representative example of the target gas, the detection solution of the detectors 120 for detecting acetic acid may be used. FIG. 12 is a graph illustrating that pH variation of the detection solution in response to acetic acid of an external environment is generated in response to the amount of acetate ions dissolved in a buffer. FIG. 13 is a graph illustrating that pH variation of the detection solution in response to density of acetic acid of an external environment is generated in an initial pH of the buffer.

The graph of FIG. 12 shows that pH variation in response to the density of acetic acid gas of the detection solution having an initial pH of 8 is calculated at each ion density (3 mM, 10 mM, 30 mM, or 100 mM). The density of initial acetate ion may indicate the density of acetate ions dissolved in the buffer of the detection solution.

Referring to FIG. 12, if the initial acetate ion is set to 3 mM, the highest pH variation of the solution occurs in response to density variation of acetic acid gas. Especially, a high pH variation also occurs in the acetic acid gas of 1 ppm or less. Therefore, it can be recognized that reactivity with the acetic acid gas has superior reactivity as the density of initial acetate ions is gradually reduced.

Meanwhile, although subacid acetic acid has a higher density, it is substantially difficult to drop a pH value of the solution down to 3 or less. As a result, when the initial acetate ion has the density of 3 mM, it may be difficult to measure the density of acetic acid gas of 10 ppm or higher.

On the contrary, if the initial acetate ion has the density of 100 mM, pH variation in association with the acetic acid gas of 1 ppm or less is not so great, as compared to the case in which the initial acetate ion has the density of 3 mM. However, since a pH value is maintained at about '5' even when the acetic acid of the external environment has the density of 10 ppm, it can be expected that pH variation is measured even in the gas environment of a high-density acetic acid of 10 ppm or higher.

The graph of FIG. 13 shows pH variation changing with the density of acetic acid gas when the density of initial acetate ion of the buffer is fixed to 30 mM and an initial pH value of the buffer solution is changed.

Referring to FIG. 13, if the initial pH value of the buffer is set to 4, a pH value of the solution is reduced to 4 or less when the acetic acid gas of 3 ppm or higher is present, so that it can be recognized that the measurement range of the acetic acid gas is set to 3 ppm or higher. If the initial pH value of the buffer is set to 5, a pH value of the buffer solution is reduced to 5 or less when the acetic acid gas of 1 ppm or higher is present, so that it can be recognized that the measurement range is set to 3 ppm or higher. If the initial pH value of the buffer is set to 6, 7 and 8, similar waveforms can be obtained.

A composition ratio of the buffer may be decided on the basis of content illustrated in FIGS. 12 and 13. That is, the density of initial acetate ion and the initial pH of the buffer may be determined according to the reaction sensitivity to the target gas and the measurement range.

As described above, the detectors 120 may respectively react with different target gases, and may be discolored according to the density of target gas. Therefore, the gas sensor 100 including the plurality of detectors 120 according to the first embodiment of the present disclosure may detect different target gases independently of each other, and the user may confirm the density of target gas through color of the detectors 120 discolored according to the density of target gas. Furthermore, it is confirmed whether a certain target gas has been detected such that the categories of target food O emitting the target gas and the ripening or rotten degree of the target food O can be recognized.

FIGS. 14 to 17 are diagrams illustrating categories and states of foods in response to a color change of the gas sensor 100 according to a first embodiment of the present disclosure.

As can be seen from Table 1, if the detectors 120 for detecting hydrogen sulfide as target gas are discolored, it can be recognized that the target food O is kimchi, meat or fish.

As illustrated in FIG. 14, if the degree of discoloration of the hydrogen sulfide detector 120 is high, this means the presence of a high-density hydrogen sulfide, such that the user can recognize that the target food O is kimchi. If a high-density hydrogen sulfide is detected and the detector 120 for detecting acetic acid as target food is discolored, the user can recognize the ripening degree of kimchi according to the degree of discoloration. Although color change of the detectors 120 is denoted by deep and light shadows as shown in FIG. 14, the detectors 120 may actually be discolored according to color change of the pH indicator. For example, if the acetic acid detector 120 includes bromothymol blue and methyl red used as the pH indicator, the acetic acid detector 120 is sequentially discolored in the order of blue→yellow→red in proportion to the increasing detection density of acetic acid. Such sequential discoloration of the acetic acid detector 120 may also be equally applied to other detectors 120.

In addition, as illustrated in FIG. 15, if a low-density hydrogen sulfide is detected and the detector 120 for detecting ammonia as target gas is discolored, the user may recognize that the target food O is meat and may also recognize whether the meat is fresh or rotten according to the degree of discoloration of the ammonia detector 120.

As illustrated in FIG. 16, if a low-density hydrogen sulfide is detected and the detector 120 for detecting trimethylamine (TMA) as target gas is discolored, the user may recognize that the target food O is fish, and may also recognize whether the fish is fresh or rotten according to the degree of discoloration of the TMA detector 120.

As illustrated in FIG. 17, if the detector 120 for detecting ethylene as target gas is discolored, the user may recognize that the target food O is fruits and vegetables. If ethylene is searched and the detector 120 for detecting $CO_2$ as the target gas is discolored, the user may recognize whether the fruits and vegetables are fresh or rotten according to the degree of discoloration.

The gas sensor 100 is mounted to the container including food, detects target gases generated in the food stored in the container, and is discolored, such that the gas sensor 100 may provide the user with information regarding the types and states of food. The container to which the gas sensor 100 is mounted and a method for mounting the gas sensor 100 to the container will hereinafter be described.

As described above, the gas sensor 100 according to the first embodiment of the present disclosure may include a base, a hydrophilic membrane, and a transparent membrane 130, and a method for manufacturing the gas sensor 100 is illustrated in FIG. 18.

FIG. 18 is a conceptual diagram illustrating a method for manufacturing the gas sensor 100 according to a first embodiment of the present disclosure. Referring to FIG. 18, a predetermined amount of detection solution including the pH indicator and the like drops to the hydrophilic membrane, and is thus absorbed into the hydrophilic membrane. The hydrophilic membrane in which the detection solution is absorbed is heated at a temperature of about 80° C. for about 30 seconds, so that the hydrophilic membrane is dried. The process for drying the hydrophilic membrane is needed when the transparent membrane 130 is attached to the hydrophilic membrane. That is, a moisture evaporation process is needed when the transparent membrane 130 is heat-bonded to the hydrophilic membrane.

If the hydrophilic membrane is dried, the dried hydrophilic membrane is placed on the base 110, the hydrophilic membrane is covered with the transparent membrane 130, and the transparent membrane 130 and the hydrophilic membrane are heat-bonded each other. If the manufactured gas sensor 100 is installed in a food container or a refrigerator, the moisture absorbent contained in the detection solution absorbs the peripheral water vapor in such a manner that there occurs reaction of the pH indicator in which reaction proceeds under the presence of moisture. If the moisture absorbent absorbs the peripheral water vapor so that the hydrophilic membrane includes moisture, the detection solution reacts with the target gas, so that the pH indicator is discolored in response to the changing pH value.

The user observes color change of the detector 120 of the gas sensor with the naked eye so that the user can recognize the type of target food O and can confirm the ripening degree of the target food O. However, the user may have difficulty in visually recognizing slight color change of the detector 120. If the number of detectors 120 increases, the user may have difficulty in recognizing the category of food or the degree of freshness of food on the basis of discoloration information of the gas sensor 100.

In order to address the above-mentioned issues, the gas sensor according to a second embodiment of the present disclosure may further include an image detector 140 configured to acquire an image regarding color change of the above-mentioned gas sensor.

FIG. 19 is a conceptual diagram illustrating a gas sensor according to a second embodiment of the present disclosure. FIG. 20 is a conceptual diagram illustrating a modification example of the gas sensor according to a second embodiment of the present disclosure.

Referring to FIG. 19, the gas sensor according to the second embodiment may include a gas sensor 100 of FIG. 5, an image detector 140 for obtaining an image regarding the color change of the gas sensor 100, a transmitter 150 for transmitting the gas-sensor image data obtained by the image detector 140 to an external part, and a battery 160 for providing a power source to operate the image detector 140 and the transmitter 150.

The image detector 140 may use a photodiode, a CMOS image sensor, and a CCD. The image detector 140 may obtain images of the gas sensor so as to detect color change of each detector 120 contained in the gas sensor 100. The image detector 140 may successively obtain the images of the gas sensor 100, and may obtain data regarding the color change by sampling the acquired images. Alternatively, the image detector 140 may obtain data of the color change by obtaining the image of the gas sensor 100 at intervals of a predetermined time.

The obtained data may be transmitted to the external device having a receiver through the transmitter 150. The external device may analyze data received from the gas sensor 300, and may determine the types of target food O and the states of the target food O. Various communication schemes between the transmitter 150 of the gas sensor 300 and the receiver of the external device may use various wireless communication schemes.

The battery 160 may provide a power source for operating the image detector 140 and the transmitter 150. The battery 160 may be various commercial disposable batteries or rechargeable batteries.

Alternatively, as can be seen from the medication example of the second embodiment of FIG. 20, the gas sensor 300 may include a power receiver 170 capable of being wirelessly rechargeable using a wireless power transmission technology instead of using the battery 160 of FIG. 19. The power receiver 150 may be configured to be appropriate for various wireless power transmission schemes, for example, a magnetic induction scheme, a magnetic resonance scheme, an electromagnetic wave scheme, etc.

The gas sensor according to the second embodiment may obtain the color change data of the gas sensor 100 using the image detector 140, may transmit the obtained color change data to the external device having a data analysis function, and may thus allow the external device to determine a state of the target food O. If the external device, for example, the refrigerator, analyzes data received from the gas sensor 300, displays the type or state of the target food O through a display 910 or the like, the user can recognize the type or state of the target food O without viewing the color change of the gas sensor 300 with the naked eye. Alternatively, a mobile device 1000, such as a smartphone or a tablet computer, may analyze data received from the gas sensor 300, and may inform the user of the state of the target food O through the display 910. Furthermore, the user may also control a temperature of the refrigerator storing the target food O therein using the mobile device 1000. A detailed description thereof will hereinafter be given in detail.

The gas sensors 100 and 300 according to the embodiment may be mounted to the container storing the food therein.

FIG. 21 is a diagram illustrating a gas sensor mounted to a transparent part of a container according to an embodiment of the present disclosure. FIG. 22 is a diagram illustrating a support part for mounting a gas sensor to a transparent part of a container according to an embodiment of the present disclosure.

If the container C of the food has a transparent part or a partially transparent part, the transparent membrane 130 contained in the gas sensor 100 of the first embodiment is attached to the inner wall of the transparent part of the container C in such a manner that the target food O and the base 110 face each other. The gas sensor 100 according to the first embodiment has a patch format, so that the gas sensor may be attached to the inner wall using a predetermined adhesive material. The gas sensor 300 according to the second embodiment includes various electronic components, such as the image detector 140, the transmitter 150, and the battery 160, so that it may be undesirable that the gas sensor 300 be directly attached to the inner wall on which the target food O is placed.

The gas sensor 100 is not directly attached thereto, a predetermined support part 520 for installation of the gas sensor 100 may be provided at the inner wall of the transparent part of the container C, and the gas sensor 100 may also be installed at the support part 520 (See a reference number 500).

The support part 520 of FIG. 22 may enable the gas sensor 100 to be detachably coupled through slide coupling. The support part 520 is configured in the form of "∟" shape, and may be attached to a transparent wall of the container C. Although three support parts 520 are shown in FIG. 22, there is no limitation in the number of support parts 520. The gas sensor 100 may be slidably coupled or separated along the support part 520.

The gas sensor 100 according to the first embodiment is configured in the form of a patch and is formed of a flexible material. As can be seen from FIG. 22, after the gas sensor 100 is mounted to the slide member 510 having suitable stiffness so that the gas sensor 100 can be appropriately mounted to the support part 520, the slide member 510 is then amounted to the support part 520 so that the gas sensor 100 can be mounted to the container C. The structure or shape of the support part 520 shown in FIG. 20 is shown as an example, and various other structures or shapes can also be applied to the support part 520 without departing from the scope or spirit of the present disclosure.

FIG. 23 is a diagram illustrating a gas sensor mounted to an opaque part of a container C according to an embodiment of the present disclosure. FIG. 24 is a diagram illustrating that an instrument part having a gas sensor is hinge-coupled to an opaque part of a container C according to an embodiment of the present disclosure. FIG. 25 is an exploded perspective view illustrating an instrument part having a gas sensor according to an embodiment of the present disclosure.

If the gas sensor 100 is mounted to the inner wall of the opaque part of the container C, it is impossible for the user to visually observe color change of the gas sensor 100. The gas sensor 300 according to the second embodiment can be installed in the container C because the image detector 140 obtains an image of the gas sensor 100. However, as described above, the gas sensor 300 according to the second embodiment includes various electronic components such as an image detector 140, a transmitter 150, and a battery 160, so that it is undesirable that the gas sensor 300 be directly mounted to the inner wall to which the target food O will be mounted.

In accordance with the embodiments, a hole 615 is formed at an opaque part of the container C in which the gas sensors 100 and 300 will be installed, and the gas sensors 100 and 300 are installed in the hole 615. If the gas sensors 100 and 300 are installed as described above, the gas sensors 100 and 300 may detect the gas generated from the target food O accommodated in the container C through the hole 615, and the user may directly observe color change of the gas sensors 100 and 300.

As can be seen from FIG. 23, the gas sensors 100 and 300 are mounted to a predetermined instrument part 600. As can be seen from FIG. 24, the instrument part 600 may be hinge-coupled to the wall of the container C having a hole. A fixing groove 621 may be provided at the bottom of the hole-included part, so that the instrument part 600 can be fixed to the container C when being brought into contact with the wall of the container C.

As can be seen from FIG. 25, the instrument part 600 may include a main body 610 having a hole 611 in which the gas sensors 100 and 300 are installed. Here, the hole 611 is located at the center of the main body 610. A fixing part 620 coupled to the fixing groove 621 of the wall of the container C is provided at the bottom of the main body 610. Thus, when the instrument part 600 contacts the wall of the container C, the instrument part 600 can be fixed to the wall of the container C through the fixing part 620.

A transparent cover 612 may be installed in the hole 611 of the main body 610 so that the transparent cover 612 can prevent external impurities from reaching the gas sensors 100 and 300. In order to prevent leakage of fluid through the hole 611 of the instrument part 600, the O-ring 613 formed of a rubber material may be installed in the hole 611 of the instrument part 600 as shown in FIG. 25. If the gas sensors 100 and 300 are mounted to the hole 611, an additional gas permeable layer 614 is selectively installed, and the instrument part 600 is hinge-coupled to the wall of the container C including a hole 615. The structures, shapes, and constructions of the instrument part 600 shown in FIGS. 23 to 25 are merely exemplary, and it should be noted that other structures, other shapes, and other constructions may also be applied to the instrument part 600 without departing from the scope or spirit of the present disclosure. The container shown in FIGS. 23 to 25 may also be used as a gas detection container capable of detecting the target gas emitted from a target object accommodated in the container.

If the container coupled to the gas sensors 100 and 300 as shown in FIGS. 23 to 25 is placed on a shelf of the refrigerator and the shelf is inserted to accommodate the container into the refrigerator as shown in FIG. 26, the user can observe color change of the gas sensors 100 and 300 with the naked eye.

However, in the case of using the refrigerator shown in FIG. 27 in which the container C is put on the bottom of the storage chamber, instead of using the refrigerator in which the container C placed on a shelf is inserted into the refrigerator, the user is unable to directly observe color change of the gas sensors 100 and 300. In this case, as shown in FIG. 27, a reflector R capable of reflecting the images of the gas sensors 100 and 300 is installed at the wall of the storage chamber facing the gas sensors 100 and 300, so that the user can observe color change of the gas sensors 100 and 300 from the images of the gas sensors 100 and 300 reflected through the reflector R.

If the container coupled to the gas sensors 100 and 300 as shown in FIGS. 21 to 22 is accommodated in the refrigerator in which the container C is put on the bottom of the storage chamber as shown in FIG. 28, the user can observe color change of the gas sensors 100 and 300 with the naked eye.

However, in the case of using the refrigerator shown in FIG. 29 in which the container C placed on a shelf is inserted into the refrigerator, instead of using the refrigerator in which the container C is put on the bottom of the storage chamber, the user is unable to directly observe color change of the gas sensors 100 and 300. In this case, as shown in FIG. 29, the reflector R capable of reflecting the image of the gas sensor 100 is installed at the bottom of the shelf facing the gas sensor 100, so that the user can observe color change of the gas sensor 100 from the image of the gas sensor 100 reflected through the reflector R.

The user may not directly observe the color change of the gas sensor, instead detecting the color change of the gas sensor by obtaining the gas sensor image from the image sensor mounted to the refrigerator. FIGS. 30 and 31 are diagrams illustrating an image sensor for use in a refrigerator to obtain an image of a gas sensor according to an embodiment of the present disclosure.

The refrigerator applied to this embodiment may be a kimchi refrigerator configured to store kimchi therein or a general refrigerator. In addition, the refrigerator may be classified into an upright refrigerator and a cover-type refrigerator (hereinafter referred to as a covered refrigerator). The upright refrigerator and the covered refrigerator may be kimchi refrigerators or general refrigerators. There is no limitation in categories and usages of the refrigerator of the present disclosure and, as such, all kinds of refrigerators may be applied to the present disclosure.

If the container including the gas sensors 100 and 300 shown in FIGS. 23 to 25 is accommodated on the shelf of the refrigerator 900 as shown in FIG. 30, the image sensor 800 capable of obtaining the images of the gas sensors 100 and 300 may be mounted to the wall of the refrigerator 900 facing the gas sensors 100 and 300.

If the container C including the gas sensor 100 shown in FIGS. 21 and 22 is accommodated on the shelf of the refrigerator 900 as shown in FIG. 31, the image sensor 800 capable of obtaining the image of the gas sensor 100 may be installed at the bottom of the shelf facing the gas sensor 100.

The installation positions of the image sensors 800 shown in FIGS. 30 and 31 are merely examples, the gas sensor may be installed at any position facing the gas sensor of the container C in the refrigerator 900. In more detail, if the image acquisition available range of the image sensor 800 and the container C are accommodated in the refrigerator 900, the installation position of the image sensor 800 may be determined in consideration of the position of available gas sensor.

FIGS. 32 and 33 are diagrams illustrating the image sensor 800 for use in a covered refrigerator 900 to obtain an image of the gas sensor according to an embodiment of the present disclosure.

Referring to FIG. 32, if the container C mounted to the gas sensors 100 and 300 is accommodated in the storage chamber 903 as shown in FIGS. 23 to 25, the image sensor 800 may be installed at the wall of the storage chamber 903 so that the gas sensors 100 and 300 are located to face the gas sensors 100 and 300 of the container C.

In addition, as shown in FIG. 33, if the container C including the gas sensor 100 shown in FIGS. 21 and 22 is accommodated in the storage chamber 903, the image sensor 800 is installed at the inside of the refrigerator cover 901 in such a manner that the image sensor 800 can obtain the image of the gas sensor 100 when the refrigerator cover 901 is closed.

FIGS. 34 and 35 are diagrams illustrating the gas sensor of the container C contained in the upright refrigerator 900 and the image sensor 800 mounted to the refrigerator 900. FIGS. 36A and 36B are diagrams illustrating a gas sensor and an image sensor mounted to a storage chamber divided by an internal shelf of the upright refrigerator according to an embodiment of the present disclosure. If the container C including the gas sensors 100 and 300 as shown in FIGS. 23 to 25 is accommodated in the storage chamber 903 as shown in FIG. 34, the image sensor 800 is installed at the inside of the refrigerator cover 901 in such a manner that the image sensor 800 can obtain the images of the gas sensors 100 and 300 when the refrigerator cover 901 is closed.

If the container C including the gas sensor 100 as shown in FIGS. 21 and 22 is accommodated in the storage chamber 903 as shown in FIG. 35, the image sensor 800 is installed at the bottom of the refrigerator shelf facing the gas sensor 100.

In addition, as shown in FIG. 36A, the gas sensor 100 may be installed at the wall of the storage space divided by a shelf. The image sensor 800 for obtaining the image of the gas sensor 100 is installed at the inside of the wall so as to face the gas sensor 100 as shown in FIG. 36B, so that the image sensor 800 reacts with the target gas and thus obtains the image of the discolored gas sensor 100. The installation position or the number of gas sensors shown in FIGS. 36A and 36B are merely exemplary, and other installation positions or other numbers of gas sensors may be applied to the refrigerator in such a manner that the gas sensors may be installed at the wall of the refrigerator.

If the target food stored on a specific shelf becomes rotten, the gas sensor detects the gas generated in the rotting process of food, so that the image of the discolored gas sensor can be obtained from the image sensor. The controller of the refrigerator may determine whether the target food is rotten on the basis of the gas-sensor discoloration information shown in the image obtained from the image sensor, and may determine the position of the image sensor having transmitted the image of the discolored gas sensor 100 to be the position of rotten food. The refrigerator may display the position of the rotten food through the display in such a manner that the user can recognize the rotten state of food.

If the image sensor 800 mounted to the refrigerator 900 obtains the image of the gas sensor 100, the refrigerator 900 may calculate the color change of the gas sensor 100 on the basis of the above image, and may determine the type or state of food. Various embodiments for determining the type and state of target food O by detecting color change of the gas sensor 100 will hereinafter be described in detail.

FIG. 37 is a block diagram illustrating a refrigerator 900 according to a first embodiment of the present disclosure. FIG. 38 is a block diagram illustrating a mobile device 1000 according to a first embodiment of the present disclosure.

Referring to FIG. 37, the refrigerator 900 may include an image sensor 800 for obtaining an image of the gas sensor 100 mounted to the container C; a controller 930 for determining a state of the target food O using the image obtained from the image sensor 800; a display 910 for displaying information regarding the target food (0) state decided by the controller 930; a cooling part 950 for adjusting a temperature of the storage chamber 903 by applying cool air to the storage chamber 903 according to the target food state decided by the controller 930; an input part 920 for enabling a user to input commands related to operations of the refrigerator 900; and a communication part 940 for transmitting information regarding the target food state decided by the controller 930 to an external mobile device 1000.

Referring to FIG. 37, the refrigerator 900 may include an image sensor 800 for obtaining an image of the gas sensor 100 mounted to the container C; a controller 930 for determining the type and state of the target food O using the image obtained from the image sensor 800; a display 910 for displaying information regarding the type and state of the target food O decided by the controller 930; a cooling part 950 for adjusting a temperature of the storage chamber 903 by applying cool air to the storage chamber 903 according to the type and state of the target food O decided by the controller 930; an input part 920 for enabling a user to input commands related to operations of the refrigerator 900; and a communication part 940 for transmitting information regarding the type and state of the target food O decided by the controller 930 to an external mobile device 1000.

The image sensor 800 is installed at the storage chamber 903 of the refrigerator 900 or the shelf or door of the refrigerator 900 as shown in FIGS. 27 to 30, so that the image sensor 800 obtains the image of the gas sensor 100 mounted to the container C. The image sensor 800 may be any one of a photodiode, a CMOS image sensor, and a CCD. The image sensor 800 may obtain the image of the gas sensor 100 so as to detect the color change of each detector 120 contained in the gas sensor 100. The categories of the image sensor 800 are not limited to the above-mentioned examples, and the optical device capable of obtaining the image of the gas sensor 100 may be contained in the image sensor 800 of this embodiment. A plurality of containers C, each of which includes the gas sensor 100, may be accommodated in the storage chamber 903, and the image sensor 800 is installed at each space in which the container C can be located so that a plurality of image sensors 800 may also be installed as necessary.

The image sensor 800 may successively obtain the image of the gas sensor 100, may obtain data of the color change by sampling the obtained image, and may obtain the image of the gas sensor 100 at intervals of a predetermined time, so that the image sensor 800 may obtain the data regarding the color change. The image sensor 800 may be successively exposed to a low-temperature environment because it is installed in the refrigerator 900. Therefore, frost may accumulate on the image sensor 800, so that it may be impossible to obtain a clear image of the gas sensor 100. The image sensor 800 according to the disclosed embodiment may include a predetermined heater capable of melting frost, or may be formed of a material for preventing occurrence of frost.

If the image sensor 800 obtains an image of the gas sensor 100 and transmits the obtained image to the controller 930, the controller 930 may calculate a difference in color between a pre-image obtained before the image sensor 800 is exposed to the target gas and a post image obtained after the image sensor 800 is exposed to the target gas. That is, the controller 930 may calculate a difference in color between a first color obtained before the image sensor 800 is exposed to target gas of the detector 120 constructing the gas sensor 100 and a second color obtained after the image sensor 800 is exposed to the target gas of the detector 120, so that the controller 930 may calculate the presence or absence of color change of the detector 120 and the degree of such color change. For example, after exposure to the initial color and the target gas of the detector 120, a color difference of the detector 120, shown in the images received from the image sensor 800, is calculated. In this case, the degree of discoloration can be recognized on the basis of a specific time before the sensor is exposed to the target gas. Alternatively, a color difference between the detector 120's color shown in a currently transmitted image and the other detector 120's color shown in a previously transmitted image is continuously calculated. In this case, it may be possible to recognize the degree of discoloration as time goes by. Although the color difference is calculated using any one of the above-mentioned schemes, it should be noted that desired data can be obtained through a predetermined operation.

If a color coordinate system of the image obtained from the image sensor 800 is an L-a-b coordinate system, the calculated color difference is converted into an RGB coordinate system, and then displayed. The operation for performing such conversion into the RGB coordinate system and displaying the conversion result is merely exemplary, and a color difference may be displayed using other kinds of coordinate systems.

FIG. 39 is a conceptual diagram illustrating a method for acquiring information regarding a target food O by fabricating an image acquired from an image sensor 800 of the refrigerator 900 according to a first embodiment of the present disclosure.

Referring to FIG. 39, the controller 930 may remove a background part other than the detector 120 from the image indicating the detector 120's color difference image converted into the RGB coordinate system. The controller 930 may classify the image from which the background part is removed into a plurality of images according to a red(R) region, a green(G) region, and a blue(B) region, may compare each of a pattern of the R region, a pattern of the G region, and a pattern of the B region with prestored data, and may obtain information regarding the target food O.

The controller 930 may configure the discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 930 may prestore data regarding patterns of the respective RGB regions indicating the type of the target food O and the state of the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the food type and food state expressed by the determined pattern to be the type and state of the target food O.

If the user detects the color change of the gas sensor 100 using the image sensor and uses the DB information, instead of observing the color change of the gas sensor 100 with the naked eye, the type and state of food can be more accurately determined.

If the type and state of the target food O are determined, the controller 930 may display the type and state of the target food O determined through the display 910. For example, if the target food O is kimchi and the kimchi is raw kimchi, the controller 930 may display a kimchi state indicating raw kimchi on the display 910.

If the user inputs a desired command for displaying such information, the controller 930 may display information regarding the type and state of food on the display 910. For example, if the user selects the container C to be confirmed through the input part 920, the controller 930 may display the type and state of the target food O calculated from the images received from the image sensor 800 configured to detect the gas sensor 100 of the selected container C on the display 910. If the target food O stored in the selected container C is kimchi and this kimchi is raw kimchi, the controller 930 may display specific information on the display 910, the specific information indicating that kimchi is stored in the corresponding container C and this kimchi is raw kimchi. The input part 920 may have a user interface through which the user can intuitively select the container C. The display 910 may have a user interface through which the user can intuitively select the type and state of the target food O.

The user may confirm information displayed on the display 910, and may input a command for a desired state of the target food O through the input part 920. The controller 930 may receive a command regarding the target food O from the user through the input part 920, so that the controller 930 may control a temperature of the storage chamber 903. For example, if the user inputs a command for maintaining a current kimchi state through the input part 920, the controller 930 may determine a temperature (capable of maintaining a current kimchi state) of the storage chamber 903 in consideration of a current kimchi state, and adjust a temperature of the storage chamber 903 by transmitting a control signal to the cooling part 950. Alternatively, if the user inputs a desired command for kimchi ripening through the input part 920, the controller 930 may determine a temperature of the storage chamber 903 in consideration of a current kimchi state so as to perform additional ripening of the kimchi, may transmit a control signal corresponding to the determined temperature to the cooling part 950, and may thus adjust a temperature of the storage chamber 903.

Alternatively, the controller 930 may determine a temperature of the storage chamber 903 in such a manner that the target food O reaches an optimum ripening state and the optimum ripening state can be maintained in response to the determined type and state of the target food O, may transmit a control signal corresponding to the determined temperature to the cooling part 950, and may thus automatically adjust the temperature of the storage chamber 903.

If information regarding a user-desired storage state of the target food O is previously input, the controller 930 may monitor the color change of the gas sensor 100 and may automatically control a temperature of the storage chamber 903 in response to the state of the target food O, so that the target food O reaches a desired storage state and this desired storage state can be maintained.

In addition, the refrigerator 900 according to a first embodiment may include a communication part 940 capable of communicating with the external mobile device 1000, so that image data of the gas sensor 100, obtained from the image sensor 800, may be transmitted to the mobile device 1000. Alternatively, information related to the target food O, obtained from the gas sensor 100, may also be transmitted to the mobile device 1000. The mobile device 1000 may include a device that is capable of communicating with the refrigerator 900. For example, the mobile device 100 may include a smartphone, a tablet PC, or the like. The mobile device 1000 may receive data received from the refrigerator 900, analyze the received data, and calculate information regarding the type and state of the target food O in the same manner as in the controller 930 of the refrigerator 900 so that the user can recognize the calculated information regarding the type and state of the target food O. Alternatively, the controller 930 of the refrigerator 900 receives the calculated information regarding the type and state of the target food O, so that the user can recognize the received information.

The mobile device 1000 receives image data of the gas sensor 100, determines the type or state of the target food O on the basis of the received image data, displays the determined state for user recognition, receives a user-desired command, and has an application having a user interface through which a user-desired command is received and transmitted to the refrigerator 900. Communication between the mobile device 1000 and the refrigerator 900 may be short range wireless communication such as Wi-Fi or Bluetooth, or may be long range wireless communication. Therefore, the user may not directly confirm the display 910 of the refrigerator 900, and may frequently confirm a state of the refrigerator 900 through the mobile device 1000 indoors or outdoors.

FIG. 38 is a block diagram illustrating a mobile device 1000 according to a first embodiment of the present disclosure.

Referring to FIG. 38, the mobile device 1000 according to the first embodiment of the present disclosure may include a camera for acquiring an image of the gas sensor 100, a controller 1200 for deciding the type and state of the target food O from the image acquired from the camera, a display 1300 for displaying information decided by the controller 1200, and a communication part 1400 for communicating with the refrigerator 900.

The user may capture an image of the gas sensor 100 of a desired container C to be confirmed using the camera of the mobile device 1000 of the embodiment of the present disclosure. If the image of the gas sensor 100 is acquired from the camera, the controller 930 may calculate a color difference between a first image obtained before exposure to the target gas and a second image obtained after exposure to the target gas.

If the color coordinate system of the image acquired from the camera is denoted by the L-a-b coordinate system, the controller 1200 may convert the calculated color difference into the RGB coordinate system and may display the RGB conversion result. Conversion into the RGB coordinate system is merely exemplary, and a color difference may be expressed by other kinds of coordinate systems. The controller 1200 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O.

The controller 1200 may configure the discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 1200 may prestore data regarding patterns of the respective RGB regions indicating the type of the target food O and the state of the target food O. The controller 1230 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O. The mobile device 1000 may display the determined type and state of the target food O on the display 1300 such that the user may recognize the determined type and state of the target food O.

The mobile device 1000 according to the first embodiment of the present disclosure may include an application for deciding the type and state of the target food O using the above-mentioned methods, upon receiving the gas sensor image acquired from the camera. As a result, the user may easily recognize the type or state of the target food O by driving the application. As can be seen from FIG. 37, the mobile device 1000 may receive image data of the gas sensor 100 or information regarding the type and state of the target food O from the refrigerator 900, and may provide the user with information regarding the target food O. If the user directly acquires the image of the gas sensor 100 using the camera function, the mobile device 1000 may calculate information regarding the target food O. Furthermore, the user may also adjust a temperature of the storage chamber 903 including the container C storing the target food O using the application of the mobile device 1000. If the user input a command through the application, the mobile device 1000 may transmit the corresponding command to the refrigerator 900 through the communication part 1400.

FIG. 40 is a block diagram illustrating a refrigerator 900 according to a second embodiment of the present disclosure. FIG. 41 is a block diagram illustrating a mobile device 1000 according to a second embodiment of the present disclosure.

Referring to FIG. 40, the refrigerator 900 may include a controller 930, a display 910, a cooling part 950, an input part 920, and a communication part 940. The controller 930 may determine the type and state of the target food O using the gas sensor image received from the gas sensor 300 mounted to the container C. The display 910 may display information regarding the type and state of target food O decided by the controller 930. The cooling part 950 may provide cool air to the storage chamber 903 according to the type and state of the target food O determined by the controller 930, and may adjust a temperature of the storage chamber 903. The input part 920 may enable the user to input a command related to the operation of the refrigerator 900. The communication part 940 may transmit information regarding the type and state of the target food O decided by the controller 930 to the external mobile device 1000.

The gas sensor 300 mounted to the container C is based on the second embodiment of the present disclosure. The gas sensor 300 according to the second embodiment may include an image detector 140 for obtaining an image of the gas sensor 300.

Referring to FIG. 19, the gas sensor 300 according to the second embodiment may include a gas sensor 100 of the first embodiment shown in FIG. 5; an image detector 140 for obtaining an image of the color change of the gas sensor 100; a transmitter 150 for transmitting image data of the gas sensor 100 obtained from the image detector 140, to the external device; and a battery 160 for providing a power source to the image detector 140 and the transmitter 150.

The image detector 140 may use a photodiode, a CMOS image sensor, and a CCD. The image detector 140 may obtain images of the gas sensor 100 so as to detect color change of the detector 120 contained in the gas sensor 100. The image detector 140 may successively obtain the images of the gas sensor 100, and may obtain data regarding the color change by sampling the acquired images. Alternatively, the image detector 140 may obtain data of the color change by obtaining the image of the gas sensor 100 at intervals of a predetermined time.

The obtained data may be transmitted to the refrigerator 900 of the second embodiment including the communication part 940 through the transmitter 150. Various wireless communication schemes may be used for communication between the transmitter 150 of the gas sensor 300 and the communication part 940 of the refrigerator 900.

If the communication part 940 of the refrigerator 900 receives image data of the gas sensor 300 from the transmitter 150 of the gas sensor 300, the controller 930 of the refrigerator 900 may calculate a color difference between a first image obtained before exposure to target gas and a second image after exposure to the target gas. That is, the controller 930 may calculate a color difference between a first color obtained before the detector 120 constructing the gas sensor 300 is exposed to the target gas and a second color obtained after the detector 120 constructing the gas sensor 300 is exposed to the target gas, such that the controller 930 can recognize the presence or absence of color change of the detector and can also recognize the degree of color change. For example, after exposure to the initial color of each detector 120 and the target gas and the detector 120 is then exposed to the target gas, the controller

930 may calculate a difference between colors of the detector 120 shown in the images transmitted from the gas sensor 300. In this case, the user can recognize the degree of color change on the basis of a specific time before exposure to the target gas. Alternatively, the controller 930 may continuously calculate a color difference between a color of the detector shown in the image currently transmitted from the gas sensor 300 and a color of the detector 120 shown in the previously transmitted image. In this case, the user may recognize the degree of discoloration as time goes by. The controller 930 can obtain desired data through a predetermined operation, irrespective of the scheme for calculating such color difference.

If the color coordinate system of the image transmitted from the gase sensor 300 is denoted by the L-a-b coordinate system, the controller 1200 may convert the calculated color difference into the RGB coordinate system and may display the RGB conversion result. Conversion into the RGB coordinate system is merely exemplary, and a color difference may be expressed by other kinds of coordinate systems.

The controller 930 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O.

The controller 930 may configure discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 930 may prestore data regarding patterns of the respective RGB regions indicating the type of the target food O and the state of the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O.

The controller 930 may display the type and state of the target food O on the display 910 when the type and state of the target food are decided. For example, if the target food O is kimchi and this kimchi is raw kimchi, the controller 930 may display information indicating that a kimchi state is raw kimchi on the display 910.

If the user inputs a desired command for displaying such information, the food type and food state information is displayed on the display 910 in response to the input command. For example, if the user selects the container C to be confirmed through the input part 920, the controller 930 may display the type and state of the target food O, obtained from the image received from the image detector 140 configured to obtain the image of the gas sensor 300 of the selected container C, on the display 910. If the target food O stored in the selected container C is kimchi and this kimchi is raw kimchi, the controller 930 may display specific information indicating that kimchi is stored in the corresponding container C and this kimchi is raw kimchi. The input part 920 may have a user interface through which the user can intuitively select the container C. The display 910 may also have a user interface through which the user can intuitively recognize the type and state of the target food O.

The user may confirm information displayed on the display 910, and may input a command for a desired state of the target food O through the input part 920. The controller 930 may receive a command regarding a desired state of the target food O through the input part 920, so that it may control a temperature of the storage chamber 903. For example, if the user inputs a desired command for maintaining a current kimchi state through the input part 920, the controller 930 may decide a temperature of the storage chamber 903 in such a manner that the kimchi state can be maintained in consideration of a current kimchi state, and may transmit a control signal to the cooling part 950 so as to adjust a temperature of the storage chamber 903. Alternatively, if the user inputs a desired command for ripening the kimchi through the input part 920, the controller 930 may determine a temperature of the storage chamber 903 in consideration of a current kimchi state so that the kimchi can be further ripened at the determined temperature. The controller 930 transmits a control signal corresponding to the determined temperature to the cooling part 950, and adjusts a temperature of the storage chamber 903.

Alternatively, the controller 930 may determine a temperature of the storage chamber 903 in response to the determined type and state of the target food O in such a manner that the target food O reaches an optimum ripening state and the optimum ripening state can be maintained at the determined temperature. The controller 930 may transmit a control signal corresponding to the determined temperature to the cooling part 950, so that it may automatically adjust the temperature of the storage chamber 903.

If information regarding a user-desired storage state of the target food O is previously input, the controller 930 may monitor the color change of the gas sensor 300 and may automatically control a temperature of the storage chamber 903 in response to the state of the target food O, so that the target food O reaches a desired storage state and this desired storage state can be maintained.

In addition, the refrigerator 900 according to the second embodiment may immediately transmit image data of the gas sensor 300, received from the gas sensor 300, to the mobile device 1000, or may transmit target food-associated information from the image of the gas sensor 300 to the mobile device 1000. The mobile device 1000 may receive data received from the refrigerator 900, analyze the received data, and calculate information regarding the type and state of target food O in the same manner as in the controller 930, so that the user can recognize the calculated information. Alternatively, the controller 930 of the refrigerator 900 may receive information regarding the pre-calculated target food type and state, and display the received information for user recognition.

The mobile device 1000 according to the second embodiment of the present disclosure will hereinafter be described with reference to FIG. 41.

Referring to FIG. 41, the mobile device 1000 according to the second embodiment may include a communication part 1400 for receiving data from the gas sensor 300 or the refrigerator 900, a controller 1200 for deciding the type and state of the target food O upon receiving data from the communication part 1400, and a display 1300 for displaying information decided by the controller 1200. The mobile device 1000 may not acquire the image of the gas sensor 300 using the camera of the mobile device 1000, may directly receive image data of the gas sensor 300 from the image detector 140 of the gas sensor 300 mounted to the container C, or may transmit image data of the gas sensor 300 from the refrigerator 900. Alternatively, the mobile device 1000 may receive information regarding the predetermined target food type and state from the refrigerator 900.

Upon receiving the gas sensor image 300 from the gas sensor 300 or the refrigerator 900, the controller may calculate a color difference between a first image obtained before exposure to target gas and a second image obtained after exposure to the target gas.

If the color coordinate system of the image acquired from the image detector 140 is denoted by the L-a-b coordinate system, the controller 1200 may convert the calculated color difference into the RGB coordinate system and may display the RGB conversion result. Conversion into the RGB coordinate system is merely exemplary, and a color difference may be expressed by other kinds of coordinate systems. The controller 1200 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O.

The controller 1200 may configure the discoloration data of the detector 120 constructing the gas sensor 300 and data indicating the type and state of the target food O corresponding to the color change (discoloration) of the detector 120 in the form of a database (DB), so that the DB-formatted result can be pre-stored. For example, the controller 1200 may prestore data regarding patterns of the respective RGB regions indicating the type of the target food O and the state of the target food O. The controller 1230 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O. The mobile device 1000 may display the determined type and state of the target food O on the display 1300 such that the user may recognize the determined type and state of the target food O.

The mobile device 1000 according to the second embodiment of the present disclosure may include an application for deciding the type and state of the target food O using the above-mentioned methods, upon receiving the gas sensor image acquired from the gas sensor 300 or the refrigerator 900. As a result, the user may easily recognize the type or state of the target food O by driving the application. The mobile device 1000 may receive image data of the gas sensor 300 from the gas sensor 300 or the refrigerator 900, may determine the type and state of the target food O, and may provide the user with information regarding the target food O. Furthermore, the user may also adjust a temperature of the storage chamber 903 including the container C storing the target food O using the application of the mobile device 1000. If the user input a command through the application, the mobile device 1000 may transmit the corresponding command to the refrigerator 900 through the communication part 1400.

FIG. 42 is a block diagram illustrating a refrigerator 900 according to a third embodiment of the present disclosure. FIG. 43 is a diagram illustrating a coupling structure between a gas sensor of a refrigerator and a container C according to a third embodiment of the present disclosure.

Referring to FIG. 42, the refrigerator 900 may include a gas sensor 100, an image sensor 800, a controller 930, a display 910, a cooling part 950, an input part 920, and a communication part 940. The gas sensor 100 is coupled to the container C contained in the storage chamber 903, so that it can detect the target gas generated from the target food O stored in the container C. The image sensor 800 may obtain an image of the gas sensor 100. The controller 930 may determine a state of the target food O using the images obtained from the image sensor 800. The display 910 may display information regarding the target food type and state decided by the controller 930. The cooling part 950 may provide cool air to the storage chamber 903 in response to the target food type and state decided by the controller 930. The input part 920 may enable the user to input commands associated with the operations of the refrigerator 900. The communication part 940 may transmit information regarding the target food state decided by the controller 930 to the external mobile device 1000.

In accordance with this embodiment, the gas sensor 100 is not mounted to the container C and is stored in the storage chamber 903 of the refrigerator 900 including the container C. The gas sensor 100 may obtain the correct detection result under the shielded environment. Therefore, as can be seen from FIG. 43, the gas sensor 100 along with a predetermined instrument part to be coupled to the container C may be installed in the storage chamber 903. The container C may have a specific structure coupled to the instrument part including the gas sensor 100. The instrument part shown in FIG. 43 is similar in structure to the instrument part 600 shown in FIGS. 23 to 25.

The instrument part may include a main body 620 in which the gas sensor 100 is installed. A fixing part 640 coupled to a fixing groove 621 formed at the wall of the container C is located at a lower part and an upper part of the main body, so that the instrument part can be fixed to the wall of the container C when contacting the wall of the container C. The fixing part 640 is fixed to couple the instrument part to the container C. If the instrument part is coupled to the container C, the scope or spirit of the present disclosure is not limited to the shape, structure, position, and numbers shown in FIG. 43, and can also be applied to other shapes, other structures, other positions, and other numbers without change.

The gas sensor 100 may be separately mounted to the main body 630, or the gas sensor 100 along with the additional gas permeation layer may be mounted to the main body 630.

A fixing groove 621 coupled to the fixing part 640 of the instrument part may be formed in the container C, and the fixing groove 621 may have a shape, structure, position, and number corresponding to the shape, structure, position, and number of the fixing parts. When the gas sensor 100 is coupled to the instrument part, a hole 615 is formed at the wall of the container C so that the gas sensor 100 can detect target gas generated from the target food O stored in the container C. A gas permeation layer for transmitting only gas without transmitting liquid or solid may be installed so that the gas permeation layer can prevent the target food O accommodated in the container C from exiting the container C through the hole. When the container C is located in the storage chamber 903, the user may couple the container C to the above-mentioned instrument part in such a manner that the hole 615 of the container C is coupled to the gas sensor 100 of the storage chamber 903.

The coupling structure shown in FIG. 43 is merely exemplary, and the coupling structure between the gas sensor 100 and the container C is conceptually contained in the scope of the present disclosure. Here, this gas sensor 100 is designed to detect the target gas generated from the container C.

Since the gas sensor 100 is coupled to the container C, the gas sensor 100 may detect the target gas. If color change occurs, the image sensor 800 may obtain the image of the gas sensor 100.

The image sensor 800 may use a photodiode, a CMOS image sensor, and a CCD. The image sensor 800 may obtain an image of the gas sensor 100 so as to detect the color change of the detector 120 contained in the gas sensor 100. The image sensor 800 may acquire the image of the gas sensor 100 so as to detect color change (discoloration) of each detector 120 contained in the gas sensor 100. The categories of the image sensor 800 are not limited to the above-mentioned examples, and all the optical devices capable of acquiring the image of the gas sensor 100 may be contained in the image sensor 800 of the present disclosure. As many image sensors 800 as the number of gas sensors 100 contained in the storage chamber 903 are provided, so that the image sensor can obtain the image of each gas sensor 100.

The image sensor 800 may successively obtain the image of the gas sensor 100, may obtain data of the color change by sampling the obtained image, and may obtain the image of the gas sensor 100 at intervals of a predetermined time, so that the image sensor 800 may obtain the data regarding the color change. If the image sensor 800 obtains the image of the gas sensor 100 and transmits the obtained image to the controller 930, the controller 930 may calculate a color difference between a first image obtained before exposure to the target gas and a second image obtained after exposure to the target gas. That is, the controller 930 calculates a color difference between the first color obtained before exposure to target gas of the detector 120 constructing the gas sensor 100 and the second color obtained after exposure to target gas of the detector 120, so that the controller 930 may calculate the presence or absence of color change (discoloration) of the detector 120 and the degree of discoloration. For example, after exposure to the initial color and the target gas of the detector 120, a color difference of the detector 120, shown in the images received from the image sensor 800, is calculated. In this case, the degree of discoloration can be recognized on the basis of a specific time before the sensor is exposed to the target gas. Alternatively, a color difference between the detector 120's color shown in a currently transmitted image and the other detector 120's color shown in a previously transmitted image is continuously calculated. In this case, it may be possible to recognize the degree of discoloration as time goes by. Although the color difference is calculated using any one of the above-mentioned schemes, it should be noted that desired data can be obtained through a predetermined operation.

If the color coordinate system of the image acquired from the image sensor 800 is denoted by the L-a-b coordinate system, the controller 930 may convert the calculated color difference into the RGB coordinate system and may display the RGB conversion result. Conversion into the RGB coordinate system is merely exemplary, and a color difference may be expressed by other kinds of coordinate systems.

As shown in FIG. 39, the controller 930 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O.

The controller 930 may configure discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 930 may prestore data regarding patterns of the respective RGB regions indicating the type of the target food O and the state of the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O.

The controller 930 may display the type and state of the target food O on the display 910 when the type and state of the target food are decided. For example, if the target food O is kimchi and this kimchi is raw kimchi, the controller 930 may display information indicating that a kimchi state is raw kimchi on the display 910.

If the user inputs a desired command for displaying such information, the food type and food state information is displayed on the display 910 in response to the input command. For example, if the user selects the container C to be confirmed through the input part 920, the controller 930 may display the type and state of the target food O, calculated from the image received from the image sensor 800 configured to obtain the image of the gas sensor 300 for sensing target gas of the selected container C, on the display 910. If the target food O stored in the selected container C is kimchi and this kimchi is raw kimchi, the controller 930 may display specific information indicating that kimchi is stored in the corresponding container C and this kimchi is raw kimchi. The input part 920 may have a user interface through which the user can intuitively select the container C. The display 910 may also have a user interface through which the user can intuitively recognize the type and state of the target food O.

The user may confirm information displayed on the display 910, and may input a command for a desired state of the target food O through the input part 920. The controller 930 may receive a command regarding a desired state of the target food O through the input part 920, so that it may control a temperature of the storage chamber 903. For example, if the user inputs a desired command for maintaining a current kimchi state through the input part 920, the controller 930 may decide a temperature of the storage chamber 903 in such a manner that the kimchi state can be maintained in consideration of a current kimchi state, and may transmit a control signal to the cooling part 950 so as to adjust a temperature of the storage chamber 903. Alternatively, if the user inputs a desired command for ripening the kimchi through the input part 920, the controller 930 may determine a temperature of the storage chamber 903 in consideration of a current kimchi state so that the kimchi can be further ripened at the determined temperature. The controller 930 transmits a control signal corresponding to the determined temperature to the cooling part 950, and adjusts a temperature of the storage chamber 903.

Alternatively, the controller 930 may determine a temperature of the storage chamber 903 in response to the determined type and state of the target food O in such a manner that the target food O reaches an optimum ripening state and the optimum ripening state can be maintained at the determined temperature. The controller 930 may transmit a control signal corresponding to the determined temperature to the cooling part 950, so that it may automatically adjust the temperature of the storage chamber 903. If information regarding a user-desired storage state of the target food O is previously input, the controller 930 may monitor the color change of the gas sensor 300 and may automatically control a temperature of the storage chamber 903 in response to the state of the target food O, so that the target food O reaches a desired storage state and this desired storage state can be maintained.

As shown in FIGS. 36A and 36B, if the gas sensor is not coupled to the container, the gas sensor may detect target gas generated from the target food stored in an installation region of the gas sensor. If the target food stored in a specific shelf becomes rotten, the gas sensor may detect the gas generated from the rotting process, so that the image of the discolored gas sensor can be obtained from the image sensor.

If the image sensor 800 obtains the image of the gas sensor 100 and transmits the obtained image to the controller 930, the controller 930 may calculate a color difference between a first image obtained before exposure to target gas and a second image obtained after exposure to the target gas. That is, the controller 930 may calculate a color difference between a first color obtained before exposure to the target gas of the detector 120 constructing the gas sensor 100 and a second color obtained after exposure to the target gas, so that the controller 930 may calculate the presence or absence of color change (discoloration) and the degree of such discoloration. If the color coordinate system of the image acquired from the image sensor 800 is denoted by the L-a-b coordinate system, the controller 930 may convert the calculated color difference into the RGB coordinate system and may display the RGB conversion result. Conversion into the RGB coordinate system is merely exemplary, and a color difference may be expressed by other kinds of coordinate systems.

As shown in FIG. 39, the controller 930 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O.

If a state of the target food O is a rotten state, the controller 930 may determine the position of the image sensor having transmitted the image indicating the rotten food state to be the position of rotten food. The installation position of each image sensor may be prestored, and the controller may decide the storage position of the rotten food on the basis of the prestored position information. The controller may display the position of rotten food on the display so that the user can recognize the rotten state of the food.

In addition, the refrigerator 900 according to a third embodiment includes a communication part 940 configured to communicate with the external mobile device 1000, and image data of the gas sensor 100, obtained from the image sensor 800, may also be transmitted to the mobile device 1000. Alternatively, information related to the target food O, obtained from the image of the gas sensor 100, may also be transmitted to the mobile device 1000. The mobile device 1000 receives data transmitted from the refrigerator 900, analyzes the received data, and calculates information regarding the type and state of the target food O, so that the user can recognize the calculated information. Alternatively, the controller 930 of the refrigerator 900 receives the previously calculated state information of the type and state of the target food O, so that the user can recognize the received information. The mobile device 1000 receives image data of the gas sensor 100, determines the type and state of the target food O on the basis of the received image data, and displays the determined food type and state for user recognition. The mobile device 1000 may have an application having a user interface through which a user-desired command is received and transmitted to the refrigerator 900. Communication between the mobile device 1000 and the refrigerator 900 may be short-distance wireless communication such as Wi-Fi or Bluetooth, or may be long-distance wireless communication. Therefore, the user may not directly confirm the display 910 of the refrigerator 900, and may frequently confirm a state of the refrigerator 900 through the mobile device 1000 indoors or outdoors.

FIG. 44 is a flowchart illustrating a method for controlling the refrigerator 900 according to the first embodiment of the present disclosure. Referring to FIG. 44, the image of the gas sensor 100 of the container C may be acquired from the image sensor 800 provided in the refrigerator 900 (operation 200).

The image sensor 800 is installed at the storage chamber 903 of the refrigerator 900 or the shelf or door of the refrigerator 900 as shown in FIGS. 27 to 30, so that the image sensor 800 obtains the image of the gas sensor 100 mounted to the container C. The image sensor 800 may be any one of a photodiode, a CMOS image sensor, and a CCD. The image sensor 800 may obtain the image of the gas sensor 100 so as to detect the color change of each detector 120 contained in the gas sensor 100. A plurality of containers C, each of which includes the gas sensor 100, may be accommodated in the storage chamber 903, and the image sensor 800 is installed at each space in which the container C can be located so that a plurality of image sensors 800 may also be installed as necessary.

The image sensor 800 may successively obtain the image of the gas sensor 100, may obtain data of the color change by sampling the obtained image, and may obtain the image of the gas sensor 100 at intervals of a predetermined time, so that the image sensor 800 may obtain the data regarding the color change.

If the image sensor 800 acquires the image of the gas sensor 100, the controller 930 of the refrigerator 200 may calculate a color difference between a gas sensor 100's image obtained before exposure to target gas and another gas sensor 100's image obtained after exposure to the target gas (Operation 210).

If the image sensor 800 obtains an image of the gas sensor 100 and transmits the obtained image to the controller 930, the controller 930 may calculate a difference in color between a pre-image obtained before the image sensor 800 is exposed to the target gas and a post image obtained after the image sensor 800 is exposed to the target gas. That is, the controller 930 may calculate a difference in color between a first color obtained before the image sensor 800 is exposed to target gas of the detector 120 constructing the gas sensor 100 and a second color obtained after the image sensor 800 is exposed to the target gas of the detector 120, so that the controller 930 may calculate the presence or absence of color change of the detector 120 and the degree of such color change. For example, after exposure to the initial color and the target gas of the detector 120, a color difference of the detector 120, shown in the images received from the image sensor 800, is calculated. In this case, the degree of discoloration can be recognized on the basis of a specific time before the sensor is exposed to the target gas. Alternatively, a color difference between the detector 120's color shown in a currently transmitted image and the other detector 120's color shown in a previously transmitted image is continuously calculated. In this case, it may be possible to recognize the degree of discoloration as time goes by. Although the color difference is calculated using any one of the above-mentioned schemes, it should be noted that desired data can be obtained through a predetermined operation.

If a color coordinate system of the image obtained from the image sensor 800 is the L-a-b coordinate system, the calculated color difference is converted into the RGB coordinate system, and then displayed. The operation for performing such conversion into the RGB coordinate system and displaying the conversion result is merely exemplary, and a color difference may be displayed using other kinds of coordinate systems.

If the color difference is calculated, the controller 930 may compare the pattern of the calculated color difference with the prestored data, and may thus determine the type and state of the target food O (Operation 220).

As shown in FIG. 39, the controller 930 may remove a background part other than the detector 120 from the image indicating the detector 120's color difference image converted into the RGB coordinate system. The controller 930 may classify the image from which the background part is removed into a plurality of images according to the RGB regions, may compare each of a pattern of the R region, a pattern of the G region, and a pattern of the B region with prestored data, and may obtain information regarding the target food O.

The controller 930 may configure discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 930 may prestore data regarding patterns of the respective RGB regions indicating the type of the target food O and the state of the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the food type and food state expressed by the determined pattern to be the type and state of the target food O.

If the user detects the color change of the gas sensor 100 using the image sensor and uses the DB information, instead of observing the color change of the gas sensor 100 with the naked eye, the type and state of food can be more accurately determined.

If the type and state of target food O are decided, the display 910 of the refrigerator 900 may display the decided food type and state (Operation 230). The controller 930 may control a temperature of the storage chamber 903 on the basis of the determined type and state of the target food O (Operation 240).

If the type and state of the target food O are determined, the controller 930 may display the type and state of the target food O determined through the display 910. For example, if the target food O is kimchi and the kimchi is raw kimchi, the controller 930 may display a kimchi state indicating raw kimchi on the display 910.

If the user inputs a desired command for displaying such information, the controller 930 may display information regarding the type and state of food on the display 910. For example, if the user selects the container C to be confirmed through the input part 920, the controller 930 may display the type and state of the target food O calculated from the images received from the image sensor 800 configured to detect the gas sensor 100 of the selected container C on the display 910. If the target food O stored in the selected container C is kimchi and this kimchi is raw kimchi, the controller 930 may display specific information on the display 910, the specific information indicating that kimchi is stored in the corresponding container C and this kimchi is raw kimchi. The input part 920 may have a user interface through which the user can intuitively select the container C. The display 910 may have a user interface through which the user can intuitively select the type and state of the target food O.

The user may confirm information displayed on the display 910, and may input a command for a desired state of the target food O through the input part 920. The controller 930 may receive a command regarding the target food O from the user through the input part 920, so that the controller 930 may control a temperature of the storage chamber 903. For example, if the user inputs a command for maintaining a current kimchi state through the input part 920, the controller 930 may determine a temperature (capable of maintaining a current kimchi state) of the storage chamber 903 in consideration of a current kimchi state, and adjust a temperature of the storage chamber 903 by transmitting a control signal to the cooling part 950. Alternatively, if the user inputs a desired command for kimchi ripening through the input part 920, the controller 930 may determine a temperature of the storage chamber 903 in consideration of a current kimchi state so as to perform additional ripening of the kimchi, may transmit a control signal corresponding to the determined temperature to the cooling part 950, and may thus adjust a temperature of the storage chamber 903.

Alternatively, the controller 930 may determine a temperature of the storage chamber 903 in such a manner that the target food O reaches an optimum ripening state and the optimum ripening state can be maintained in response to the determined type and state of the target food O, may transmit a control signal corresponding to the determined temperature to the cooling part 950, and may thus automatically adjust the temperature of the storage chamber 903.

If information regarding a user-desired storage state of the target food O is previously input, the controller 930 may monitor the color change of the gas sensor 100 and may automatically control a temperature of the storage chamber 903 in response to the state of the target food O, so that the target food O reaches a desired storage state and this desired storage state can be maintained.

FIG. 45 is a flowchart illustrating a method for controlling the refrigerator 900 according to the second embodiment of the present disclosure. Referring to FIG. 45, the refrigerator 900 may receive image data of the gas sensor 300 from the gas sensor mounted to the container (Operation 250). The gas sensor 300 mounted to the container C may be based on the second embodiment of the present disclosure, and may include an image detector 140 configured to acquire an image of the gas sensor 300.

Referring to FIG. 19, the gas sensor according to the second embodiment may include a gas sensor 100 of FIG. 5, an image detector 140 for obtaining an image regarding the color change of the gas sensor 100, a transmitter 150 for transmitting the gas-sensor image data obtained by the image detector 140 to an external part, and a battery 160 for providing a power source to operate the image detector 140 and the transmitter 150. The image detector 140 may use a photodiode, a CMOS image sensor, and a CCD. The image detector 140 may obtain images of the gas sensor so as to detect color change of each detector 120 contained in the gas sensor 100. The image detector 140 may successively obtain the images of the gas sensor 100, and may obtain data regarding the color change by sampling the acquired images. Alternatively, the image detector 140 may obtain data of the color change by obtaining the image of the gas sensor 100 at intervals of a predetermined time.

The obtained data may be transmitted to the second embodiment's refrigerator 900 including the communication part 940 through the transmitter 150. Various communication schemes between the transmitter 150 of the gas sensor 300 and the communication part 940 of the refrigerator 900 may use various wireless communication schemes.

Upon receiving image data from the gas sensor 300, the controller 930 of the refrigerator 900 may calculate a color difference between a pre-image obtained before exposure to the target gas and a post image obtained after exposure to the target gas (Operation 260).

If the communication part 940 of the refrigerator 900 receives the gas sensor 120's image data received from the transmitter 150 of the gas sensor 300, the controller 930 of the refrigerator 900 may calculate a color difference between a first image obtained before exposure to the target gas and a second image obtained after exposure to the target gas. That is, the controller 930 calculates a color difference between the first color obtained before exposure to target gas of the detector 120 constructing the gas sensor 300 and the second color obtained after exposure to target gas of the detector 120, so that the controller 930 may calculate the presence or absence of color change (discoloration) of the detector 120 and the degree of discoloration. For example, after exposure to the initial color and the target gas of the detector 120, a color difference of the detector 120, shown in the images received from the gas sensor 300, is calculated. In this case, the degree of discoloration can be recognized on the basis of a specific time before the sensor is exposed to the target gas. Alternatively, a color difference between the detector 120's color shown in a currently transmitted image and the other detector 120's color shown in a previously transmitted image is continuously calculated. In this case, it may be possible to recognize the degree of discoloration as time goes by. Although the color difference is calculated using any one of the above-mentioned schemes, it should be noted that desired data can be obtained through a predetermined operation.

If the color coordinate system of the image acquired from the gas sensor 800 is denoted by the L-a-b coordinate system, the controller 930 may convert the calculated color difference into the RGB coordinate system and may display the RGB conversion result. Conversion into the RGB coordinate system is merely exemplary, and a color difference may be expressed by other kinds of coordinate systems.

If the color difference is calculated, the controller 930 may compare the calculated color difference pattern with the prestored data, and may thus determine the type and state of target food (Operation 270).

As shown in FIG. 39, the controller 930 may remove a background part other than the detector 120 from the image indicating the detector 120's color difference image converted into the RGB coordinate system. The controller 930 may classify the image from which the background part is removed into a plurality of images according to the RGB regions, may compare each of the patterns of the RGB regions with prestored data, and may obtain information regarding the target food O.

The controller 930 may configure discoloration data of the detector 120 constructing the gas sensor 100 and data indicating the type and state of the target food O corresponding to the color change (discoloration) of the detector 120 in the form of a database (DB), so that the DB-formatted result can be pre-stored. For example, the controller 930 may prestore data regarding patterns of the respective RGB regions indicating the type of the target food O and the state of the target food O. The controller 930 may compare the RGB regions' patterns obtained when the image from which the background part is removed is classified into a plurality of images according the RGB regions with the patterns stored in the database (DB), may determine a matched pattern according to the result of comparison, and may determine the type and state of target food O expressed by the determined pattern to be the type and state of the target food O.

When the type and state of the target food are decided, the controller 930 may display the type and state of the target food O on the display 910 (Operation 280). The controller 930 may control a temperature of the storage chamber 903 on the basis of the determined type and state of the target food O (Operation 290).

The controller 930 may display the type and state of the target food O on the display 910 when the type and state of the target food are decided. For example, if the target food O is kimchi and this kimchi is raw kimchi, the controller 930 may display information indicating that a kimchi state is raw kimchi on the display 910.

If the user inputs a desired command for displaying such information, the food type and food state information is displayed on the display 910 in response to the input command. For example, if the user selects the container C to be confirmed through the input part 920, the controller 930 may display the type and state of the target food O, calculated from the image received from the image sensor 800 configured to obtain the image of the gas sensor 300 of the selected container C, on the display 910. If the target food O stored in the selected container C is kimchi and this kimchi is raw kimchi, the controller 930 may display specific information indicating that kimchi is stored in the corresponding container C and this kimchi is raw kimchi. The input part 920 may have a user interface through which the user can intuitively select the container C. The display 910 may also have a user interface through which the user can intuitively recognize the type and state of the target food O.

The user may confirm information displayed on the display 910, and may input a command for a desired state of the target food O through the input part 920. The controller 930 may receive a command regarding a desired state of the target food O through the input part 920, so that it may control a temperature of the storage chamber 903. For example, if the user inputs a desired command for maintaining a current kimchi state through the input part 920, the controller 930 may decide a temperature of the storage chamber 903 in such a manner that the kimchi state can be maintained in consideration of a current kimchi state, and may transmit a control signal to the cooling part 950 so as to adjust a temperature of the storage chamber 903. Alternatively, if the user inputs a desired command for ripening the kimchi through the input part 920, the controller 930 may determine a temperature of the storage chamber 903 in consideration of a current kimchi state so that the kimchi can be further ripened at the determined temperature. The controller 930 transmits a control signal corresponding to the determined temperature to the cooling part 950, and adjusts a temperature of the storage chamber 903.

Alternatively, the controller 930 may determine a temperature of the storage chamber 903 in response to the determined type and state of the target food O in such a manner that the target food O reaches an optimum ripening state and the optimum ripening state can be maintained at the determined temperature. The controller 930 may transmit a control signal corresponding to the determined temperature to the cooling part 950, so that it may automatically adjust the temperature of the storage chamber 903.

If information regarding a user-desired storage state of the target food O is previously input, the controller 930 may monitor the color change of the gas sensor 300 and may automatically control a temperature of the storage chamber 903 in response to the state of the target food O, so that the target food O reaches a desired storage state and this desired storage state can be maintained.

Although the embodiments of the present disclosure have been disclosed for illustrative purposes, those skilled in the art will appreciate that various modifications, additions and substitutions are possible, without departing from the scope and spirit of the invention as disclosed in the accompanying claims.

The invention claimed is:

1. A refrigerator comprising:
a storage chamber;
an image sensor configured to detect a color of a gas sensor included in the storage chamber, and to produce a gas sensor image; and
a controller configured to identify a food stored in the storage chamber on the basis of the gas sensor image produced by the image sensor, and to determine a state of the food stored in the storage chamber on the basis of the gas sensor image produced by the image sensor.

2. The refrigerator according to claim 1, wherein the controller is configured to prestore data regarding discoloration of a plurality of detectors of the gas sensor and data regarding a type and state of a target object based on the discoloration, wherein the controller determines a difference between a gas sensor color obtained before exposure to target gas and a gas sensor color obtained after exposure to the target gas using the image obtained from the image sensor, and identifies the food stored in the storage chamber and determines the state of the food stored in the storage chamber on the basis of the determined color difference using the prestored data.

3. The refrigerator according to claim 1, wherein the controller controls a temperature of the storage chamber according to the determined state of the food stored in the storage chamber.

4. The refrigerator according to claim 1, further comprising:
a display configured to display information regarding an identification of the food stored in the storage chamber or the state of the food stored in the storage chamber determined on the basis of the gas sensor image produced by the image sensor.

5. The refrigerator according to claim 1, wherein to determine the state of the food stored in the storage chamber, the controller identifies a ripening degree of the food stored in the storage chamber.

6. The refrigerator according to claim 1, wherein the sensor comprises a plurality of detectors, each detector detecting a different chemical.

7. The refrigerator according to claim 6, wherein each detector in the plurality of detectors detects a concentration level of the different chemical.

8. The refrigerator according to claim 7, wherein to identify the food stored in the storage chamber, the controller differentiates between at least two potential foods based on chemicals emitted by the food stored in the storage chamber and based on concentration levels respectively of the chemicals emitted by the food stored in the storage chamber.

9. A method for controlling a refrigerator comprising:
determining discoloration of a gas sensor provided in a storage chamber of the refrigerator;
identifying a food stored in the storage chamber on the basis of the discoloration of the gas sensor;
determining a state of the food stored in the storage chamber on the basis of the discoloration of the gas sensor; and
displaying the state of the food stored in the storage chamber corresponding to the discoloration of the gas sensor.

10. The method according to claim 9, wherein the determining the discoloration of the gas sensor includes:
acquiring an image of the gas sensor including a plurality of detectors; and
determining a difference between a color of each detector, obtained before exposure to target gas, and a color of each detector, obtained after exposure to the target gas, using the acquired image of the gas sensor.

11. The method according to claim 9, wherein
the identifying the food stored in the storage chamber includes:
comparing the discoloration of the gas sensor with pre-stored data including discoloration of a plurality of detectors and type data of the food corresponding to the discoloration; and
the determining the state of the food stored in the storage chamber includes:
comparing the discoloration of the gas sensor with pre-stored data including discoloration of the plurality of detectors and state data of the food corresponding to the discoloration.

12. The method according to claim 9, wherein the displaying the state of the food stored in the storage chamber includes:
displaying an identification of the food stored in the storage chamber and displaying the state of the food stored in the storage chamber, determined on the basis of the discoloration of the gas sensor.

13. The method according to claim 9, further comprising:
controlling a temperature of the storage chamber on the basis of the state of the food stored in the storage chamber determined based on the discoloration of the gas sensor.

14. The method according to claim 9, wherein to determine the state of the food stored in the storage chamber, the controller identifies a ripening degree of the food stored in the storage chamber.

15. The method according to claim 9, wherein the sensor comprises a plurality of detectors, each detector detecting a different chemical.

16. The method according to claim 15, wherein each detector in the plurality of detectors detects a concentration level of the different chemical.

17. The method according to claim 16, further comprising differentiating between at least two potential foods based on chemicals emitted by the food stored in the storage chamber and based on concentration levels respectively of the chemicals emitted by the food stored in the storage chamber.

* * * * *